US011130754B2

(12) United States Patent
Liu et al.

(10) Patent No.: US 11,130,754 B2
(45) Date of Patent: *Sep. 28, 2021

(54) SUBSTITUTED BENZAMIDES AS RIPK2 INHIBITORS

(71) Applicant: Boehringer Ingelheim International GmbH, Ingelheim am Rhein (DE)

(72) Inventors: Pingrong Liu, Southbury, CT (US); Craig Andrew Miller, New Milford, CT (US); Maolin Yu, Brookfield, CT (US); Zhonghua Zhang, Ridgefield, CT (US); Sabine Ruppel, New Milford, CT (US); Anil K. Padayana, Lexington, MA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/158,407

(22) Filed: Oct. 12, 2018

(65) Prior Publication Data
US 2019/0048000 A1 Feb. 14, 2019

Related U.S. Application Data

(63) Continuation of application No. 15/696,540, filed on Sep. 6, 2017, now Pat. No. 10,138,241.

(60) Provisional application No. 62/394,779, filed on Sep. 15, 2016.

(51) Int. Cl.
| C07C 233/65 | (2006.01) |
| C07D 471/04 | (2006.01) |
| C07D 231/12 | (2006.01) |
| C07D 403/04 | (2006.01) |
| C07D 401/04 | (2006.01) |
| C07D 417/04 | (2006.01) |
| C07D 417/14 | (2006.01) |
| C07D 487/04 | (2006.01) |

(52) U.S. Cl.
CPC ......... *C07D 471/04* (2013.01); *C07D 231/12* (2013.01); *C07D 401/04* (2013.01); *C07D 403/04* (2013.01); *C07D 417/04* (2013.01); *C07D 417/14* (2013.01); *C07D 487/04* (2013.01)

(58) Field of Classification Search
CPC .................................................... C07C 233/65
USPC ........................................................ 564/183
See application file for complete search history.

(56) References Cited

U.S. PATENT DOCUMENTS

| 7,834,019 B2 | 11/2010 | Sagara et al. |
| 8,889,712 B2 | 11/2014 | Borzilleri et al. |
| 2004/0248853 A1 | 12/2004 | Dyckman et al. |
| 2008/0182837 A1 | 7/2008 | Steurer et al. |
| 2012/0178915 A1 | 7/2012 | Xu |
| 2013/0023532 A1 | 1/2013 | Casillas et al. |
| 2015/0353500 A1 | 12/2015 | Maue et al. |
| 2016/0326140 A1 | 11/2016 | Schwarz et al. |
| 2018/0055832 A1 | 3/2018 | Hayden et al. |
| 2018/0072703 A1 | 3/2018 | Cui et al. |
| 2018/0072717 A1 | 3/2018 | Liu et al. |
| 2019/0048000 A1 | 2/2019 | Lui et al. |

FOREIGN PATENT DOCUMENTS

| WO | 2008055840 A1 | 5/2008 |
| WO | 2009106209 A1 | 9/2009 |
| WO | 2011042797 A1 | 4/2011 |
| WO | 2011120025 A1 | 9/2011 |
| WO | 2011123609 A1 | 10/2011 |
| WO | 2014043446 A1 | 3/2014 |
| WO | 2014122083 A1 | 8/2014 |
| WO | 2014145022 A1 | 9/2014 |
| WO | 2015058140 A1 | 4/2015 |
| WO | 2014081714 A3 | 7/2015 |
| WO | 2016065461 A1 | 5/2016 |

OTHER PUBLICATIONS

Hackam, Daniel G. et al. "Translation of Research Evidence from Animals to Humans" (2006) JAMA vol. 296, No. 14, pp. 1731-1732.
International Search Report for PCT/US2017/050197, dated Nov. 21, 2017.
Jordan, V. Craig "Taxoxifen: A Most Unlikely Pioneering Medicine" (2003) Nature Reviews, Drug Discovery, vol. 2, 205-213.
Kopalli, Spandana Rajendra et al. "Necroptosis inhibitors as therapeutic targets in inflammation mediated disorders a review of the current literature and patents" (2016) Expert Opinion on Therapeutic Patents, vol. 26, No. 11, 1239-1256.
Canning et al., "Inflammatory Signaling by NOD-RIPK2 Is Inhibited by Clinically Relevant Type II Kinase Inhibitors", Chemistry & Biology, 2015, pp. 1176-1185.

*Primary Examiner* — Douglas M Willis
(74) *Attorney, Agent, or Firm* — Edouard G. Lebel

(57) ABSTRACT

The present invention relates to compounds of formula (I):

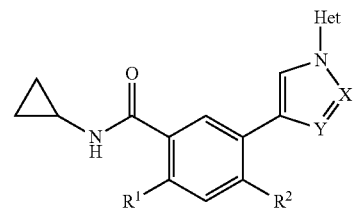

or pharmaceutically acceptable salts thereof, wherein $R^1$, $R^2$, X, Y, and HET are as defined herein. The invention also relates to pharmaceutical compositions comprising these compounds, methods of using these compounds in the treatment of various diseases and disorders, processes for preparing these compounds and intermediates useful in these processes.

14 Claims, No Drawings

SUBSTITUTED BENZAMIDES AS RIPK2 INHIBITORS

BACKGROUND OF THE INVENTION

1. Technical Field

The present invention relates to a series of novel heteroaryl carboxamide compounds, the synthesis of these compounds their use in the treatment of inflammatory disease and pharmaceutical compositions comprising these compounds

2. Background Information

RIPK2 (also known as RICK, CARDIAK, CARD3, or RIP2) is a dual specific serine/threonine and tyrosine kinase which is a key component of pro-inflammatory signaling through the NOD1 and NOD2 signaling pathways (Inohara et al. 1998; McCarthy et al. 1998; Thome et al. 1998; Tigno-Aranjuez et al. 2010). The NOD receptors are one of the mechanisms for surveillance for intracellular bacterial pathogens. Bacterial cell wall components initiate signals through the NOD1 and NOD2 pathway by the binding of NOD1 bacteria ligands, D-glutamyl-meso-diaminopimelic acid, and the NOD2 ligand, muramyl dipeptide, to the appropriate intracellular NOD receptors (Girardin et al. 2003a; Girardin et al. 2003b; Girardin et al. 2003c; Chamaillard et al. 2003; Inohara et al. 2003). This binding induces oligomerization of the NOD protein through homotypic CARD/CARD domain interactions (Inohara et al. 2000; Ogura et al. 2001). This activation of NOD receptors leads to Lys63-linked polyubiquitination of RIPK2 through activation of ubiquitin E3 ligases such as XIAP, cIAP1, cIAP2, TRAF2, TRAF5, and TRAF6 (Krieg et al. 2009; Bertrand et al. 2009; Yang et al. 2007; Hasegawa et al. 2008) and recruits the linear ubiquitin system (LUBAC) (Damgaard et al. 2012; Ver Heul et al. 2013). Additionally, RIPK2 undergoes autophosphorylation of Tyrosine474 as part of its activation and assembly into the NOD signaling complex (Tigno-Aranjuez et al. 2010). Further RIPK2, dependent assembly of the signaling complex results in the activation of IKKα/β/γ and TAK1, leading to activation of NF-κB and MAPK pathways resulting in the production of proinflammatory cytokines (Yang et al. 2007).

Mutations in NOD2 have been linked to multiple diseases. Activating mutations have been linked to Early Onset Sarcoidosis (Kanazawa et al., 2005) and Blau syndrome (Miceli-Richard et al., 2001) which affect skin, joints, and eyes. These activating mutations result in increased basal NF-κB activity (Kanazawa et al., 2005). Loss-of-function mutations in the NOD2 LRR are linked to Crohn's Disease (Ogura et al. 2001; Hugot et al. 2001; Hampe et al. 2001; Hampe 2002; Lesange 2002). In addition, polymorphisms in NOD1 have been linked to atopy (Weidinger et al. 2005) and asthma (Hysi et al. 2005). Additional studies in cellular and in vivo mouse models have suggested a role for NOD1 and NOD2 signaling in a variety of diseases such as Graft vs. Host Disease, Arthritis, Multiple Sclerosis, and Diabetic Nephropathy (Peaneck et al. 2009; Saha et al. 2009; Vieira et al. 2012; Rosenzweig et al. 2010; Joosten et al. 2008; Shaw et al. 2011; Du et al. 2013). Small molecule inhibitors of RIP2 kinase (RIPK2) are disclosed in US2013/0023532 A1 but appear to have limited potency.

Pharmacological inhibition of RIPK2 by a potent and selective small molecule inhibitor will attenuate pro-inflammatory signaling through the bacterial sensing pathways initiated by NOD1 and NOD2 stimulation. This reduction in inflammatory signaling will provide therapeutic benefit in a variety of autoinflammatory diseases. Thus, there is a need for potent inhibitors of RIPK2 for pharmaceutical purposes.

BRIEF SUMMARY OF THE INVENTION

The present invention provides novel heteroaryl carboxamide series of compounds which inhibit the receptor-interacting serine/threonine protein kinase 2 (RIPK2) and are thus useful for treating a variety of diseases and disorders that are mediated or sustained through the activity of RIPK2 including inflammatory, cardiometabolic and cardiovascular diseases and cancer. This invention also relates to pharmaceutical compositions comprising these compounds, methods of using these compounds in the treatment of various diseases and disorders, processes for preparing these compounds and intermediates useful in these processes.

In one aspect of the invention, a compound of this invention has good binding potency.

In another aspect of the invention, a compound this invention exhibits good cellular potency.

In yet another aspect, a compound of this invention exhibits good stability.

In another aspect, a compound of this invention exhibits good cell permeability.

DETAILED DESCRIPTION OF THE INVENTION

In its broadest embodiment, the present invention relates compounds of formula I:

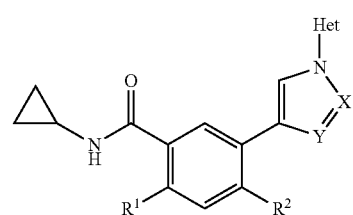

I or pharmaceutically acceptable salts thereof, wherein:
X is N and Y is CH; or
X is CH and Y is N;
HET is a 5-membered heteroaryl ring containing one to three heteroatoms selected from nitrogen and sulfur, wherein each heteroaryl ring is optionally substituted with one to two substituents groups independently selected from $R^3$ and $R^4$; or
HET is a 5-membered heteroaryl ring containing one to three heteroatoms selected from nitrogen and sulfur, wherein each heteroaryl ring is substituted with two substituents groups selected from $R^a$ and $R^b$, wherein $R^a$ and $R^b$ together with the atoms to which they are attached form a 5-6 membered heterocyclic or heteroaryl ring which may be optionally substituted with one to two substituents selected from $R^3$ and $R^4$;
$R^1$ is hydrogen or F;
$R^2$ is $C_{1-3}$ alkyl or Cl;
$R^3$ and $R^4$ are each independently selected from:
(a) —H,
(b) —$OR^5$,
(c) —O—$C_{1-6}$alkyl-O—$C_{1-3}$ alkyl
(d) —O—$C_{3-6}$ cycloalkyl, (e) —C(O)R$^5$,
(f) C$_{1-6}$alkyl optionally substituted with one to three —OH, fluorine, heterocyclyl optionally substituted with oxo, C$_{3-6}$ cycloalkyl, —CO$_2$R$^5$, —O—C$_{1-6}$alkyl, aryl, —N(R$^5$)(R$^6$), or —C(O)N(R$^5$)(R$^6$),
(g) C$_{3-6}$ cycloalkyl optionally substituted with one to three —OH, one to three fluorine, C$_{1-6}$alkyl, —OC$_{1-6}$alkyl, C$_{1-6}$alkyl-OC$_{1-6}$alkyl, C$_{1-6}$alkyl-OH, CF$_3$, —OC$_{3-6}$cycloalkyl, —CO$_2$H, —CO$_2$R$^5$, C$_{3-6}$cycloalkyl, 5-6 membered heteroaryl, C$_{3-6}$ heterocyclyl, N(R$^5$)(R$^6$), or —C(O)N(R$^5$)(R$^6$),
(h) —CO$_2$R$^5$,
(i) —C(O)N(R$^5$)(R$^6$),
(j) —S(O)$_2$N(R$^5$)(R$^6$),
(k) —S(O)$_n$—R$^5$,
(l) a 5-6 membered heteroaryl group optionally substituted with one to three groups selected from C$_{1-6}$alkyl, C$_{3-6}$cycloalkyl, halogen, —CF$_3$, —OH, —(CH$_2$)$_n$CO$_2$R$^5$, —C(O)N(R$^5$)(R$^6$), —N(R$^5$)(R$^6$), —NH—SO$_2$C$_{1-6}$alkyl, C$_{1-6}$alkoxyl, C$_{1-6}$alkyl-O—C$_{1-3}$ alkyl, C$_{1-6}$alkylhydroxyl, C$_{1-3}$alkyl-CN, oxo, phenyl optionally substituted with halogen and —S(O)$_n$ C$_{1-6}$alkyl,
(m) 4-10 membered monocyclic, bicyclic or spirocyclic heterocyclyl group containing N, S or O, wherein each heterocycle is optionally substituted with 1-3 substituents selected from 3-6 membered heterocyclic ring, halogen, —C$_{1-3}$alkyl, —C$_{1-3}$alkyl —O—C$_{1-3}$alkyl and —C$_{1-3}$alkyl-C(O)N(R$^5$)(R$^6$),
(n) aryl,
(o) —N(R$^5$)(R$^6$);
R$^5$ and R$^6$ are each independently selected from —H, 4-6 membered heterocyclyl, —C(O)—C$_{1-3}$ alkyl —C(O)—C$_{1-3}$ cycloalkyl and —(C$_1$-C$_6$)alkyl, wherein each R$^5$ and R$^6$ is independently optionally substituted with —OH, C$_{3-6}$ cycloalkyl, —C$_{1-3}$alkyl, —O—C$_{1-3}$alkyl, —NH—C$_{1-3}$ alkyl or —N—(C$_{1-3}$-alkyl)$_2$; or
R$^5$ and R$^6$ together with the nitrogen atom to which they are attached form a 4-6 membered heterocyclic ring optionally substituted with methyl; and
n is 0, 1, or 2.

In a second embodiment, the present invention relates to a compound as described in the broadest embodiment above, or a pharmaceutically acceptable salt thereof, wherein:
X is N and Y is CH; or
X is CH and Y is N;
Het is a 5-membered heteroaryl ring selected from pyrazolyl, imidazolyl, thiazolyl and thiadiazolyl, wherein each heteroaryl ring is optionally substituted with one to two substituents groups independently selected from R$^3$ and R$^4$; or
Het is a 5-membered heteroaryl ring selected from pyrazolyl and imidazolyl, wherein each heteroaryl ring is substituted with two substituents groups selected from R$^a$ and R$^b$, wherein R$^a$ and R$^b$ together with the atoms to which they are attached form a 5-6 membered heterocyclic or heteroaryl ring which may be optionally substituted with one to two substituents selected from R$^3$ and R$^4$;
R$^1$ is hydrogen or F;
R$^2$ is C$_{1-3}$ alkyl or Cl;
R$^3$ and R$^4$ are each independently selected from:
(a) —H,
(b) —OR$^5$,
(c) —O—C$_{1-6}$alkyl-O—C$_{1-3}$ alkyl
(d) —O—C$_{3-6}$ cycloalkyl,
(e) —C(O)R$^5$,
(f) C$_{1-6}$alkyl optionally substituted with one to three —OH, fluorine, heterocyclyl optionally substituted with oxo, C$_{3-6}$ cycloalkyl, —CO$_2$R$^5$, —O—C$_{1-6}$alkyl, aryl, —N(R$^5$)(R$^6$), or —C(O)N(R$^5$)(R$^6$),
(g) C$_{3-6}$ cycloalkyl optionally substituted with one to three —OH, one to three fluorine, C$_{1-6}$alkyl, —OC$_{1-6}$alkyl, C$_{1-6}$alkyl-OC$_{1-6}$alkyl, C$_{1-6}$alkyl-OH, CF$_3$, —OC$_{3-6}$cycloalkyl, —CO$_2$H, —CO$_2$R$^5$, C$_{3-6}$cycloalkyl, 5-6 membered heteroaryl, C$_{3-6}$ heterocyclyl, N(R$^5$)(R$^6$), or —C(O)N(R$^5$)(R$^6$),
(h) —CO$_2$R$^5$,
(i) —C(O)N(R$^5$)(R$^6$),
(j) —S(O)$_2$N(R$^5$)(R$^6$),
(k) —S(O)$_n$—R$^5$
(l) a 5-6 membered heteroaryl group optionally substituted with one to three groups selected from C$_{1-6}$alkyl, C$_{3-6}$cycloalkyl, halogen, —CF$_3$, —OH, —(CH$_2$)$_n$CO$_2$R$^5$, —C(O)N(R$^5$)(R$^6$), —N(R$^5$)(R$^6$), —NH—SO$_2$C$_{1-6}$alkyl, C$_{1-6}$alkoxyl, C$_{1-6}$alkyl-O—C$_{1-3}$ alkyl, C$_{1-6}$alkylhydroxyl, C$_{1-3}$alkyl-CN, oxo, phenyl optionally substituted with halogen and —S(O)$_n$ C$_{1-6}$alkyl,
(m) 4-10 membered monocyclic, bicyclic or spirocyclic heterocyclyl group containing N, S or O, wherein each heterocycle is optionally substituted with 1-3 substituents selected from 3-6 membered heterocyclic ring, halogen, C$_{1-3}$alkyl, and C$_{1-3}$alkyl-C(O)N(R$^5$)(R$^6$).
(n) aryl,
(o) —N(R$^5$)(R$^6$);
R$^5$ and R$^6$ are each independently selected from —H, 4-6 membered heterocyclyl, —C(O)—C$_{1-3}$ alkyl —C(O)—C$_{1-3}$ cycloalkyl and —(C$_1$-C$_6$)alkyl optionally substituted with —OH, C$_{3-6}$ cycloalkyl, —NH—C$_{1-3}$ alkyl or —N—(C$_{1-3}$-alkyl)$_2$; or
R$^5$ and R$^6$ together with the nitrogen atom to which they are attached form a 5-6 membered heterocyclic ring optionally substituted with methyl; and
n is 0 or 2.

In a third embodiment, the present invention relates to a compound as described in the broadest embodiment above, or a pharmaceutically acceptable salt thereof, wherein:
X is N and Y is CH.

In a fourth embodiment, the present invention relates to a compound as described in the broadest embodiment above, or a pharmaceutically acceptable salt thereof, wherein:
X is CH and Y is N.

In a fifth embodiment, the present invention relates to a compound as described in the broadest embodiment above, or a pharmaceutically acceptable salt thereof, wherein:
HET is a 5-membered heteroaryl ring selected from pyrazolyl, imidazolyl, thiazolyl and thiadiazolyl, wherein each heteroaryl ring is optionally substituted with one to two substituents groups independently selected from R$^3$ and R$^4$;
R$^3$ and R$^4$ are each independently selected from:
(a) —H,
(b) —OR$^5$,
(c) —O—C$_{1-6}$alkyl-O—C$_{1-3}$ alkyl
(d) —O—C$_{3-6}$ cycloalkyl,
(e) —C(O)R$^5$,
(f) C$_{1-6}$alkyl optionally substituted with one to three —OH, fluorine, heterocyclyl optionally substituted with oxo, C$_{3-6}$ cycloalkyl, —CO$_2$R$^5$, —O—C$_{1-6}$alkyl, aryl, —N(R$^5$)(R$^6$), or —C(O)N(R$^5$)(R$^6$),
(g) C$_{3-6}$ cycloalkyl optionally substituted with one to three —OH, one to three fluorine, C$_{1-6}$alkyl, —OC$_{1-6}$alkyl, C$_{1-6}$alkyl-OC$_{1-6}$alkyl, C$_{1-6}$alkyl-OH, CF$_3$, —OC$_{3-6}$cycloalkyl, —CO$_2$H, —CO$_2$R$^5$, C$_{3-6}$cycloalkyl, 5-6 membered heteroaryl, C$_{3-6}$ heterocyclyl, N(R$^5$)(R$^6$), or —C(O)N(R$^5$)(R$^6$),
(h) —CO$_2$R$^5$,
(i) —C(O)N(R$^5$)(R$^6$),
(j) —S(O)$_2$N(R$^5$)(R$^6$),
(k) —S(O)$_n$—R$^5$
(l) a 5-6 membered heteroaryl group optionally substituted with one to three groups selected from C$_{1-6}$alkyl, C$_{3-6}$cycloalkyl, halogen, —CF$_3$, —OH, —(CH$_2$)$_n$CO$_2$R$^5$, —C(O)N(R$^5$)(R$^6$), —N(R$^5$)(R$^6$), —NH—SO$_2$C$_{1-6}$alkyl, C$_{1-6}$alkoxyl, C$_{1-6}$alkyl-O—C$_{1-3}$ alkyl, C$_{1-6}$alkylhydroxyl, C$_1$-3alkyl-CN, oxo, phenyl optionally substituted with halogen and —S(O)$_n$ C$_{1-6}$alkyl,
(m) 4-10 membered monocyclic, bicyclic or spirocyclic heterocyclyl group containing N, S or O, wherein each heterocycle is optionally substituted with 1-3 substituents selected from 3-6 membered heterocyclic ring, halogen, C$_{1-3}$alkyl, and C$_{1-3}$alkyl-C(O)N(R$^5$)(R$^6$).
(n) aryl,
(o) —N(R$^5$)(R$^6$);
R$^5$ and R$^6$ are each independently selected from —H, 4-6 membered heterocyclyl, —C(O)—C$_{1-3}$ alkyl —C(O)—C$_{1-3}$ cycloalkyl and —(C$_1$-C$_6$)alkyl optionally substituted with —OH, C$_{3-6}$ cycloalkyl, —NH—C$_{1-3}$ alkyl or —N—(C$_{1-3}$-alkyl)$_2$; or
R$^5$ and R$^6$ together with the nitrogen atom to which they are attached form a 5-6 membered heterocyclic ring optionally substituted with methyl; and
n is 0 or 2.

In a sixth embodiment, the present invention relates to a compound as described in the broadest embodiment above, or a pharmaceutically acceptable salt thereof, wherein:
HET is a 5-membered heteroaryl ring selected from pyrazolyl and imidazolyl, wherein each heteroaryl ring is substituted with two substituents groups selected from R$^a$ and R$^b$; wherein
R$^a$ and R$^b$ together with the atoms to which they are attached form a 5-6 membered heterocyclic or heteroaryl ring which may be optionally substituted with one to two substituents selected from R$^3$ and R$^4$;
R$^3$ and R$^4$ are each independently selected from:
(a) —H,
(b) —OR$^5$,
(c) —O—C$_{1-6}$alkyl-O—C$_{1-3}$ alkyl
(d) —O—C$_{3-6}$ cycloalkyl,
(e) —C(O)R$^5$,
(f) C$_{1-6}$alkyl optionally substituted with one to three —OH, fluorine, heterocyclyl optionally substituted with oxo, C$_{3-6}$ cycloalkyl, —CO$_2$R$^5$, —O—C$_{1-6}$alkyl, aryl, —N(R$^5$)(R$^6$), or —C(O)N(R$^5$)(R$^6$),
(g) C$_{3-6}$ cycloalkyl optionally substituted with one to three —OH, one to three fluorine, C$_1$-6alkyl, —OC$_{1-6}$alkyl, C$_{1-6}$alkyl-OC$_{1-6}$alkyl, C$_{1-6}$alkyl-OH, CF$_3$, —OC$_{3-6}$cycloalkyl, —CO$_2$H, —CO$_2$R$^5$, C$_{3-6}$cycloalkyl, 5-6 membered heteroaryl, C$_{3-6}$ heterocyclyl, N(R$^5$)(R$^6$), or —C(O)N(R$^5$)(R$^6$),
(h) —CO$_2$R$^5$,
(i) —C(O)N(R$^5$)(R$^6$),
(j) —S(O)$_2$N(R$^5$)(R$^6$),
(k) —S(O)$_n$—R$^5$
(l) a 5-6 membered heteroaryl group optionally substituted with one to three groups selected from C$_{1-6}$alkyl, C$_{3-6}$cycloalkyl, halogen, —CF$_3$, —OH, —(CH$_2$)$_n$CO$_2$R$^5$, —C(O)N(R$^5$)(R$^6$), —N(R$^5$)(R$^6$), —NH—SO$_2$C$_{1-6}$alkyl, C$_{1-6}$alkoxyl, C$_{1-6}$alkyl-O—C$_{1-3}$ alkyl, C$_{1-6}$alkylhydroxyl, C$_1$-3alkyl-CN, oxo, phenyl optionally substituted with halogen and —S(O)$_n$ C$_{1-6}$alkyl, (m) 4-10 membered monocyclic, bicyclic or spirocyclic heterocyclyl group containing N, S or O, wherein each heterocycle is optionally substituted with 1-3 substituents selected from 3-6 membered heterocyclic ring, halogen, C$_{1-3}$alkyl, and C$_{1-3}$alkyl-C(O)N(R$^5$)(R$^6$).
(n) aryl,
(o) —N(R$^5$)(R$^6$);
R$^5$ and R$^6$ are each independently selected from —H, 4-6 membered heterocyclyl, —C(O)—C$_{1-3}$ alkyl —C(O)—C$_{1-3}$ cycloalkyl and —(C$_1$-C$_6$)alkyl optionally substituted with —OH, C$_{3-6}$ cycloalkyl, —NH—C$_{1-3}$ alkyl or —N—(C$_{1-3}$-alkyl)$_2$; or
R$^5$ and R$^6$ together with the nitrogen atom to which they are attached form a 6 membered heterocyclic ring optionally substituted with methyl; and
n is 0 or 2.

In a seventh embodiment, the present invention relates to a compound as described in the broadest embodiment above, or a pharmaceutically acceptable salt thereof, wherein:
HET is pyrazolyl optionally substituted with one to two substituents groups selected from R$^3$ and R$^4$.

In embodiment eight, the present invention relates to a compound as described in the broadest embodiment above, or a pharmaceutically acceptable salt thereof, wherein:
HET is a 5-membered heteroaryl ring selected from pyrazolyl and imidazolyl, wherein each heteroaryl ring is substituted with two substituents groups selected from R$^a$ and R$^b$; wherein
R$^a$ and R$^b$ together with the atoms to which they are attached form a 5-6 membered heteroaryl ring such that HET is a bicyclic heteroaryl ring selected from imidazopyridine and pyrazolopyridine which may be optionally substituted one to two substituents selected from R$^3$ and R$^4$.

In embodiment nine, the present invention relates to a compound as described in the broadest embodiment above, or a pharmaceutically acceptable salt thereof, wherein:
X is N;
Y is CH;
R$^1$ is F;
R$^2$ is selected from methyl and Cl;
HET is selected from imidazopyridine and pyrazolopyridine which may be optionally substituted with one to two substituents selected from R$^3$ and R$^4$;
R$^3$ and R$^4$ are each independently selected from:
(a) —H,
(b) —OR$^5$,
(c) —O—C$_{1-6}$alkyl-O—C$_{1-3}$ alkyl
(d) —O—C$_{3-6}$ cycloalkyl,
(e) —C(O)R$^5$,
(f) C$_{1-6}$alkyl optionally substituted with one to three —OH, fluorine, heterocyclyl optionally substituted with oxo, C$_{3-6}$ cycloalkyl, —CO$_2$R$^5$, —O—C$_{1-6}$alkyl, aryl, —N(R$^5$)(R$^6$), or —C(O)N(R$^5$)(R$^6$),
(g) C$_{3-6}$ cycloalkyl optionally substituted with one to three —OH, one to three fluorine, C$_1$-6alkyl, —OC$_{1-6}$alkyl, C$_{1-6}$alkyl-OC$_{1-6}$alkyl, C$_{1-6}$alkyl-OH, CF$_3$, —OC$_{3-6}$cycloalkyl, —CO$_2$H, —CO$_2$R$^5$, C$_{3-6}$cycloalkyl, 5-6 membered heteroaryl, C$_{3-6}$ heterocyclyl, N(R$^5$)(R$^6$), or —C(O)N(R$^5$)(R$^6$),
(h) —CO$_2$R$^5$,
(i) —C(O)N(R$^5$)(R$^6$),
(j) —S(O)$_2$N(R$^5$)(R$^6$),
(k) —S(O)$_2$—R$^5$
(l) a 5-6 membered heteroaryl group optionally substituted with one to three groups selected from C$_{1-6}$alkyl, C$_{3-6}$cycloalkyl, halogen, —CF$_3$, —OH, —(CH$_2$)

$CO_2R^5$, —C(O)N($R^5$)($R^6$), —N($R^5$)($R^6$), —NH—$SO_2C_{1-6}$alkyl, $C_{1-6}$alkoxyl, $C_{1-6}$alkyl-O—$C_{1-3}$ alkyl, $C_{1-6}$alkylhydroxyl, $C_1$-3alkyl-CN, oxo, phenyl optionally substituted with halogen and —S(O)$_2C_{1-6}$alkyl, (m) 4-10 membered monocyclic, bicyclic or spirocyclic heterocyclyl group containing N, S or O, wherein each heterocycle is optionally substituted with 1-3 substituents selected from 3-6 membered heterocyclic ring, halogen, $C_{1-3}$alkyl, and $C_{1-3}$alkyl-C(O)N($R^5$)($R^6$).

(n) aryl, (o) —N($R^5$)($R^6$);

$R^5$ and $R^6$ are each independently selected from —H, 4-6 membered heterocyclyl, —C(O)—$C_{1-3}$ alkyl —C(O)—$C_{1-3}$ cycloalkyl and —($C_1$-$C_6$)alkyl optionally substituted with —OH, $C_{3-6}$ cycloalkyl, —NH—$C_{1-3}$ alkyl or —N—($C_{1-3}$-alkyl)$_2$; or $R^5$ and $R^6$ together with the nitrogen atom to which they are attached form a 6 membered heterocyclic ring optionally substituted with methyl.

In embodiment ten, the present invention relates to a compound as described in the broadest embodiment above, or a pharmaceutically acceptable salt thereof, wherein:

X is N;
Y is CH;
$R^1$ is F;
$R^2$ is selected from methyl and Cl;
HET is imidazopyridine which may be optionally substituted with one to two substituents selected from $R^3$ and $R^4$;
$R^3$ and $R^4$ are each independently selected from:

(a) —H,
(b) —$OR^5$,
(c) —O—$C_{1-6}$alkyl-O—$C_{1-3}$ alkyl
(d) —O—$C_{3-6}$ cycloalkyl,
(e) —C(O)$R^5$,
(f) $C_{1-6}$alkyl optionally substituted with one to three —OH, fluorine, heterocyclyl optionally substituted with oxo, $C_{3-6}$ cycloalkyl, —$CO_2R^5$, —O—$C_{1-6}$alkyl, aryl, —N($R^5$)($R^6$), or —C(O)N($R^5$)($R^6$),
(g) $C_{3-6}$ cycloalkyl optionally substituted with one to three —OH, one to three fluorine, $C_1$-6alkyl, —$OC_{1-6}$alkyl, $C_{1-6}$alkyl-$OC_{1-6}$alkyl, $C_{1-6}$alkyl-OH, $CF_3$, —$OC_{3-6}$cycloalkyl, —$CO_2H$, —$CO_2R^5$, $C_{3-6}$cycloalkyl, 5-6 membered heteroaryl, $C_{3-6}$ heterocyclyl, N($R^5$)($R^6$), or —C(O)N($R^5$)($R^6$),
(h) —$CO_2R^5$,
(i) —C(O)N($R^5$)($R^6$),
(j) —S(O)$_2$N($R^5$)($R^6$),
(k) —S(O)$_2$—$R^5$
(l) a 5-6 membered heteroaryl group optionally substituted with one to three groups selected from $C_{1-6}$alkyl, $C_{3-6}$cycloalkyl, halogen, —$CF_3$, —OH, —(CH$_2$)$CO_2R^5$, —C(O)N($R^5$)($R^6$), —N($R^5$)($R^6$), —NH—$SO_2C_{1-6}$alkyl, $C_{1-6}$alkoxyl, $C_{1-6}$alkyl-O—$C_{1-3}$ alkyl, $C_{1-6}$alkylhydroxyl, $C_1$-3alkyl-CN, oxo, phenyl optionally substituted with halogen and —S(O)$_2C_{1-6}$alkyl,
(m) 6 membered monocyclic heterocyclyl group containing N wherein the heterocycle is optionally substituted with 1-3 substituents selected from 3-6 membered heterocyclic ring, halogen, $C_{1-3}$alkyl, and $C_{1-3}$alkyl-C(O)N($R^5$)($R^6$).
(n) aryl,
(o) —N($R^5$)($R^6$);

$R^5$ and $R^6$ are each independently selected from —H, 4-6 membered heterocyclyl, —C(O)—$C_{1-3}$ alkyl —C(O)—$C_{1-3}$ cycloalkyl and —($C_1$-$C_6$)alkyl optionally substituted with —OH, $C_{3-6}$ cycloalkyl, —NH—$C_{1-3}$ alkyl or —N—($C_{1-3}$-alkyl)$_2$; or $R^5$ and $R^6$ together with the nitrogen atom to which they are attached form a 6 membered heterocyclic ring optionally substituted with methyl.

In embodiment eleven, the present invention relates to a compound as described in the ninth embodiment above, or a pharmaceutically acceptable salt thereof, wherein:

HET is:

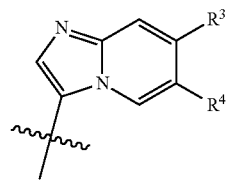

optionally substituted one to two substituents selected from $R^3$ and $R^4$;

$R^3$ and $R^4$ are each independently selected from:

(a) —H,
(b) —$OR^5$,
(c) —O—$C_{1-6}$alkyl-O—$C_{1-3}$ alkyl
(d) —O—$C_{3-6}$ cycloalkyl,
(e) —C(O)$R^5$,
(f) $C_{1-6}$alkyl optionally substituted with one to three —OH, fluorine, heterocyclyl optionally substituted with oxo, $C_{3-6}$ cycloalkyl, —$CO_2R^5$, —O—$C_{1-6}$alkyl, aryl, —N($R^5$)($R^6$), or —C(O)N($R^5$)($R^6$),
(g) $C_{3-6}$ cycloalkyl optionally substituted with one to three —OH, one to three fluorine, $C_1$-6alkyl, —$OC_{1-6}$alkyl, $C_{1-6}$alkyl-$OC_{1-6}$alkyl, $C_{1-6}$alkyl-OH, $CF_3$, —$OC_{3-6}$cycloalkyl, —$CO_2H$, —$CO_2R^5$, $C_{3-6}$cycloalkyl, 5-6 membered heteroaryl, $C_{3-6}$ heterocyclyl, N($R^5$)($R^6$), or —C(O)N($R^5$)($R^6$),
(h) —$CO_2R^5$,
(i) —C(O)N($R^5$)($R^6$),
(j) —S(O)$_2$N($R^5$)($R^6$),
(k) —S(O)$_2$—$R^5$
(l) a 5-6 membered heteroaryl group optionally substituted with one to three groups selected from $C_{1-6}$alkyl, $C_{3-6}$cycloalkyl, halogen, —$CF_3$, —OH, —(CH$_2$)$CO_2R^5$, —C(O)N($R^5$)($R^6$), —N($R^5$)($R^6$), —NH—$SO_2C_{1-6}$alkyl, $C_{1-6}$alkoxyl, $C_{1-6}$alkyl-O—$C_{1-3}$ alkyl, $C_{1-6}$alkylhydroxyl, $C_1$-3alkyl-CN, oxo, phenyl optionally substituted with halogen and —S(O)$_2C_{1-6}$alkyl,
(m) 4-10 membered monocyclic, bicyclic or spirocyclic heterocyclyl group containing N, S or O, wherein each heterocycle is optionally substituted with 1-3 substituents selected from 3-6 membered heterocyclic ring, halogen, $C_{1-3}$alkyl, and $C_{1-3}$alkyl-C(O)N($R^5$)($R^6$).
(n) aryl,
(o) —N($R^5$)($R^6$);

$R^5$ and $R^6$ are each independently selected from —H, 4-6 membered heterocyclyl, —C(O)—$C_{1-3}$ alkyl —C(O)—$C_{1-3}$ cycloalkyl and —($C_1$-$C_6$)alkyl optionally substituted with —OH, $C_{3-6}$ cycloalkyl, —NH—$C_{1-3}$ alkyl or —N—($C_{1-3}$-alkyl)$_2$; or $R^5$ and $R^6$ together with the nitrogen atom to which they are attached form a 6 membered heterocyclic ring optionally substituted with methyl.

In embodiment twelve, the present invention relates to a compound as described in the ninth embodiment above, or a pharmaceutically acceptable salt thereof, wherein:

HET is:

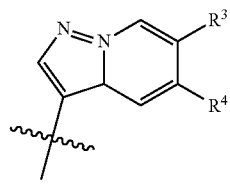

optionally substituted one to two substituents selected from $R^3$ and $R^4$.

In embodiment thirteen, the present invention relates to a compound as described in the broadest embodiment above, or a pharmaceutically acceptable salt thereof, wherein:

HET is:

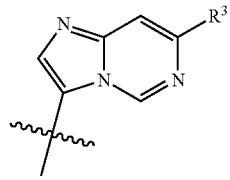

optionally substituted one to two substituents selected from $R^3$ and $R^4$.

In embodiment fourteen, the present invention relates to a compound as described in the broadest embodiment above, or a pharmaceutically acceptable salt thereof, wherein:

HET is:

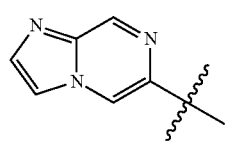 [SMILES: *c1cn2ccnc2cn1]

optionally substituted one to two substituents selected from $R^3$ and $R^4$.

In embodiment fifteen, the present invention relates to a compound as described in the broadest embodiment, or a pharmaceutically acceptable salt thereof, wherein:

HET is selected from:

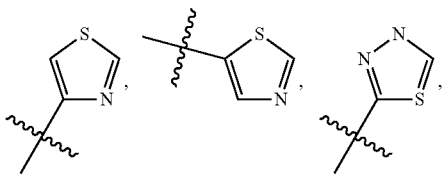

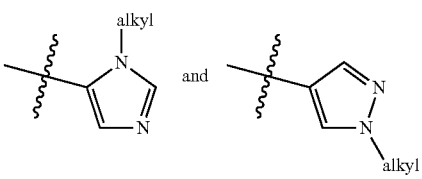

optionally substituted one to two substituents selected from $R^3$ and $R^4$.

In embodiment sixteen, the present invention relates to a compound of formula I or a pharmaceutically acceptable salt thereof, wherein:

X is N;

Y is CH;

$R^1$ is F;

$R^2$ is methyl;

HET is:

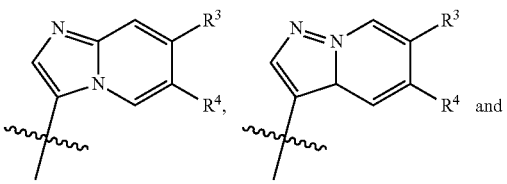

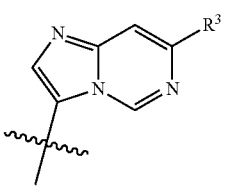

$R^3$ is methoxy; and $R^4$ is

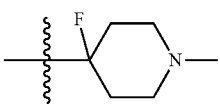

TABLE 1

The following are representative compounds of the invention which can be made by the general synthetic schemes, the examples, and known methods in the art.

| Example | Structure | Structure Name |
|---|---|---|
| 1 | 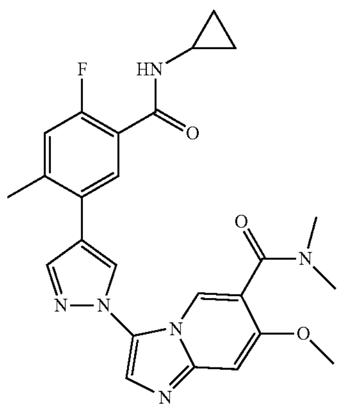 | 3-{4-[5-(cyclopropylcarbamoyl)-4-fluoro-2-methylphenyl]-1H-pyrazol-1-yl}-7-methoxy-N,N-dimethylimidazo[1,2-a]pyridine-6-carboxamide |
| 2 | 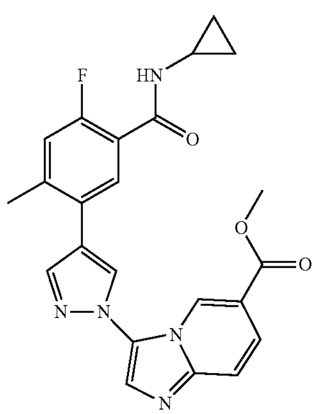 [SMILES: COC(=O)c1ccc2ncc(-n3cc(-c4cc(C(=O)NC5CC5)c(F)cc4C)cn3)n2c1] | methyl 3-{4-[5-(cyclopropylcarbamoyl)-4-fluoro-2-methylphenyl]-1H-pyrazol-1-yl}imidazo[1,2-a]pyridine-6-carboxylate |
| 3 | 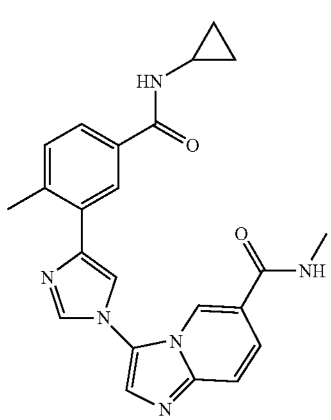 | 3-{4-[5-(cyclopropylcarbamoyl)-2-methylphenyl]-1H-imidazol-1-yl}-N-methylimidazo[1,2-a]pyridine-6-carboxamide |

TABLE 1-continued

The following are representative compounds of the invention which can be made by the general synthetic schemes, the examples, and known methods in the art.

| Example | Structure | Structure Name |
|---|---|---|
| 5 | 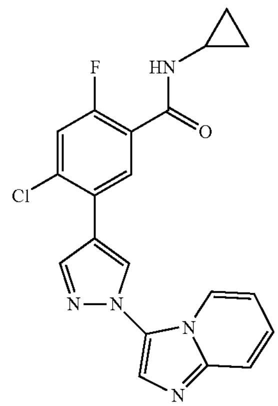 [SMILES: O=C(NC1CC1)c1cc(-c2cnn(-c3cnc4ccccn34)c2)c(Cl)cc1F] | 4-chloro-N-cyclopropyl-2-fluoro-5-(1-{imidazo[1,2-a]pyridin-3-yl}-1H-pyrazol-4-yl)benzamide |
| 6 | 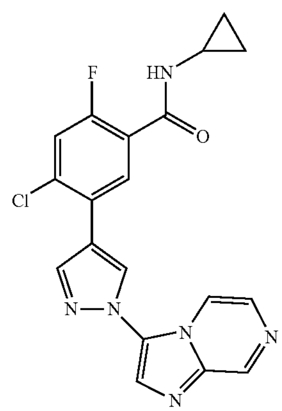 [SMILES: O=C(NC1CC1)c1cc(-c2cnn(-c3cnc4cnccn34)c2)c(Cl)cc1F] | 4-chloro-N-cyclopropyl-2-fluoro-5-(1-{imidazo[1,2-a]pyrazin-3-yl}-1H-pyrazol-4-yl)benzamide |
| 7 | 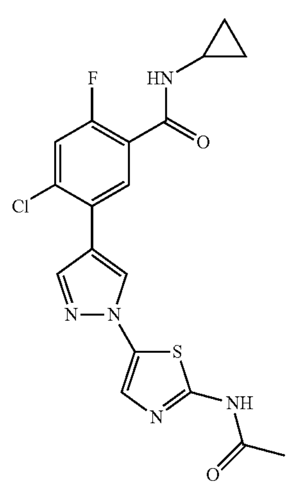 [SMILES: CC(=O)Nc1ncc(-n2cc(-c3cc(C(=O)NC4CC4)c(F)cc3Cl)cn2)s1] | 4-chloro-N-cyclopropyl-5-[1-(2-acetamido-1,3-thiazol-5-yl)-1H-pyrazol-4-yl]-2-fluorobenzamide |

TABLE 1-continued

The following are representative compounds of the invention which can be made by the general synthetic schemes, the examples, and known methods in the art.

| Example | Structure | Structure Name |
|---|---|---|
| 8 | 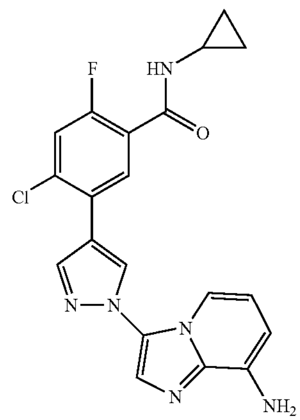 [SMILES: Nc1cccn2c(-n3cc(-c4cc(C(=O)NC5CC5)c(F)cc4Cl)cn3)cnc12] | 5-(1-{8-aminoimidazo[1,2-a]pyridin-3-yl}-1H-pyrazol-4-yl)-4-chloro-N-cyclopropyl-2-fluorobenzamide |
| 9 | 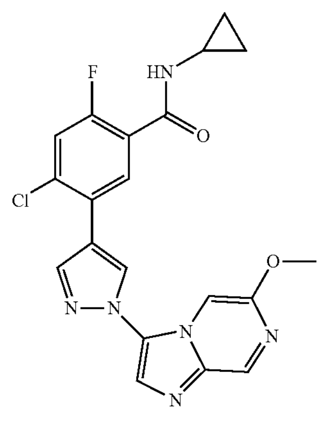 [SMILES: COc1cn2c(-n3cc(-c4cc(C(=O)NC5CC5)c(F)cc4Cl)cn3)cnc2cn1] | 4-chloro-N-cyclopropyl-2-fluoro-5-(1-{6-methoxyimidazo[1,2-a]pyrazin-3-yl}-1H-pyrazol-4-yl)benzamide |
| 10 | 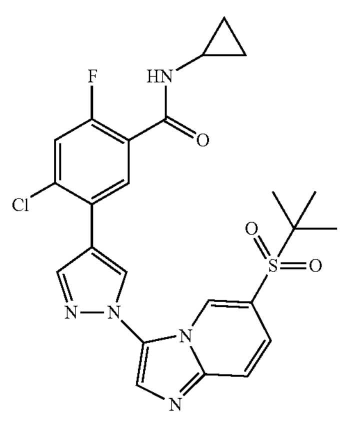 [SMILES: CC(C)(C)S(=O)(=O)c1ccc2ncc(-n3cc(-c4cc(C(=O)NC5CC5)c(F)cc4Cl)cn3)n2c1] | 4-chloro-N-cyclopropyl-2-fluoro-5-{1-[6-(2-methylpropane-2-sulfonyl)imidazo[1,2-a]pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 11 | 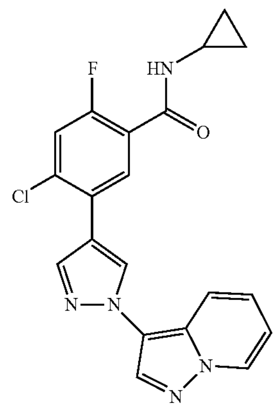 [SMILES: O=C(NC1CC1)c1cc(-c2cnn(-c3cnn4ccccc34)c2)c(Cl)cc1F] | 4-chloro-N-cyclopropyl-2-fluoro-5-(1-{pyrazolo[1,5-a]pyridin-3-yl}-1H-pyrazol-4-yl)benzamide |
| 12 | 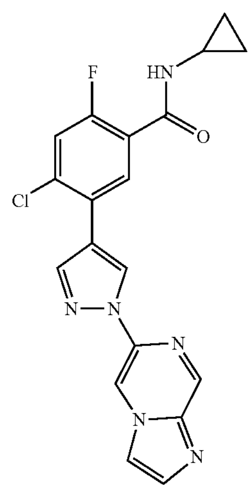 [SMILES: O=C(NC1CC1)c1cc(-c2cnn(-c3cn4ccnc4cn3)c2)c(Cl)cc1F] | 4-chloro-N-cyclopropyl-2-fluoro-5-(1-{imidazo[1,2-a]pyrazin-6-yl}-1H-pyrazol-4-yl)benzamide |
| 13 | 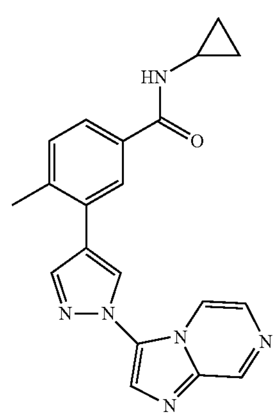 [SMILES: Cc1ccc(C(=O)NC2CC2)cc1-c1cnn(-c2cnc3cnccn23)c1] | N-cyclopropyl-3-(1-{imidazo[1,2-a]pyrazin-3-yl}-1H-pyrazol-4-yl)-4-methylbenzamide |

TABLE 1-continued

The following are representative compounds of the invention which can be made by the general synthetic schemes, the examples, and known methods in the art.

| Example | Structure | Structure Name |
|---|---|---|
| 14 | 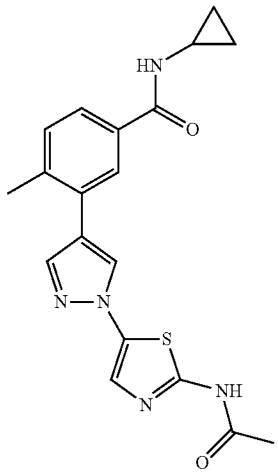 [SMILES: CC(=O)Nc1ncc(-n2cc(-c3cc(C(=O)NC4CC4)ccc3C)cn2)s1] | N-cyclopropyl-3-[1-(2-acetamido-1,3-thiazol-5-yl)-1H-pyrazol-4-yl]-4-methylbenzamide |
| 15 | 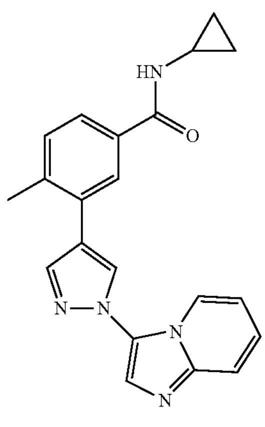 [SMILES: Cc1ccc(C(=O)NC2CC2)cc1-c1cnn(-c2cnc3ccccn23)c1] | N-cyclopropyl-3-(1-{imidazo[1,2-a]pyridin-3-yl}-1H-pyrazol-4-yl)-4-methylbenzamide |
| 16 | 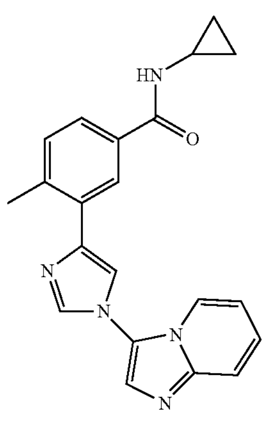 [SMILES: Cc1ccc(C(=O)NC2CC2)cc1-c1cn(-c2cnc3ccccn23)cn1] | N-cyclopropyl-3-(1-{imidazo[1,2-a]pyridin-3-yl}-1H-imidazol-4-yl)-4-methylbenzamide |

TABLE 1-continued

The following are representative compounds of the invention which can be made by the general synthetic schemes, the examples, and known methods in the art.

| Example | Structure | Structure Name |
|---------|-----------|----------------|
| 17 | 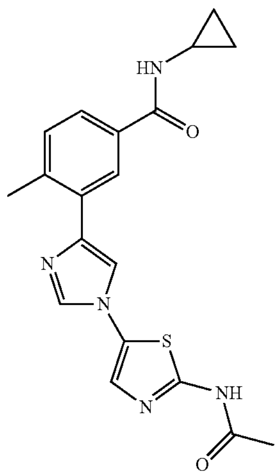 [SMILES: CC(=O)Nc1ncc(-n2cnc(-c3cc(C(=O)NC4CC4)ccc3C)c2)s1] | N-cyclopropyl-3-[1-(2-acetamido-1,3-thiazol-5-yl)-1H-imidazol-4-yl]-4-methylbenzamide |
| 19 | 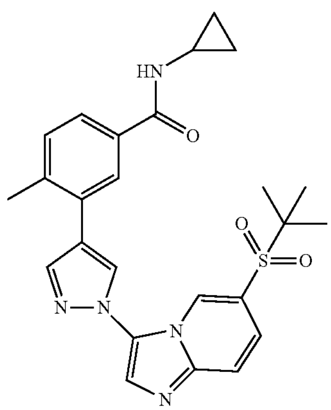 [SMILES: Cc1ccc(C(=O)NC2CC2)cc1-c1cnn(-c2cnc3ccc(S(=O)(=O)C(C)(C)C)cn23)c1] | N-cyclopropyl-4-methyl-3-{1-[6-(2-methylpropane-2-sulfonyl)imidazo[1,2-a]pyridin-3-yl]-1H-pyrazol-4-yl}benzamide |
| 20 | 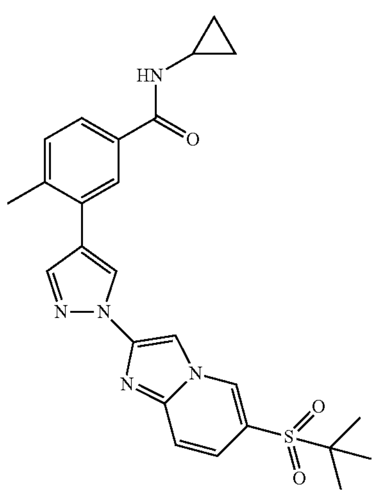 [SMILES: Cc1ccc(C(=O)NC2CC2)cc1-c1cnn(-c2cn3cc(S(=O)(=O)C(C)(C)C)ccc3n2)c1] | N-cyclopropyl-4-methyl-3-{1-[6-(2-methylpropane-2-sulfonyl)imidazo[1,2-a]pyridin-2-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 21 | 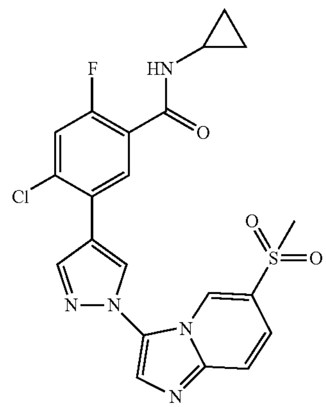 [SMILES: CS(=O)(=O)c1ccc2ncc(-n3cc(-c4cc(C(=O)NC5CC5)c(F)cc4Cl)cn3)n2c1] | 4-chloro-N-cyclopropyl-2-fluoro-5-(1-{6-methanesulfonylimidazo[1,2-a]pyridin-3-yl}-1H-pyrazol-4-yl)benzamide |
| 22 | 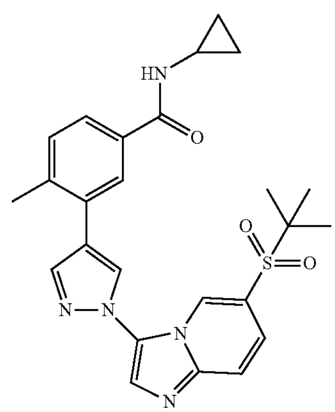 [SMILES: Cc1ccc(C(=O)NC2CC2)cc1-c1cnn(-c2cnc3ccc(S(=O)(=O)C(C)(C)C)cn23)c1] | N-cyclopropyl-4-methyl-3-{1-[6-(2-methylpropane-2-sulfonyl)imidazo[1,2-a]pyridin-3-yl]-1H-imidazol-4-yl}benzamide |
| 23 | 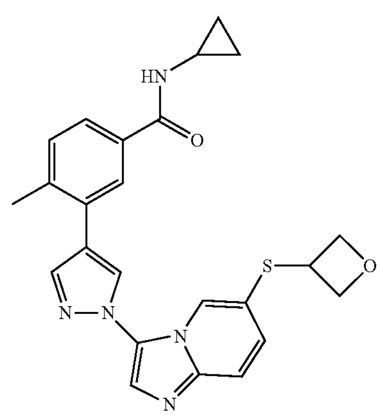 [SMILES: Cc1ccc(C(=O)NC2CC2)cc1-c1cnn(-c2cnc3ccc(SC4COC4)cn23)c1] | N-cyclopropyl-4-methyl-3-{1-[6-(oxetan-3-ylsulfanyl)imidazo[1,2-a]pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---------|-----------|----------------|
| 25 | 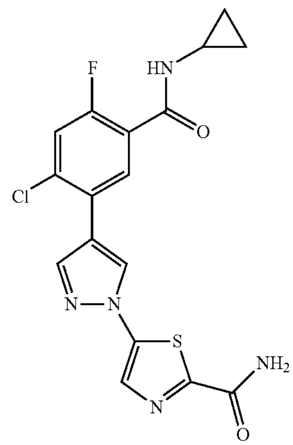 [SMILES: NC(=O)c1ncc(-n2cc(-c3cc(C(=O)NC4CC4)c(F)cc3Cl)cn2)s1] | 5-{4-[2-chloro-5-(cyclopropylcarbamoyl)-4-fluorophenyl]-1H-pyrazol-1-yl}-1,3-thiazole-2-carboxamide |
| 26 | 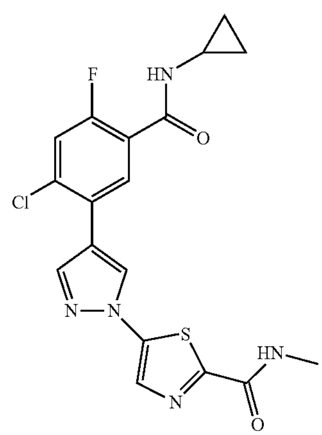 [SMILES: CNC(=O)c1ncc(-n2cc(-c3cc(C(=O)NC4CC4)c(F)cc3Cl)cn2)s1] | 5-{4-[2-chloro-5-(cyclopropylcarbamoyl)-4-fluorophenyl]-1H-pyrazol-1-yl}-N-methyl-1,3-thiazole-2-carboxamide |
| 27 | 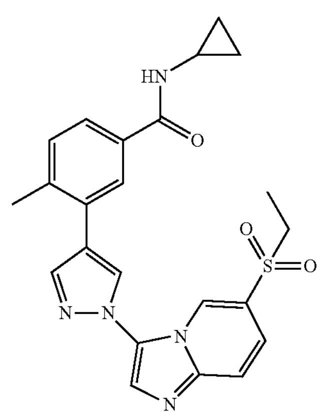 [SMILES: CCS(=O)(=O)c1ccc2ncc(-n3cc(-c4cc(C(=O)NC5CC5)ccc4C)cn3)n2c1] | N-cyclopropyl-3-{1-[6-(ethanesulfonyl)imidazo[1,2-a]pyridin-3-yl]-1H-pyrazol-4-yl}-4-methylbenzamide |

TABLE 1-continued

The following are representative compounds of the invention which can be made by the general synthetic schemes, the examples, and known methods in the art.

| Example | Structure | Structure Name |
|---|---|---|
| 28 | 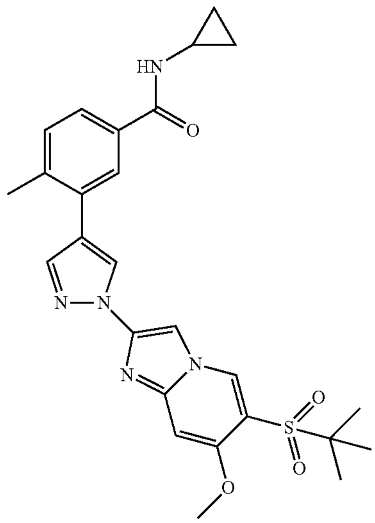 [SMILES: COc1cc2nc(-n3cc(-c4cc(C(=O)NC5CC5)ccc4C)cn3)cn2cc1S(=O)(=O)C(C)(C)C] | N-cyclopropyl-3-{1-[7-methoxy-6-(2-methylpropane-2-sulfonyl)imidazo[1,2-a]pyridin-2-yl]-1H-pyrazol-4-yl}-4-methylbenzamide |
| 29 | 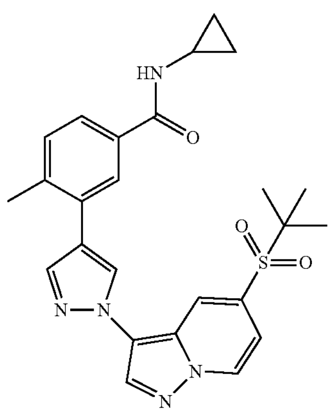 [SMILES: Cc1ccc(C(=O)NC2CC2)cc1-c1cnn(-c2cnn3ccc(S(=O)(=O)C(C)(C)C)cc23)c1] | N-cyclopropyl-4-methyl-3-{1-[5-(2-methylpropane-2-sulfonyl)pyrazolo[1,5-a]pyridin-3-yl]-1H-pyrazol-4-yl}benzamide |
| 30 | 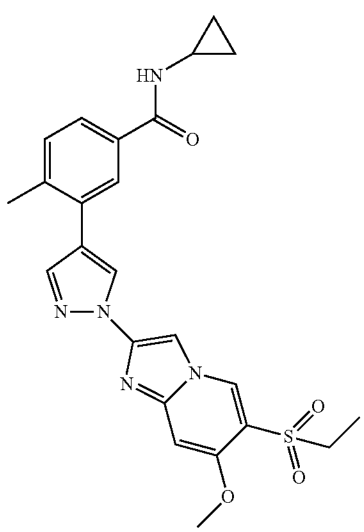 [SMILES: CCS(=O)(=O)c1cn2cc(-n3cc(-c4cc(C(=O)NC5CC5)ccc4C)cn3)nc2cc1OC] | N-cyclopropyl-3-{1-[6-(ethanesulfonyl)-7-methoxyimidazo[1,2-a]pyridin-2-yl]-1H-pyrazol-4-yl}-4-methylbenzamide |

TABLE 1-continued

The following are representative compounds of the invention which can be made by the general synthetic schemes, the examples, and known methods in the art.

| Example | Structure | Structure Name |
|---|---|---|
| 31 | 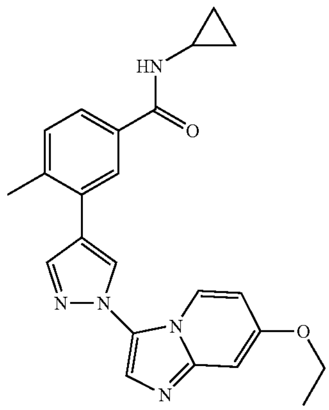 [SMILES: CCOc1ccn2c(-n3cc(-c4cc(C(=O)NC5CC5)ccc4C)cn3)cnc2c1] | N-cyclopropyl-3-(1-{7-ethoxyimidazo[1,2-a]pyridin-3-yl}-1H-pyrazol-4-yl)-4-methylbenzamide |
| 32 | 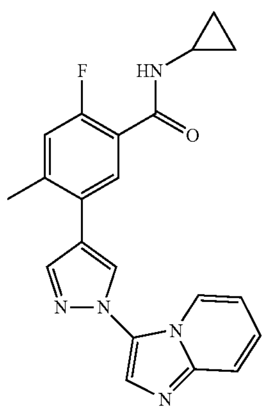 [SMILES: Cc1cc(F)c(C(=O)NC2CC2)cc1-c1cnn(-c2cnc3ccccn23)c1] | N-cyclopropyl-2-fluoro-5-(1-{imidazo[1,2-a]pyridin-3-yl}-1H-pyrazol-4-yl)-4-methylbenzamide |
| 33 | 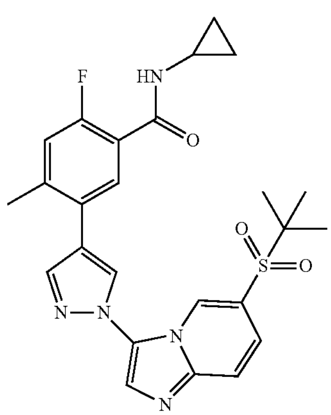 [SMILES: Cc1cc(F)c(C(=O)NC2CC2)cc1-c1cnn(-c2cnc3ccc(S(=O)(=O)C(C)(C)C)cn23)c1] | N-cyclopropyl-2-fluoro-4-methyl-5-{1-[6-(2-methylpropane-2-sulfonyl)imidazo[1,2-a]pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 34 | 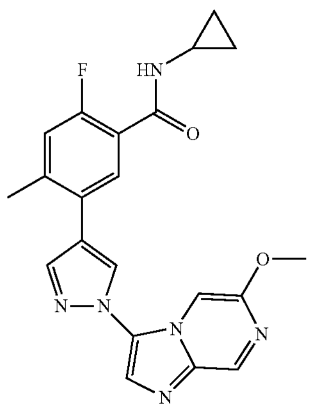 | N-cyclopropyl-2-fluoro-5-(1-{6-methoxyimidazo[1,2-a]pyrazin-3-yl}-1H-pyrazol-4-yl)-4-methylbenzamide |
| 35 | 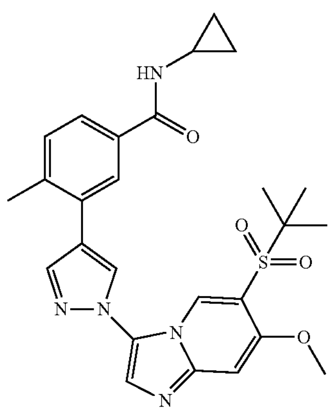 [SMILES: COc1cc2ncc(-n3cc(-c4cc(C(=O)NC5CC5)ccc4C)cn3)n2cc1S(=O)(=O)C(C)(C)C] | N-cyclopropyl-3-{1-[7-methoxy-6-(2-methylpropane-2-sulfonyl)imidazo[1,2-a]pyridin-3-yl]-1H-pyrazol-4-yl}-4-methylbenzamide |
| 36 | 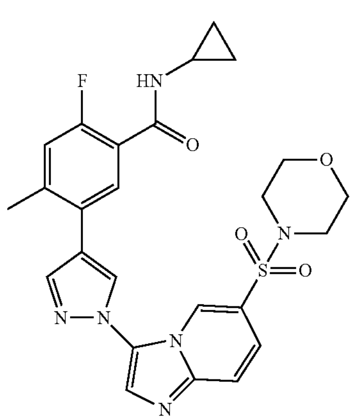 [SMILES: Cc1cc(F)c(C(=O)NC2CC2)cc1-c1cnn(-c2cnc3ccc(S(=O)(=O)N4CCOCC4)cn23)c1] | N-cyclopropyl-2-fluoro-4-methyl-5-{1-[6-(morpholine-4-sulfonyl)imidazo[1,2-a]pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 37 | 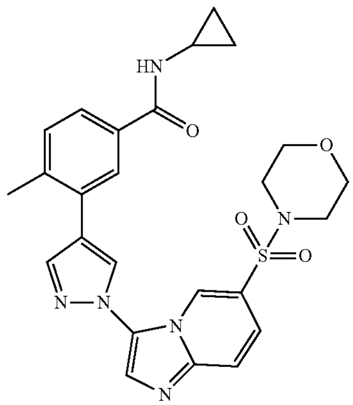 [SMILES: Cc1ccc(C(=O)NC2CC2)cc1-c1cnn(-c2cnc3ccc(S(=O)(=O)N4CCOCC4)cn23)c1] | N-cyclopropyl-4-methyl-3-{1-[6-(morpholine-4-sulfonyl)imidazo[1,2-a]pyridin-3-yl]-1H-pyrazol-4-yl}benzamide |
| 38 | 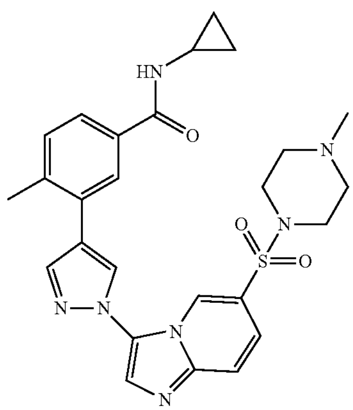 | N-cyclopropyl-4-methyl-3-(1-{6-[(4-methylpiperazin-1-yl)sulfonyl]imidazo[1,2-a]pyridin-3-yl}-1H-pyrazol-4-yl)benzamide |
| 39 | 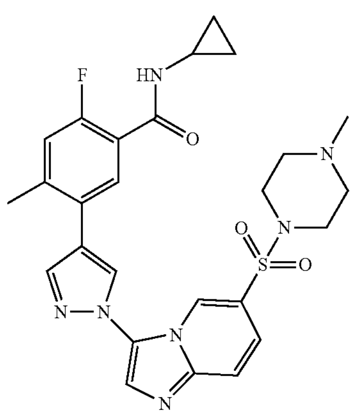 | N-cyclopropyl-2-fluoro-4-methyl-5-(1-{6-[(4-methylpiperazin-1-yl)sulfonyl]imidazo[1,2-a]pyridin-3-yl}-1H-pyrazol-4-yl)benzamide |

TABLE 1-continued

The following are representative compounds of the invention which can be made by the general synthetic schemes, the examples, and known methods in the art.

| Example | Structure | Structure Name |
|---|---|---|
| 40 | 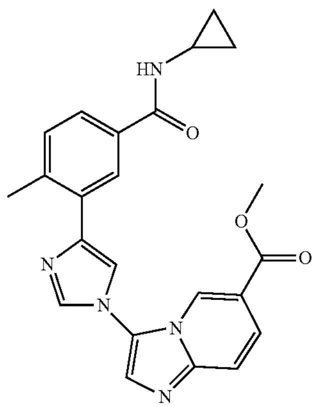 [SMILES: COC(=O)c1ccc2ncc(-n3cnc(-c4cc(C(=O)NC5CC5)ccc4C)c3)n2c1] | methyl 3-{4-[5-(cyclopropylcarbamoyl)-2-methylphenyl]-1H-imidazol-1-yl}imidazo[1,2-a]pyridine-6-carboxylate |
| 41 | 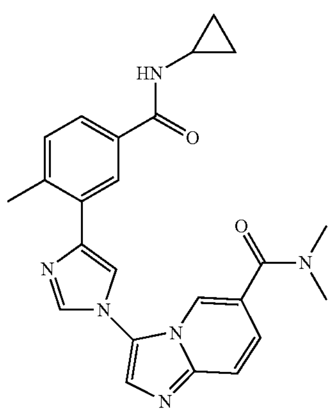 | 3-{4-[5-(cyclopropylcarbamoyl)-2-methylphenyl]-1H-imidazol-1-yl}-N,N-dimethylimidazo[1,2-a]pyridine-6-carboxamide |
| 42 | 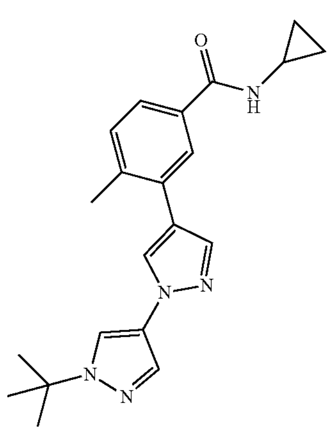 [SMILES: Cc1ccc(C(=O)NC2CC2)cc1-c1cnn(-c2cnn(C(C)(C)C)c2)c1] | 3-[1-(1-tert-butyl-1H-pyrazol-4-yl)-1H-pyrazol-4-yl]-N-cyclopropyl-4-methylbenzamide |

TABLE 1-continued

The following are representative compounds of the invention which can be made by the general synthetic schemes, the examples, and known methods in the art.

| Example | Structure | Structure Name |
|---|---|---|
| 43 | 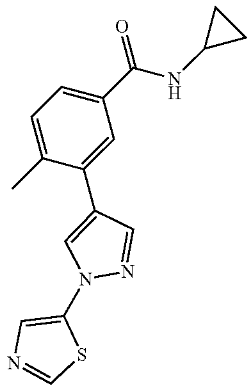 [SMILES: Cc1ccc(C(=O)NC2CC2)cc1-c1cnn(-c2cncs2)c1] | N-cyclopropyl-4-methyl-3-[1-(1,3-thiazol-5-yl)-1H-pyrazol-4-yl]benzamide |
| 44 | 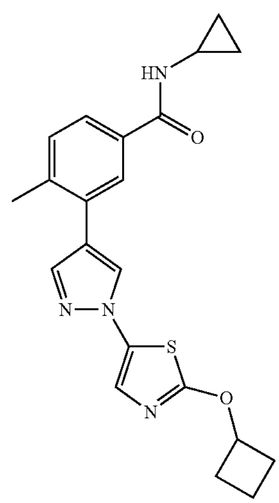 [SMILES: Cc1ccc(C(=O)NC2CC2)cc1-c1cnn(-c2cnc(OC3CCC3)s2)c1] | 3-[1-(2-cyclobutoxy-1,3-thiazol-5-yl)-1H-pyrazol-4-yl]-N-cyclopropyl-4-methylbenzamide |
| 45 | 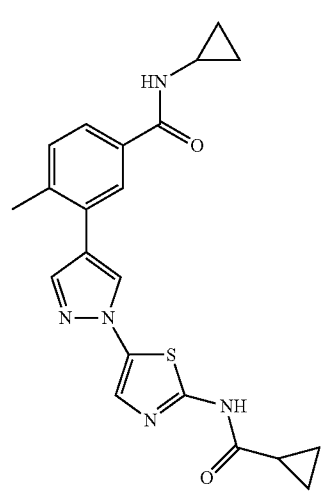 [SMILES: Cc1ccc(C(=O)NC2CC2)cc1-c1cnn(-c2cnc(NC(=O)C3CC3)s2)c1] | 3-[1-(2-cyclopropaneamido-1,3-thiazol-5-yl)-1H-pyrazol-4-yl]-N-cyclopropyl-4-methylbenzamide |

TABLE 1-continued

The following are representative compounds of the invention which can be made by the general synthetic schemes, the examples, and known methods in the art.

| Example | Structure | Structure Name |
|---|---|---|
| 46 | 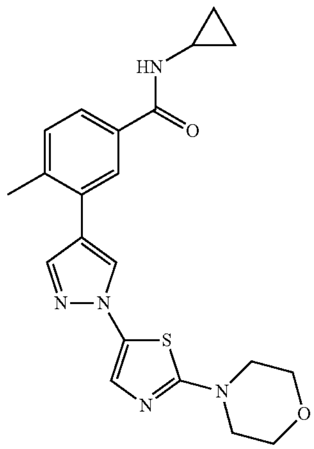 [SMILES: Cc1ccc(C(=O)NC2CC2)cc1-c1cnn(-c2cnc(N3CCOCC3)s2)c1] | N-cyclopropyl-4-methyl-3-{1-[2-(morpholin-4-yl)-1,3-thiazol-5-yl]-1H-pyrazol-4-yl}benzamide |
| 47 | 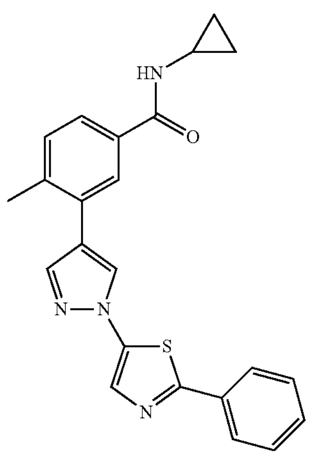 [SMILES: Cc1ccc(C(=O)NC2CC2)cc1-c1cnn(-c2cnc(-c3ccccc3)s2)c1] | N-cyclopropyl-4-methyl-3-[1-(2-phenyl-1,3-thiazol-5-yl)-1H-pyrazol-4-yl]benzamide |
| 48 | 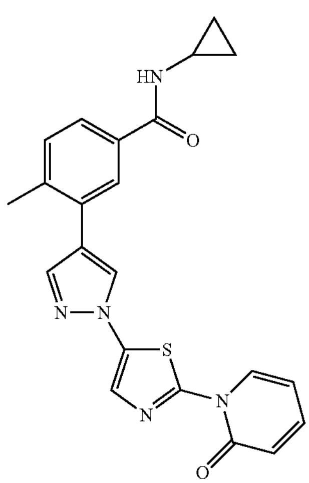 [SMILES: Cc1ccc(C(=O)NC2CC2)cc1-c1cnn(-c2cnc(-n3ccccc3=O)s2)c1] | N-cyclopropyl-4-methyl-3-{1-[2-(2-oxo-1,2-dihydropyridin-1-yl)-1,3-thiazol-5-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---------|-----------|----------------|
| 49 | 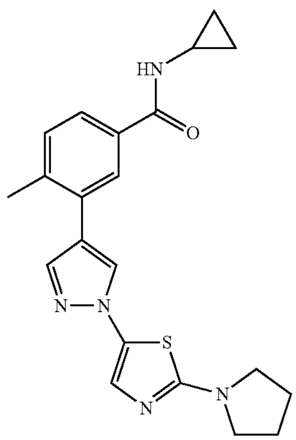 [SMILES: Cc1ccc(C(=O)NC2CC2)cc1-c1cnn(-c2cnc(N3CCCC3)s2)c1] | N-cyclopropyl-4-methyl-3-{1-[2-(pyrrolidin-1-yl)-1,3-thiazol-5-yl]-1H-pyrazol-4-yl}benzamide |
| 50 | 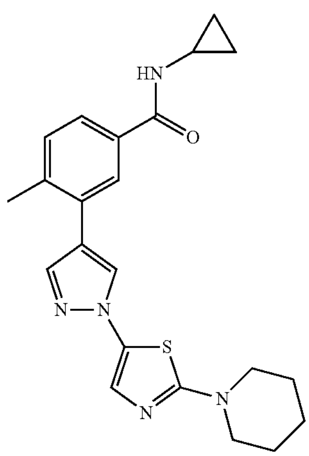 [SMILES: Cc1ccc(C(=O)NC2CC2)cc1-c1cnn(-c2cnc(N3CCCCC3)s2)c1] | N-cyclopropyl-4-methyl-3-{1-[2-(piperidin-1-yl)-1,3-thiazol-5-yl]-1H-pyrazol-4-yl}benzamide |
| 53 | 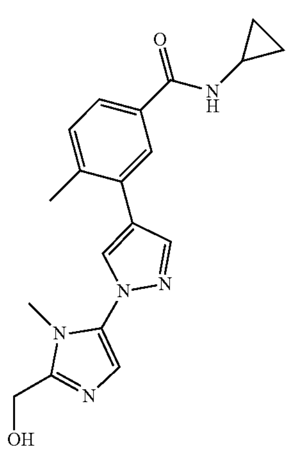 [SMILES: Cc1ccc(C(=O)NC2CC2)cc1-c1cnn(-c2cnc(CO)n2C)c1] | N-cyclopropyl-3-{1-[2-(hydroxymethyl)-1-methyl-1H-imidazol-5-yl]-1H-pyrazol-4-yl}-4-methylbenzamide |

TABLE 1-continued

The following are representative compounds of the invention which can be made by the general synthetic schemes, the examples, and known methods in the art.

| Example | Structure | Structure Name |
|---|---|---|
| 54 | 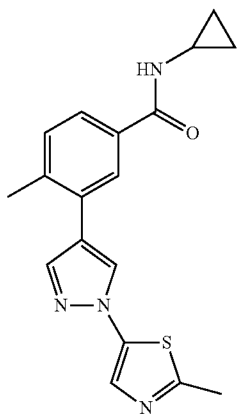 [SMILES: Cc1ncc(-n2cc(-c3cc(C(=O)NC4CC4)ccc3C)cn2)s1] | N-cyclopropyl-4-methyl-3-[1-(5-methyl-1,3,4-thiadiazol-2-yl)-1H-pyrazol-4-yl]benzamide |
| 55 | 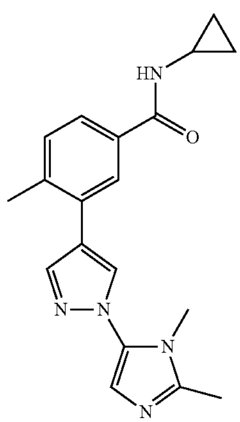 [SMILES: Cc1ccc(C(=O)NC2CC2)cc1-c1cnn(-c2cnc(C)n2C)c1] | N-cyclopropyl-3-[1-(1,2-dimethyl-1H-imidazol-5-yl)-1H-pyrazol-4-yl]-4-methylbenzamide |
| 56 | 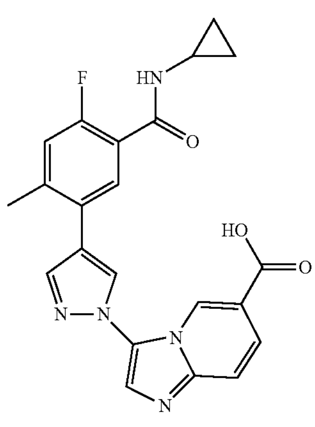 [SMILES: Cc1cc(F)c(C(=O)NC2CC2)cc1-c1cnn(-c2cnc3ccc(C(=O)O)cn23)c1] | 3-{4-[5-(cyclopropylcarbamoyl)-4-fluoro-2-methylphenyl]-1H-pyrazol-1-yl}imidazo[1,2-a]pyridine-6-carboxylic acid |

TABLE 1-continued

The following are representative compounds of the invention which can be made by the general synthetic schemes, the examples, and known methods in the art.

| Example | Structure | Structure Name |
|---|---|---|
| 57 | 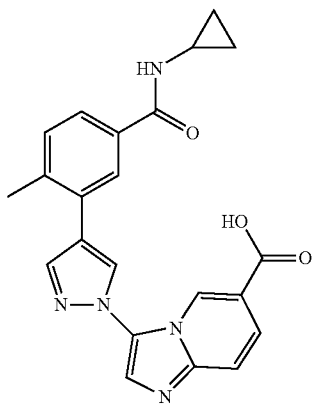 [SMILES: Cc1ccc(C(=O)NC2CC2)cc1-c1cnn(-c2cnc3ccc(C(=O)O)cn23)c1] | 3-{4-[5-(cyclopropylcarbamoyl)-2-methylphenyl]-1H-pyrazol-1-yl}imidazo[1,2-a]pyridine-6-carboxylic acid |
| 58 | 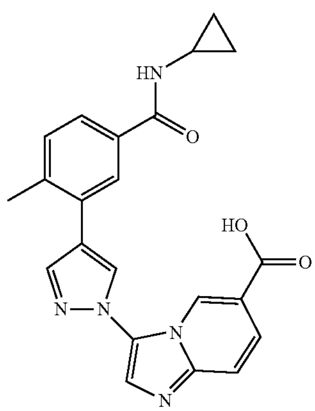 [SMILES: Cc1ccc(C(=O)NC2CC2)cc1-c1cnn(-c2cnc3ccc(C(=O)O)cn23)c1] | 3-{4-[5-(cyclopropylcarbamoyl)-2-methylphenyl]-1H-imidazol-1-yl}imidazo[1,2-a]pyridine-6-carboxylic acid |
| 59 | 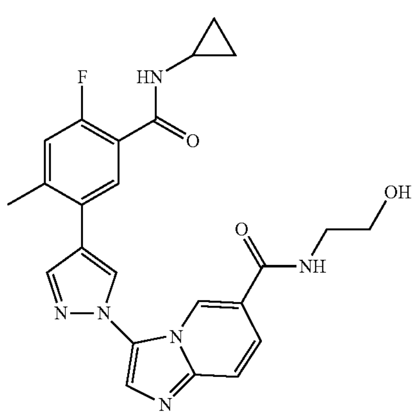 [SMILES: Cc1cc(F)c(C(=O)NC2CC2)cc1-c1cnn(-c2cnc3ccc(C(=O)NCCO)cn23)c1] | 3-{4-[5-(cyclopropylcarbamoyl)-4-fluoro-2-methylphenyl]-1H-pyrazol-1-yl}-N-(2-hydroxyethyl)imidazo[1,2-a]pyridine-6-carboxamide |

TABLE 1-continued

The following are representative compounds of the invention which can be made by the general synthetic schemes, the examples, and known methods in the art.

| Example | Structure | Structure Name |
|---|---|---|
| 60 | 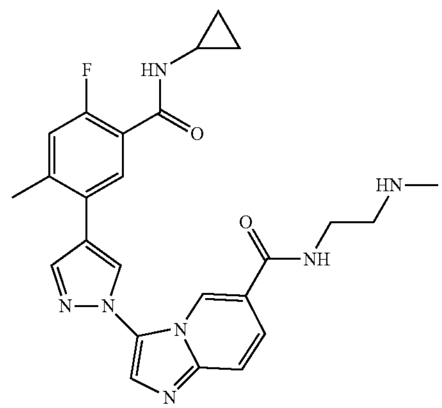 | 3-{4-[5-(cyclopropylcarbamoyl)-4-fluoro-2-methylphenyl]-1H-pyrazol-1-yl}-N-[2-(methylamino)ethyl]imidazo[1,2-a]pyridine-6-carboxamide |
| 61 | 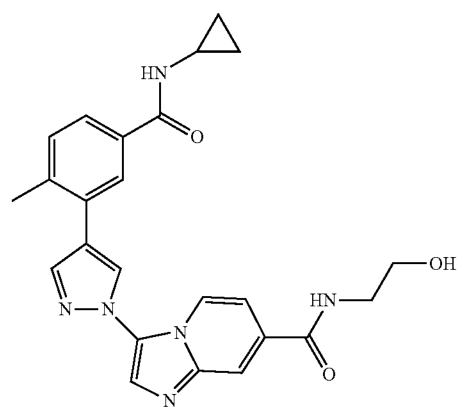 [SMILES: Cc1ccc(C(=O)NC2CC2)cc1-c1cnn(-c2cnc3cc(C(=O)NCCO)ccn23)c1] | 3-{4-[5-(cyclopropylcarbamoyl)-2-methylphenyl]-1H-pyrazol-1-yl}-N-(2-hydroxyethyl)imidazo[1,2-a]pyridine-7-carboxamide |
| 62 | 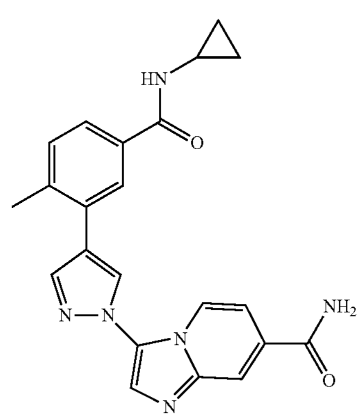 [SMILES: Cc1ccc(C(=O)NC2CC2)cc1-c1cnn(-c2cnc3cc(C(N)=O)ccn23)c1] | 3-{4-[5-(cyclopropylcarbamoyl)-2-methylphenyl]-1H-pyrazol-1-yl}imidazo[1,2-a]pyridine-7-carboxamide |

TABLE 1-continued

The following are representative compounds of the invention which can be made by the general synthetic schemes, the examples, and known methods in the art.

| Example | Structure | Structure Name |
|---|---|---|
| 63 | 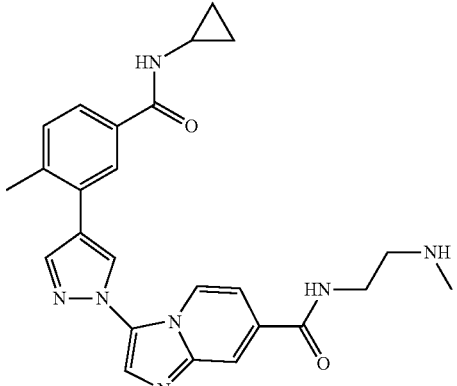 | 3-{4-[5-(cyclopropylcarbamoyl)-2-methylphenyl]-1H-pyrazol-1-yl}-N-[2-(methylamino)ethyl]imidazo[1,2-a]pyridine-7-carboxamide |
| 64 | 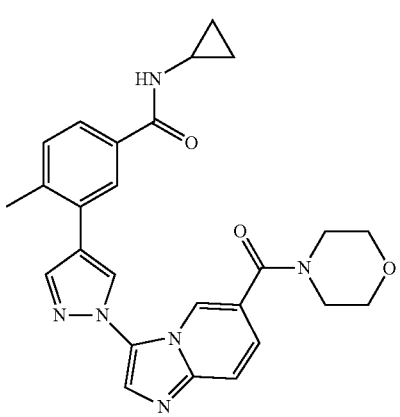 [SMILES: Cc1ccc(C(=O)NC2CC2)cc1-c1cnn(-c2cnc3ccc(C(=O)N4CCOCC4)cn23)c1] | N-cyclopropyl-4-methyl-3-{1-[6-(morpholine-4-carbonyl)imidazo[1,2-a]pyridin-3-yl]-1H-pyrazol-4-yl}benzamide |
| 65 | 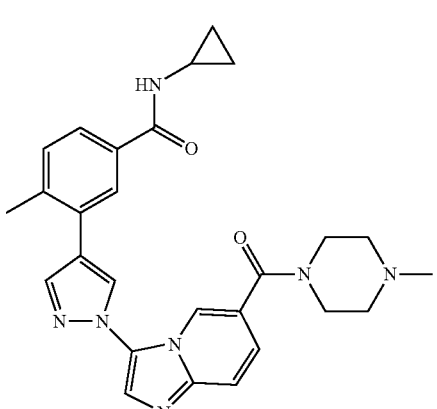 | N-cyclopropyl-4-methyl-3-{1-[6-(4-methylpiperazine-1-carbonyl)imidazo[1,2-a]pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 66 | 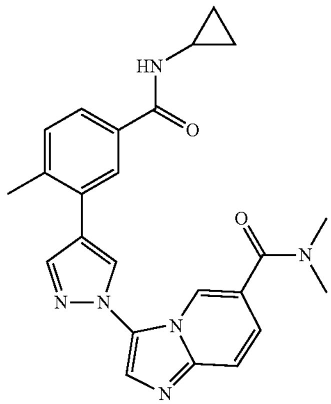 | 3-{4-[5-(cyclopropylcarbamoyl)-2-methylphenyl]-1H-pyrazol-1-yl}-N,N-dimethylimidazo[1,2-a]pyridine-6-carboxamide |
| 67 | 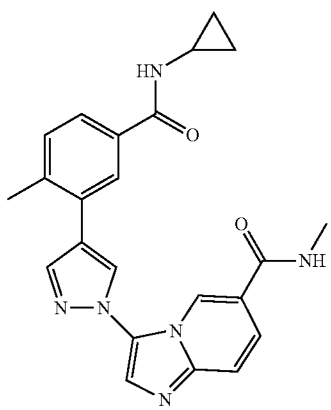 | 3-{4-[5-(cyclopropylcarbamoyl)-2-methylphenyl]-1H-pyrazol-1-yl}-N-methylimidazo[1,2-a]pyridine-6-carboxamide |
| 68 | 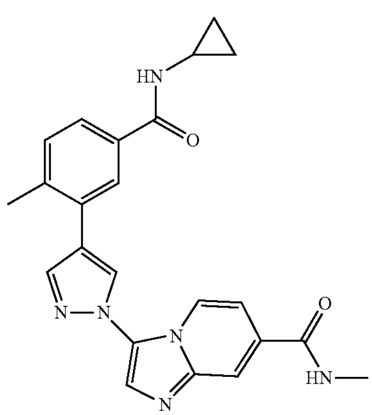 | 3-{4-[5-(cyclopropylcarbamoyl)-2-methylphenyl]-1H-pyrazol-1-yl}-N-methylimidazo[1,2-a]pyridine-7-carboxamide |

TABLE 1-continued

The following are representative compounds of the invention which can be made by the general synthetic schemes, the examples, and known methods in the art.

| Example | Structure | Structure Name |
|---|---|---|
| 69 | 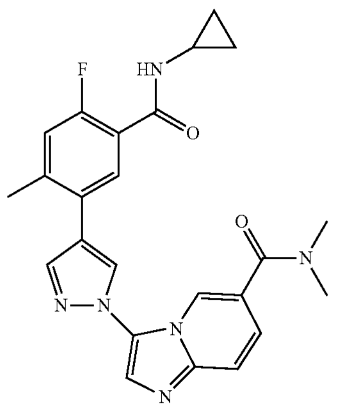 | 3-{4-[5-(cyclopropylcarbamoyl)-4-fluoro-2-methylphenyl]-1H-pyrazol-1-yl}-N,N-dimethylimidazo[1,2-a]pyridine-6-carboxamide |
| 70 | 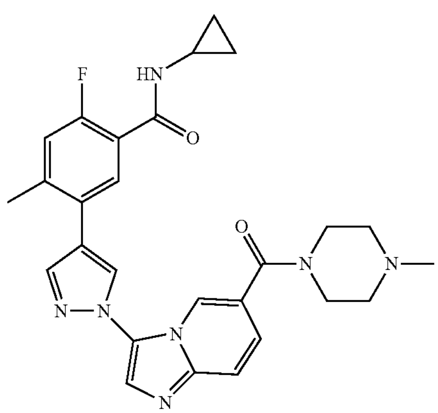 | N-cyclopropyl-2-fluoro-4-methyl-5-{1-[6-(4-methylpiperazine-1-carbonyl)imidazo[1,2-a]pyridin-3-yl]-1H-pyrazol-4-yl}benzamide |
| 71 | 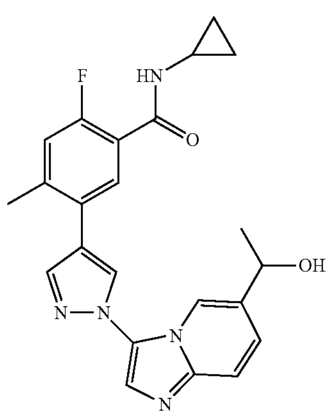 [SMILES: Cc1cc(F)c(C(=O)NC2CC2)cc1-c1cnn(-c2cnc3ccc(C(C)O)cn23)c1] | N-cyclopropyl-2-fluoro-5-{1-[6-(1-hydroxyethyl)imidazo[1,2-a]pyridin-3-yl]-1H-pyrazol-4-yl}-4-methylbenzamide |

TABLE 1-continued

The following are representative compounds of the invention which can be made by the general synthetic schemes, the examples, and known methods in the art.

| Example | Structure | Structure Name |
|---|---|---|
| 72 | 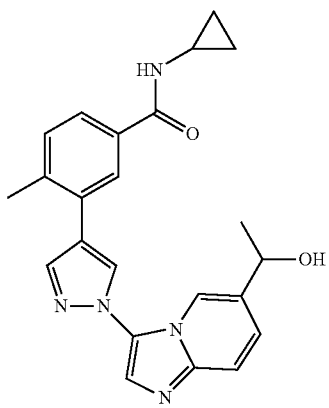 [SMILES: Cc1ccc(C(=O)NC2CC2)cc1-c1cnn(-c2cnc3ccc(C(C)O)cn23)c1] | N-cyclopropyl-3-{1-[6-(1-hydroxyethyl)imidazo[1,2-a]pyridin-3-yl]-1H-pyrazol-4-yl}-4-methylbenzamide |
| 73 | 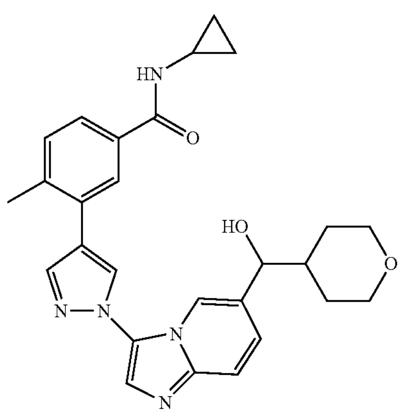 [SMILES: Cc1ccc(C(=O)NC2CC2)cc1-c1cnn(-c2cnc3ccc(C(O)C4CCOCC4)cn23)c1] | N-cyclopropyl-3-(1-{6-[hydroxy(oxan-4-yl)methyl]imidazo[1,2-a]pyridin-3-yl}-1H-pyrazol-4-yl)-4-methylbenzamide |
| 74 | 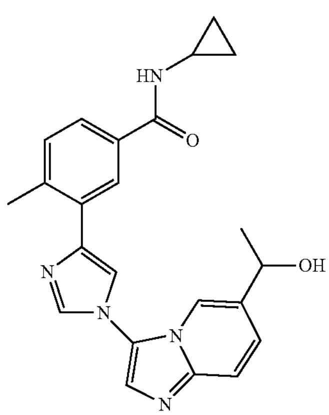 [SMILES: Cc1ccc(C(=O)NC2CC2)cc1-c1cn(-c2cnc3ccc(C(C)O)cn23)cn1] | N-cyclopropyl-3-{1-[6-(1-hydroxyethyl)imidazo[1,2-a]pyridin-3-yl]-1H-imidazol-4-yl}-4-methylbenzamide |

TABLE 1-continued

The following are representative compounds of the invention which can be made by the general synthetic schemes, the examples, and known methods in the art.

| Example | Structure | Structure Name |
|---|---|---|
| 75 | 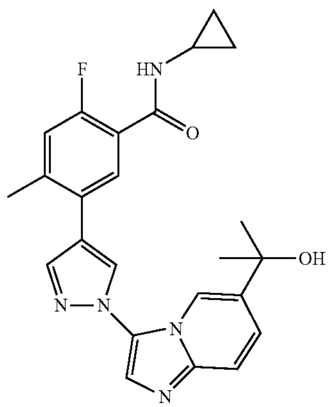 [SMILES: Cc1cc(F)c(C(=O)NC2CC2)cc1-c1cnn(-c2cnc3ccc(C(C)(C)O)cn23)c1] | N-cyclopropyl-2-fluoro-5-{1-[6-(2-hydroxypropan-2-yl)imidazo[1,2-a]pyridin-3-yl]-1H-pyrazol-4-yl}-4-methylbenzamide |
| 76 | 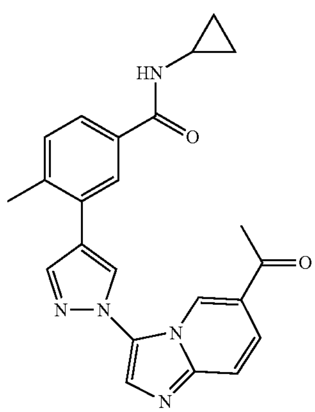 [SMILES: CC(=O)c1ccc2ncc(-n3cc(-c4cc(C(=O)NC5CC5)ccc4C)cn3)n2c1] | 3-(1-{6-acetylimidazo[1,2-a]pyridin-3-yl}-1H-pyrazol-4-yl)-N-cyclopropyl-4-methylbenzamide |
| 77 | 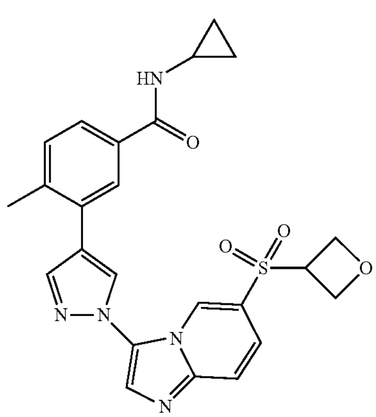 [SMILES: Cc1ccc(C(=O)NC2CC2)cc1-c1cnn(-c2cnc3ccc(S(=O)(=O)C4COC4)cn23)c1] | N-cyclopropyl-4-methyl-3-{1-[6-(oxetane-3-sulfonyl)imidazo[1,2-a]pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
| --- | --- | --- |
| 78 | 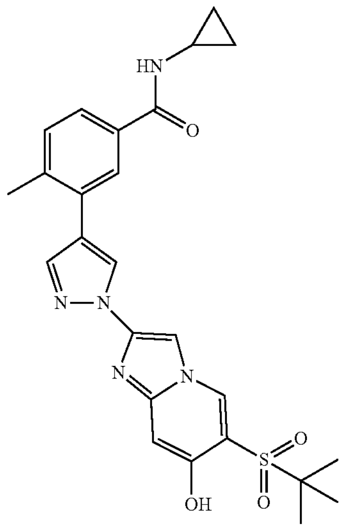 [SMILES: Cc1ccc(C(=O)NC2CC2)cc1-c1cnn(-c2cn3cc(S(=O)(=O)C(C)(C)C)c(O)cc3n2)c1] | N-cyclopropyl-3-{1-[7-hydroxy-6-(2-methylpropane-2-sulfonyl)imidazo[1,2-a]pyridin-2-yl]-1H-pyrazol-4-yl}-4-methylbenzamide |
| 79 | 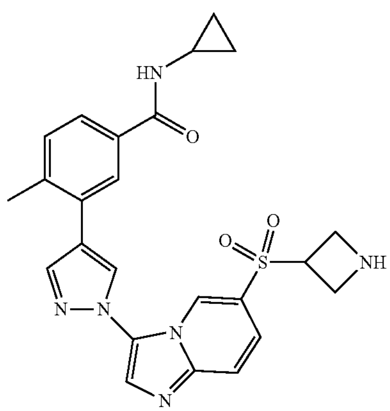 [SMILES: Cc1ccc(C(=O)NC2CC2)cc1-c1cnn(-c2cnc3ccc(S(=O)(=O)C4CNC4)cn23)c1] | 3-{1-[6-(azetidine-3-sulfonyl)imidazo[1,2-a]pyridin-3-yl]-1H-pyrazol-4-yl}-N-cyclopropyl-4-methylbenzamide |
| 80 | 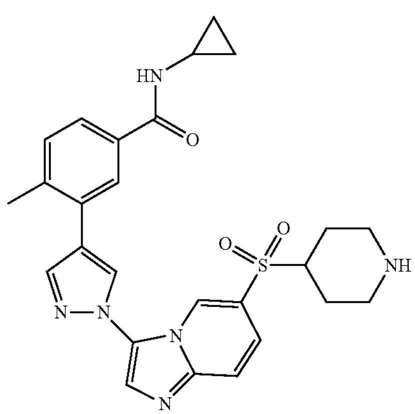 [SMILES: Cc1ccc(C(=O)NC2CC2)cc1-c1cnn(-c2cnc3ccc(S(=O)(=O)C4CCNCC4)cn23)c1] | N-cyclopropyl-4-methyl-3-{1-[6-(piperidine-4-sulfonyl)imidazo[1,2-a]pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 81-1 | 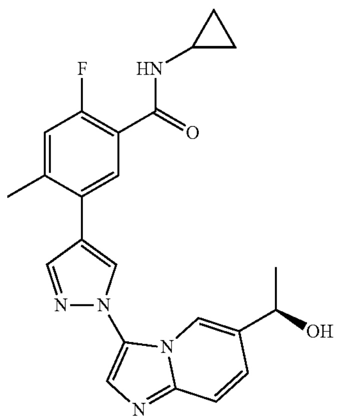 [SMILES: Cc1cc(F)c(C(=O)NC2CC2)cc1-c1cnn(-c2cnc3ccc([C@@H](C)O)cn23)c1] | N-cyclopropyl-2-fluoro-5-(1-{6-[(1R)-1-hydroxyethyl]imidazo[1,2-a]pyridin-3-yl}-1H-pyrazol-4-yl)-4-methylbenzamide |
| 81-2 | 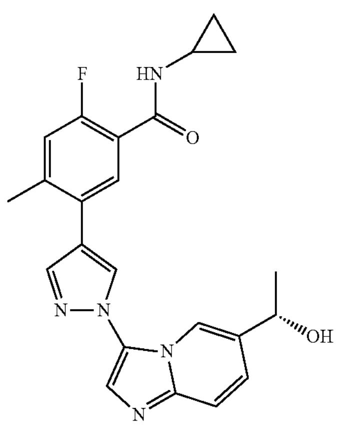 [SMILES: Cc1cc(F)c(C(=O)NC2CC2)cc1-c1cnn(-c2cnc3ccc([C@H](C)O)cn23)c1] | N-cyclopropyl-2-fluoro-5-(1-{6-[(1S)-1-hydroxyethyl]imidazo[1,2-a]pyridin-3-yl}-1H-pyrazol-4-yl)-4-methylbenzamide |
| 82-1 | 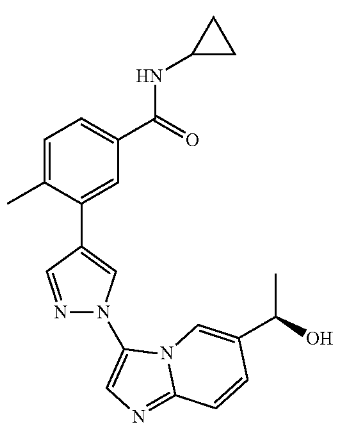 [SMILES: Cc1ccc(C(=O)NC2CC2)cc1-c1cnn(-c2cnc3ccc([C@@H](C)O)cn23)c1] | N-cyclopropyl-3-(1-{6-[(1R)-1-hydroxyethyl]imidazo[1,2-a]pyridin-3-yl}-1H-pyrazol-4-yl)-4-methylbenzamide |

TABLE 1-continued

The following are representative compounds of the invention which can be made by the general synthetic schemes, the examples, and known methods in the art.

| Example | Structure | Structure Name |
|---|---|---|
| 82-2 | 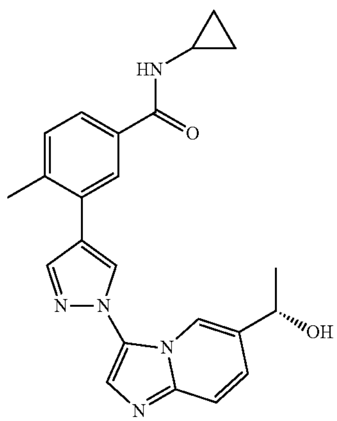 [SMILES: Cc1ccc(C(=O)NC2CC2)cc1-c1cnn(-c2cnc3ccc([C@H](C)O)cn23)c1] | N-cyclopropyl-3-(1-{6-[(1S)-1-hydroxyethyl]imidazo[1,2-a]pyridin-3-yl}-1H-pyrazol-4-yl)-4-methylbenzamide |
| 84 | 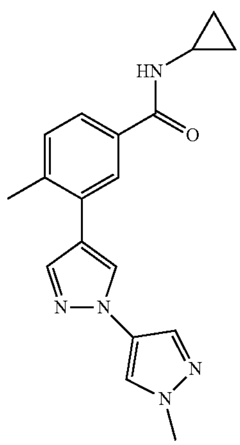 [SMILES: Cc1ccc(C(=O)NC2CC2)cc1-c1cnn(-c2cnn(C)c2)c1] | N-cyclopropyl-4-methyl-3-[1-(1-methyl-1H-pyrazol-4-yl)-1H-pyrazol-4-yl]benzamide |
| 85 | 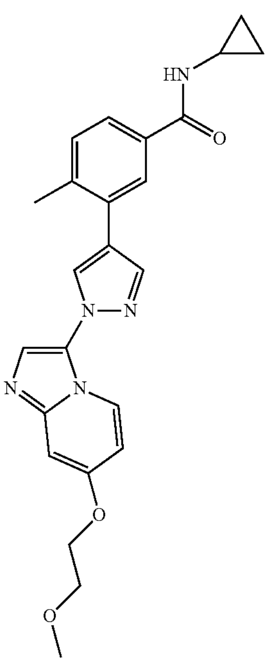 [SMILES: COCCOc1ccn2c(-n3cc(-c4cc(C(=O)NC5CC5)ccc4C)cn3)cnc2c1] | N-cyclopropyl-3-{1-[7-(2-methoxyethoxy)imidazo[1,2-a]pyridin-3-yl]-1H-pyrazol-4-yl}-4-methylbenzamide |

TABLE 1-continued

The following are representative compounds of the invention which can be made by the general synthetic schemes, the examples, and known methods in the art.

| Example | Structure | Structure Name |
|---|---|---|
| 86 | 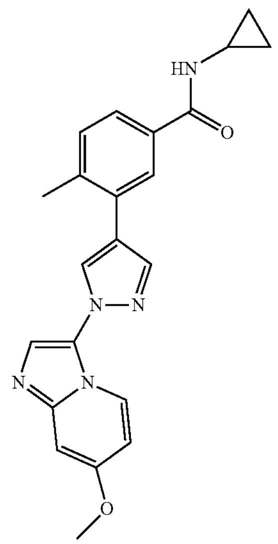 [SMILES: COc1ccn2c(-n3cc(-c4cc(C(=O)NC5CC5)ccc4C)cn3)cnc2c1] | N-cyclopropyl-3-(1-{7-methoxyimidazo[1,2-a]pyridin-3-yl}-1H-pyrazol-4-yl)-4-methylbenzamide |
| 87 | 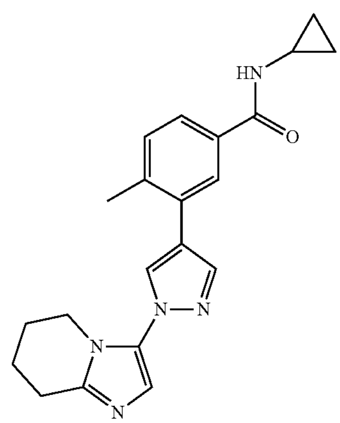 [SMILES: Cc1ccc(C(=O)NC2CC2)cc1-c1cnn(-c2cnc3n2CCCC3)c1] | N-cyclopropyl-3-(1-{5H,6H,7H,8H-imidazo[1,2-a]pyridin-3-yl}-1H-pyrazol-4-yl)-4-methylbenzamide |
| 88 | 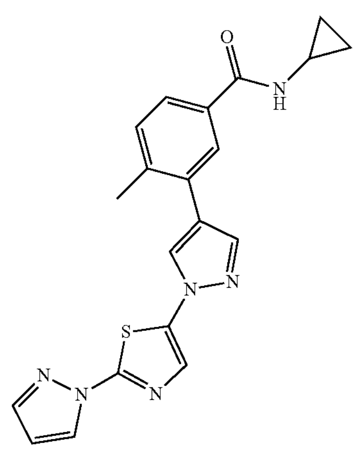 [SMILES: Cc1ccc(C(=O)NC2CC2)cc1-c1cnn(-c2cnc(-n3cccn3)s2)c1] | N-cyclopropyl-4-methyl-3-{1-[2-(1H-pyrazol-1-yl)-1,3-thiazol-5-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 89 | 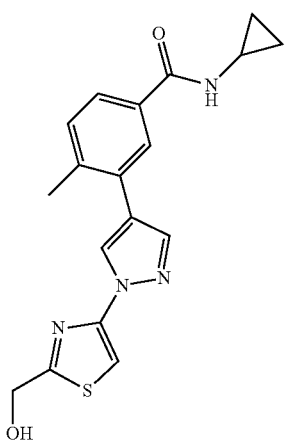 [SMILES: Cc1ccc(C(=O)NC2CC2)cc1-c1cnn(-c2csc(CO)n2)c1] | N-cyclopropyl-3-{1-[2-(hydroxymethyl)-1,3-thiazol-4-yl]-1H-pyrazol-4-yl}-4-methylbenzamide |
| 90 | 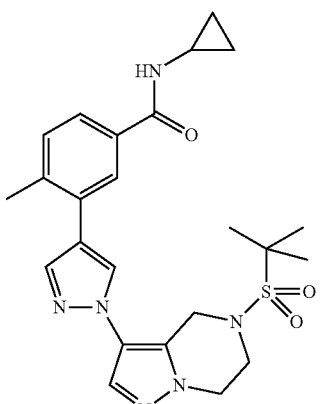 | N-cyclopropyl-4-methyl-3-{1-[5-(2-methylpropane-2-sulfonyl)-4H,5H,6H,7H-pyrazolo[1,5-a]pyrazin-3-yl]-1H-pyrazol-4-yl}benzamide |
| 91 | 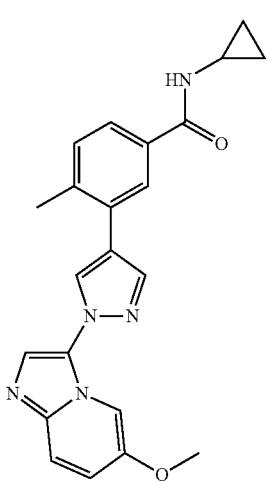 [SMILES: COc1ccc2ncc(-n3cc(-c4cc(C(=O)NC5CC5)ccc4C)cn3)n2c1] | N-cyclopropyl-3-(1-{6-methoxyimidazo[1,2-a]pyridin-3-yl}-1H-pyrazol-4-yl)-4-methylbenzamide |

TABLE 1-continued

The following are representative compounds of the invention which can be made by the general synthetic schemes, the examples, and known methods in the art.

| Example | Structure | Structure Name |
|---|---|---|
| 92 | 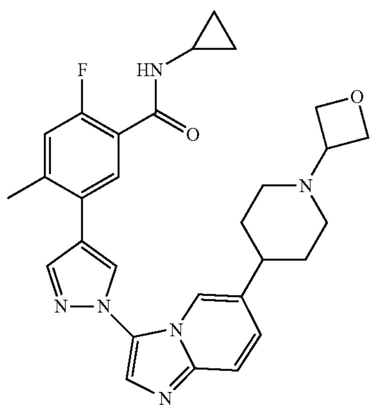 [SMILES: Cc1cc(F)c(C(=O)NC2CC2)cc1-c1cnn(-c2cnc3ccc(C4CCN(C5COC5)CC4)cn23)c1] | N-cyclopropyl-2-fluoro-4-methyl-5-(1-{6-[1-(oxetan-3-yl)piperidin-4-yl]imidazo[1,2-a]pyridin-3-yl}-1H-pyrazol-4-yl)benzamide |
| 93 | 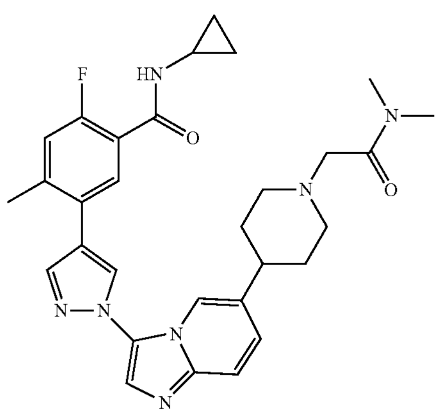 | N-cyclopropyl-5-[1-(6-{1-[(dimethylcarbamoyl)methyl]piperidin-4-yl}imidazo[1,2-a]pyridin-3-yl)-1H-pyrazol-4-yl]-2-fluoro-4-methylbenzamide |
| 94 | 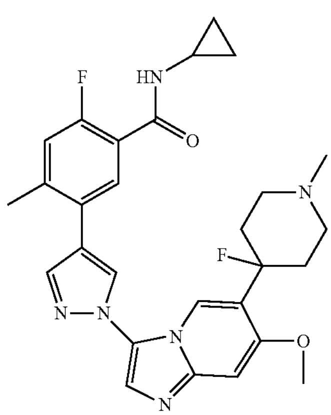 | N-cyclopropyl-2-fluoro-5-[1-(6-{4-fluoro-1-methylpiperidin-4-yl}-7-methoxyimidazo[1,2-a]pyridin-3-yl)-1H-pyrazol-4-yl]-4-methylbenzamide |

TABLE 1-continued

The following are representative compounds of the invention which can be made by the general synthetic schemes, the examples, and known methods in the art.

| Example | Structure | Structure Name |
|---|---|---|
| 95 | 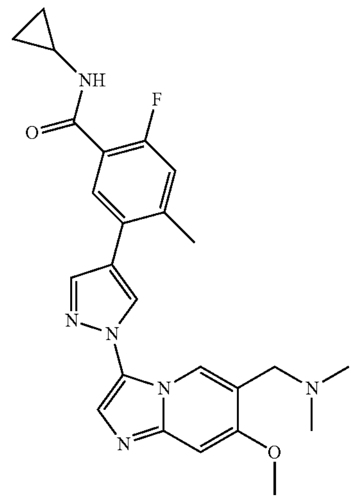 [SMILES: COc1cc2ncc(-n3cc(-c4cc(C(=O)NC5CC5)c(F)cc4C)cn3)n2cc1CN(C)C] | N-Cyclopropyl-5-[1-(6-dimethylaminomethyl-7-methoxy-imidazo[1,2-a]pyridin-3-yl)-1H-pyrazol-4-yl]-2-fluoro-4-methyl-benzamide |
| 96 | 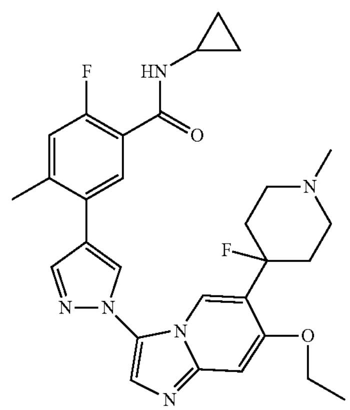 [SMILES: CCOc1cc2ncc(-n3cc(-c4cc(C(=O)NC5CC5)c(F)cc4C)cn3)n2cc1C1(F)CCN(C)CC1] | N-Cyclopropyl-5-{1-[7-ethoxy-6-(4-fluoro-1-methyl-piperidin-4-yl)-imidazo[1,2-a]pyridin-3-yl]-1H-pyrazol-4-yl}-2-fluoro-4-methyl-benzamide |
| 97 | 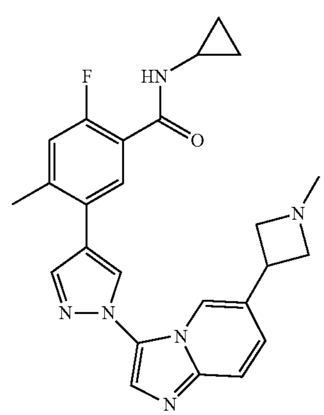 | N-Cyclopropyl-2-fluoro-4-methyl-5-{1-[6-(1-methyl-azetidin-3-yl)-imidazo[1,2-a]pyridin-3-yl]-1H-pyrazol-4-yl}-benzamide |

TABLE 1-continued

The following are representative compounds of the invention which can be made by the general synthetic schemes, the examples, and known methods in the art.

| Example | Structure | Structure Name |
|---|---|---|
| 98 | 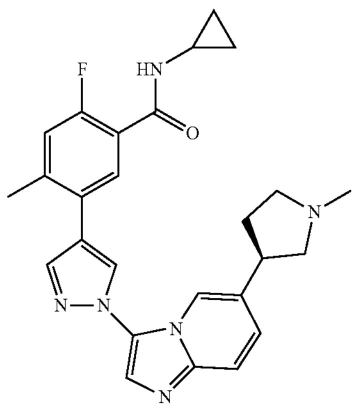 | N-Cyclopropyl-2-fluoro-4-methyl-5-{1-[6-((R)-1-methyl-pyrrolidin-3-yl)-imidazo[1,2-a]pyridin-3-yl]-1H-pyrazol-4-yl}-benzamide |
| 99 | 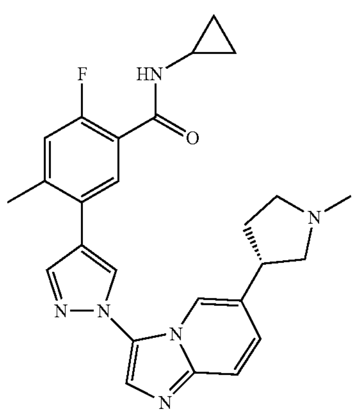 | N-Cyclopropyl-2-fluoro-4-methyl-5-{1-[6-((S)-1-methyl-pyrrolidin-3-yl)-imidazo[1,2-a]pyridin-3-yl]-1H-pyrazol-4-yl}-benzamide |
| 100 | 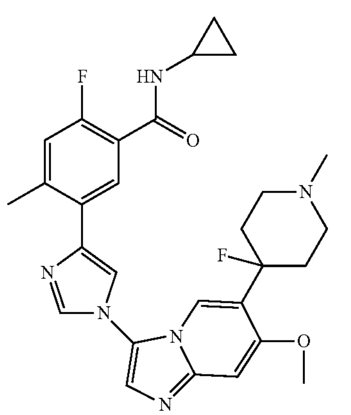 | N-Cyclopropyl-2-fluoro-5-{1-[6-(4-fluoro-1-methyl-piperidin-4-yl)-7-methoxy-imidazo[1,2-a]pyridin-3-yl]-1H-imidazol-4-yl}-4-methyl-benzamide |

TABLE 1-continued

The following are representative compounds of the invention which can be made by the general synthetic schemes, the examples, and known methods in the art.

| Example | Structure | Structure Name |
|---|---|---|
| 101 | | N-Cyclopropyl-5-{1-[6-(1-ethyl-4-fluoro-piperidin-4-yl)-7-methoxy-imidazo[1,2-a]pyridin-3-yl]-1H-pyrazol-4-yl}-2-fluoro-4-methyl-benzamide | or the pharmaceutically acceptable salts thereof.

In one embodiment, the invention relates to any of the compounds depicted in Table 1 above and the pharmaceutically acceptable salts thereof.

For all compounds disclosed hereinabove in this application, in the event the nomenclature is in conflict with the structure, it shall be understood that the compound is defined by the structure. For compounds with stereogenic centers, the structures show the absolute stereochemistry.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

It shall be understood that if N is not substituted then it is NH. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ carbocycle" or "$C_{3-10}$ cycloalkyl" refers to a nonaromatic 3 to 10-membered (but preferably, 3 to 6-membered) monocyclic carbocyclic/cycloalkyl radical or a nonaromatic 6 to 10-membered fused bicyclic, bridged bicyclic, or spirocyclic carbocyclic radical. The $C_{3-10}$ carbocycle/cycloalkyl ring may be either saturated or partially unsaturated, and the carbocycle/cycloalkyl ring may be attached by any atom of the cycle which results in the creation of a stable structure. Non-limiting examples of 3 to 10-membered monocyclic carbocycles/cycloalkyl rings include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic/cycloalkyl radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo [2.2.2]heptanyl, bicyclo

[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "aryl" refers to aromatic hydrocarbon rings containing from six to ten carbon ring atoms. The term aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl, benzothiazolyl, dihydroindolyl, azaindolyl, benzothiazolyl, benzpyrrolyl, benzpyrazolyl, pyridopyrazolyl, dihydrobenzofuranyl, benzothienyl, benzodioxanyl, dihydrobenzo[1,4]dioxanyl and benzo[1,3]dioxolyl.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, aryl, cycloalkyl/carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$-$C_4$ alkyl$)_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

SYNTHETIC EXAMPLES

List of Abbreviations

| | |
|---|---|
| Ac | acetyl |
| ACN | acetonitrile |
| aq. | aquatic, aqueous |
| Boc | tert-butyloxycarbonyl |
| Boc$_2$O | di-tert-butyl dicarbonate |
| Bu | butyl |
| dba | Dibenzylideneacetone |
| Davephos | 2-dimethylamino-2'-dicyclohexylaminophosphinobiphenyl |
| DBA | dibenzylideneacetone |
| DCM | dichloromethane |
| DIPEA | N,N-diisopropylethylamine |
| DMAP | 4-N,N-dimethylaminopyridine |
| DMA | N,N-dimethylacetamide |
| DME | 1,2-dimethoxyethane |
| DMF | N,N-dimethylformamide |
| DMSO | dimethylsulphoxide |
| dppf | 1.1'-bis(diphenylphosphino)ferrocene |
| EDC | 1-(3-dimethylaminopropyl)-3-ethylcarbodiimide hydrochloride |
| equiv. | equivalent(s) |
| ESI | electron spray ionization |

| | |
|---|---|
| Et | ethyl |
| Et₂O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| hept | heptane |
| HOBt | 1-hydroxybenzotriazole |
| HPLC | high performance liquid chromatography |
| conc. | concentrated |
| LiHMDS | lithium bis(trimethylsilyl)amide |
| mCPBA | 3-chloroperoxbenzoic acid |
| Me | methyl |
| MeOH | methanol |
| min | minutes |
| MS | mass spectrometry |
| MTBE | methyl tertiary butyl ether |
| NBS | N-bromo-succinimide |
| NIS | N-iodo-succinimide |
| NMP | N-methylpyrrolidone |
| Rt | retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tertiary-butyl |
| TEA | triethylamine |
| temp. | temperature |
| tert | tertiary |
| TFA | trifluoroacetic acid |
| THF | tetrahydrofuran |
| TLC | thin layer chromatography |
| TsOH | p-toluenesulphonic acid |

General Synthetic Methods and Synthesis of Intermediates

The compounds of the invention may be prepared by the methods and examples presented below and methods known to those of ordinary skill in the art. In each of the examples below, the groups $R^1$ to $R^7$ are as defined above for general formula I unless noted. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or Preparatory HPLC.

Intermediates

Synthesis of 5-tert-butylsulfanyl-pyridin-2-ylamine (I-1)

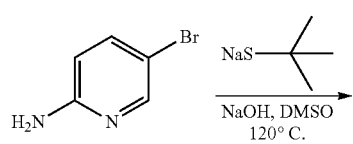

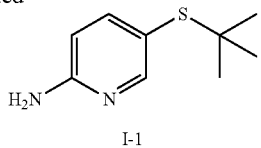

To a mixture of 5-bromo-pyridin-2-ylamine (300 mg, 1.73 mmol) in DMSO (3 mL) are added sodium 2-methyl-2-propanethiolate (388 mg, 3.47 mmol) and NaOH (35 mg, 0.87 mmol). The mixture is degassed with Ar for 20 min. To the reaction mixture are added L-proline (100 mg, 0.870 mmol) and CuI (330 mg, 1.73 mmol) and the reaction is heated to 120° C. for 12 h in a sealed tube. The reaction is then cooled to room temperature, poured into ice water, and extracted with EtOAc (2×). The solvent is removed under reduced pressure to provide 200 mg of crude 5-tert-butylsulfanyl-pyridin-2-ylamine (I-1) that was used without further purification.

Synthesis of 5-tert-butylsulfanyl-pyrazolo[1,5-a]pyridine (I-2)

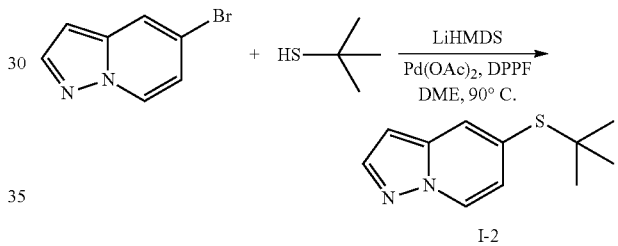

To a stirred solution of 5-bromo-pyrazolo[1,5-a]pyridine (2.0 g, 10.1 mmol) in DME (30 mL), at 0° C., is added lithium bis(trimethylsilyl)amide as a 1M solution in THF (24 mL, 25 mmol)). In another flask, palladium(II) acetate (227 mg, 1.01 mmol) and dppf (2.0 g, 3.6 mmol) are combined in DME (30 mL) and stirred at room temperature for 10 min. The two solutions are then combined at room temperature, and treated with 2-methyl-2-propanethiol (2.0 g, 22 mmol). The reaction is heated to 90° C. and stirred for 2 h. The reaction is then cooled to room temperature, diluted with water, and extracted with EtOAc (2×). The organic layer is washed with brine, dried over Na₂SO₄, and concentrated under reduced pressure. The residue is purified by flash silica gel column chromatography to provide 1 g of 5-tert-butylsulfanyl-pyrazolo[1,5-a]pyridine (I-2).

Synthesis of 6-(oxetan-3-ylsulfanyl)-imidazo[1,2-a]pyridine (I-3)

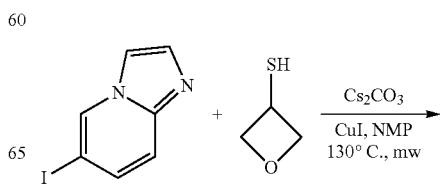

-continued

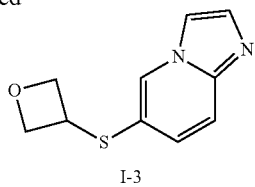

I-3

A mixture of 6-iodo-imidazo[1,2-a]pyridine (800 mg, 3.30 mmol), copper iodide (62 mg, 0.33 mmol), cesium carbonate (2.1 g, 6.6 mmol), NMP (8 mL), and oxetane-3-thiol (325 mg, 3.6 mmol) is flushed with $N_2$ and sealed in a microwave reaction tube. The mixture is heated at 130° C. for 30 min in a microwave reactor. The reaction is cooled to room temperature, filtered through celite, and rinsed with EtOAc. The filtrate is diluted with water, and extracted with EtOAc (3×). The combined organic layers are washed with brine, dried over $Na_2SO_4$, filtered, and concentrated under reduced pressure. The resulting residue is purified by flash silica gel column chromatography to provide 283 mg of 6-(oxetan-3-ylsulfanyl)-imidazo[1,2-a]pyridine (I-3).

The following intermediate is synthesized in a similar fashion as described above using commercially available starting materials:
3-(Imidazo[1,2-a]pyridin-6-ylsulfanyl)-azetidine-1-carboxylic acid tert-butyl (I-4)

Synthesis of 2-cyclopropyl-1-methyl-1H-imidazole (I-5)

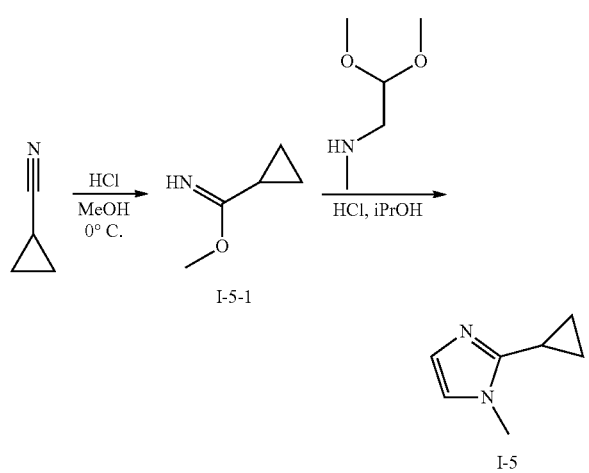

To 4N HCl in dioxane (7.3 mL, 29 mmol) at 0° C. is slowly added cylopropane carbonitrile (1 mL, 13.5 mmol) as a solution in anhydrous methanol (1.2 mL). The mixture is stirred between 0-5° C. for 3 h during which time a precipitate forms. The mixture is warmed to room temperature and the solution is concentrated under reduced pressure. MTBE (10 mL) is added, and the mixture is stirred for several minutes, then filtered to provide 783 mg of cyclopropanecarboximidic acid methyl ester HCl (I-5-1).

To a stirred suspension of I-5-1 (0.50 g, 3.9 mmol) in isopropanol (2.0 mL) is added (2,2-dimethoxy-ethyl)-methyl-amine (0.50 mL, 4.0 mmol). The mixture becomes nearly homogeneous; then a gelatinous precipitate forms. The mixture is warmed to 80° C. for 4 h then is allowed to cool to room temperature and stirred for an additional 12 h.

Concentrated HCl (1.1 mL, 13 mmol) is then added and the mixture is heated to 80° C. for 45 min. The mixture is cooled to room temperature, and poured into a saturated aqueous solution of $NaHCO_3$ (20 mL). The mixture is extracted with EtOAc (3×) and the organic layer is washed with brine, dried over $Na_2SO_4$, filtered, and concentrated to provide 212 mg of 2-cyclopropyl-1-methyl-1H-imidazole (I-5).

Synthesis of 3-bromo-6-(oxetan-3-ylsulfanyl)-imidazo[1,2-a]pyridine (I-6)

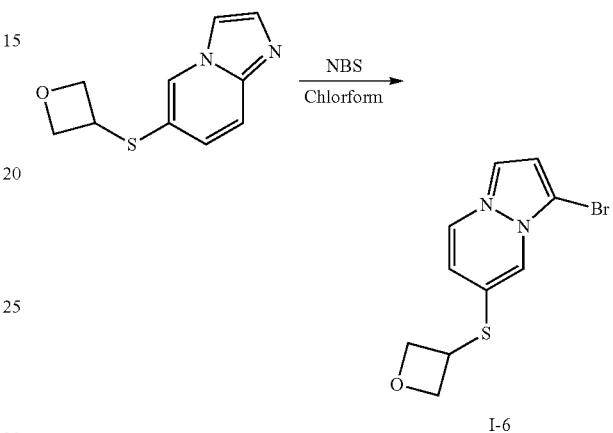

To a stirred solution of I-3 (242 mg, 1.20 mmol) in chloroform (4.2 mL) is added NBS (208 mg, 1.20 mmol). The reaction is stirred at room temperature for 30 min and then concentrated under reduced pressure. The resulting residue is purified by flash silica gel column chromatography to provide 294 mg of 3-bromo-6-(oxetan-3-ylsulfanyl)-imidazo[1,2-a]pyridine (I-6).

The following intermediate is synthesized in a similar fashion as described above using I-4:3-(3-Bromo-imidazo[1,2-a]pyridine-6-sulfonyl)-azetidine-1-carboxylic acid tert-butyl ester (I-7)

The following intermediate is synthesized in a similar fashion as described above using I-17:
3-Bromo-6-(morpholine-4-sulfonyl)-imidazo[1,2-a]pyridine (I-8)

The following intermediate is synthesized in a similar fashion as described above using I-18
3-Bromo-6-methanesulfonyl-imidazo[1,2-a]pyridine (I-9)

The following intermediate is synthesized in a similar fashion as described above using I-20
3-Bromo-6-tert-butylsulfanyl-imidazo[1,2-a]pyridine (I-10)

The following intermediate is synthesized in a similar fashion as described above using I-23
3-Bromo-5-(2-methyl-propane-2-sulfonyl)-pyrazolo[1,5-a]pyridine (I-11)

The following intermediate is synthesized in a similar fashion as described above using I-16
3-Bromo-5-ethanesulfonyl-pyrazolo[1,5-a]pyridine (I-12)

The following intermediate is synthesized in a similar fashion as described above using I-19
3-Bromo-6-(4-methyl-piperazine-1-sulfonyl)-imidazo[1,2-a]pyridine (I-13)

The following intermediate is synthesized in a similar fashion as described above using I-5
5-Bromo-2-cyclopropyl-1-methyl-1H-imidazole (I-14)

The following intermediate is synthesized in a similar fashion as described above using I-32
3-Bromo-6-[1-(tert-butyl-dimethyl-silanyloxy)-1-methyl-ethyl]-imidazo[1,2-a]pyridine (I-15)

Synthesis of 5-ethanesulfonyl-pyrazolo[1,5-a]pyridine (I-16)

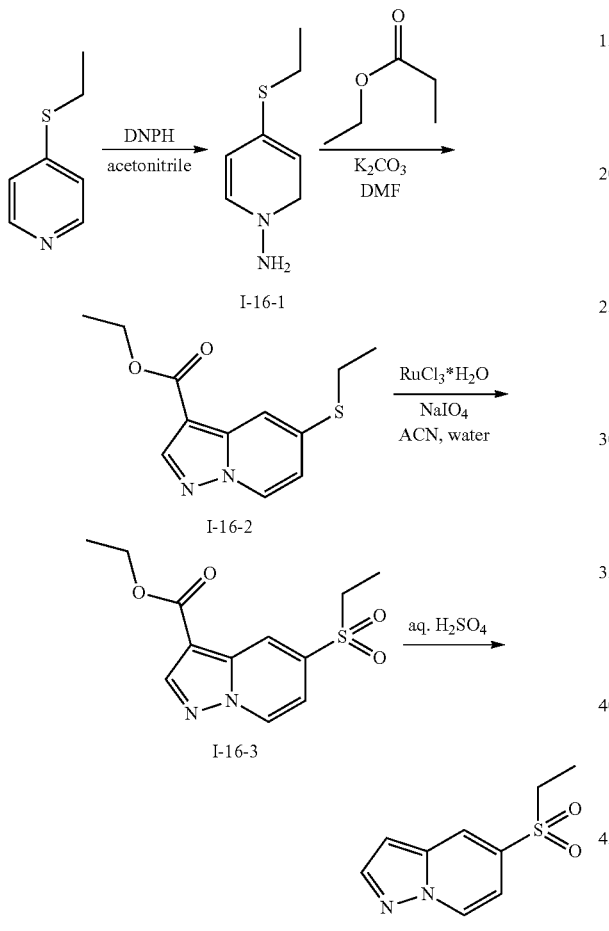

To a stirred solution of ethylsulfanyl-pyridine (5.0 g, 36 mmol) in acetonitrile (50 mL), at 0° C., is added 2,4-dinitrophenyl hydroxyl amine (DNPH) (7.0 g, 35 mmol) in several portions. The reaction is slowly warmed to room temperature and then heated to 40° C. for 15 h. The reaction is concentrated under reduced pressure to provide 5.0 g of 4-ethylsulfanyl-2H-pyridin-1-ylamine (I-16-1).

To a stirred solution of crude I-16-1 (5.0 g, 32 mmol) in DMF (50 mL), cooled to 0° C., is added $K_2CO_3$ (4.0 g, 29 mmol). To the reaction mixture is added, dropwise, ethyl propionate (3.0 g, 29 mmol) and the reaction is slowly warmed to rt. After 2 h, the reaction is diluted with water and extracted with EtOAc (3×). The combined organic layer is concentrated under reduced pressure to yield 2.0 g of crude 5-ethylsulfanyl-pyrazolo[1,5-a]pyridine-3-carboxylic acid ethyl ester (I-16-2).

To a stirred solution of I-16-2 (1.0 g, 4.0 mmol) in a mixture of acetonitrile (5.0 mL) and water (10.0 mL), cooled to 0 C, is added ruthenium(III)chloride hydrate (826 mg, 4.0 mmol) and sodium metaperiodate (2.0 mg, 9.0 mmol). After 30 minutes, the reaction is diluted with water and extracted with EtOAc The organic layer is concentrated under reduced pressure to provide 500 mg of the crude 5-Ethanesulfonyl-pyrazolo[1,5-a]pyridine-3-carboxylic acid ethyl ester (I-16-3).

To a stirred solution of sulfuric acid (2.0 g) in water (4.0 mL), at 0° C., is slowly added I-16-3 (1.0 g, 3.6 mmol). The reaction is stirred at 90° C. for 2 h then cooled to room temperature. The pH of the mixture is adjusted to neutral by addition of a 2N NaOH solution and then extracted with DCM (2×). The combined organic layers are washed with brine, dried over $Na_2SO_4$, and concentrated under reduced pressure. The residue is purified by flash silica gel column chromatography to provide 298 mg of 5-ethanesulfonyl-pyrazolo[1,5-a]pyridine (I-16).

Synthesis of 6-(morpholine-4-sulfonyl)-imidazo[1,2-a]pyridine (I-17)

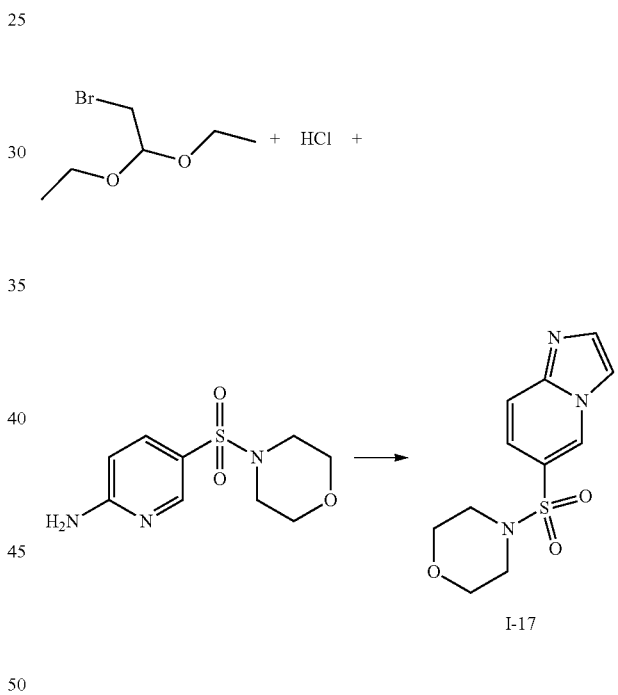

A mixture of bromoacetaldehyde diethyl acetal (383 μL, 2.50 mmol) and aq. 2M HCl solution (1.4 mL, 2.7 mmol) is stirred at room temperature for 2 h. The reaction is then heated to 80° C. for 1 h. The reaction is cooled to 5° C. and the pH of the mixture adjusted to pH 8 by the addition of solid sodium bicarbonate. To the reaction mixture is added 5-(morpholine-4-sulfonyl)-pyridin-2-ylamine (300 mg, 1.2 mmol) and the resulting solution is warmed to room temperature and stirred overnight. The mixture is concentrated under reduced pressure and diluted with EtOAc (10 mL). The mixture is sonicated and filtered. The filtrate is concentrated under reduced pressure and the resulting residue is purified by flash silica gel column chromatography to provide 165 mg of 6-(morpholine-4-sulfonyl)-imidazo[1,2-a]pyridine (I-17).

The following intermediates are synthesized in a similar fashion as described above using commercially available material:
6-Methanesulfonyl-imidazo[1,2-a]pyridine (I-18)
6-(4-Methyl-piperazine-1-sulfonyl)-imidazo[1,2-a]pyridine (I-19)
The following intermediate is synthesized in a similar fashion as described above using I-1
6-tert-Butylsulfanyl-imidazo[1,2-a]pyridine (I-20)

Synthesis of 3-(imidazo[1,2-a]pyridine-6-sulfonyl)-azetidine-1-carboxylic acid tert-butyl Ester (I-21)

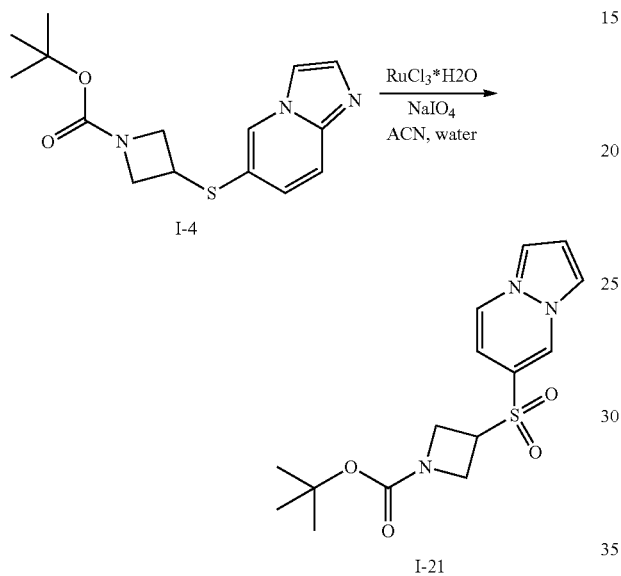

To a stirred solution of I-4 (480 mg, 1.6 mmol) in a mixture of acetonitrile (20 mL) and water (10 mL), at room temperature, is added ruthenium(III) chloride hydrate (19 mg; 0.1 mmol) and sodium metaperiodate (2.0 g, 9.4 mmol). After 1 h, the reaction is extracted with EtOAc (3×), washed with brine, dried over Ns₂SO₄, and concentrated under reduced pressure. The residue is purified by flash silica gel column chromatography to afford 100 mg of 3-(imidazo[1,2-a]pyridine-6-sulfonyl)-azetidine-1-carboxylic acid tert-butyl ester (I-21).

The following intermediate is synthesized according to the intermediate described above using I-10:
3-Bromo-6-(2-methyl-propane-2-sulfonyl)-imidazo[1,2-a]pyridine (I-22)
The following intermediate is synthesized according to the intermediate described above using I-2
5-(2-Methyl-propane-2-sulfonyl)-pyrazolo[1,5-a]pyridine (I-23)

Synthesis of 3-bromo-7-methoxy-6-(2-methyl-propane-2-sulfonyl)-imidazo[1,2-a]-pyridine (I-24)

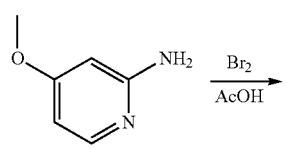

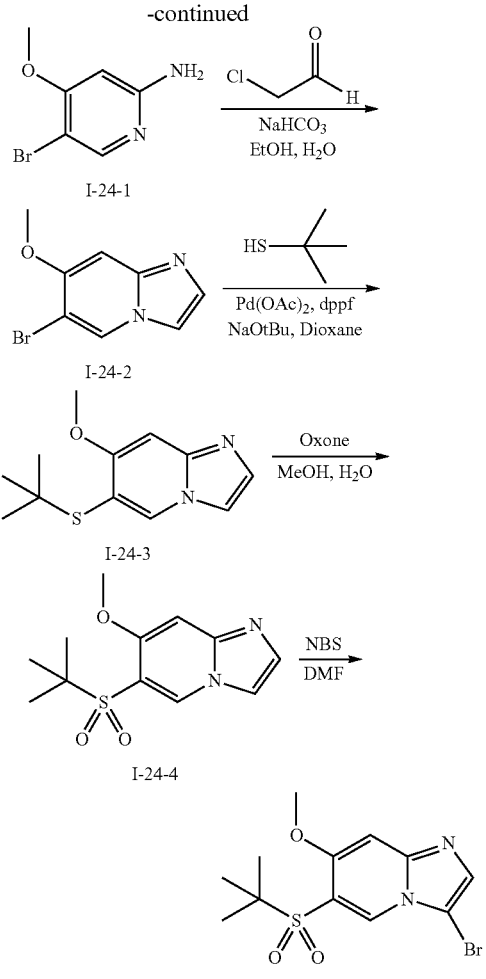

To a stirred solution of 4-methoxypyridin-2-ylamine (15 g, 121 mmol) in acetic acid (490 mL), at room temperature, is slowly added bromine as a 1M solution in acetic acid (120 mL, 120 mmol). After 1.5 h, the reaction mixture is filtered and the collected solid is dissolved in EtOAc. The mixture is washed with saturated NaHCO₃ followed by water and then brine. The organic layer is dried over anhydrous Na₂SO₄, filtered, and the filtrate is concentrated under reduced pressure to provide 15.1 g of 5-bromo-4-methoxy-pyridin-2-ylamine (I-24-1).

To a stirred solution of I-24-1 (15 g, 74 mmol) in a 4:1 mixture of ethanol-water (150 mL) is added an aqueous solution of chloroacetaldehyde (55% aqueous solution, 15 mL, 88.7 mmol) followed by addition of solid NaHCO₃ (7.4 g, 89 mmol). The resulting solution is refluxed for 4 h, then cooled to room temperature, diluted with water, and extracted with EtOAc (2×). The combined organic layer is dried over anhydrous Na₂SO₄, filtered, and concentrated under reduced pressure. The residue is purified by flash silica gel column chromatography to provide 10.6 g of 6-bromo-7-methoxy-imidazo [1,2-a]pyridine (I-24-2).

To a stirred suspension of I-24-2 (13 g, 56 mmol) in 1,4-dioxane (360 mL) is added NaOtBu (6.6 g, 69 mmol) and 2-methyl-2-propanethiol (7.74 g, 85.9 mmol). The resulting mixture is degassed with Ar for 5 min, then treated with Pd(OAc)₂ (250 mg, 1.14 mmol) and dppf (760 mg, 1.37 mmol). The reaction is heated at 90° C. for 12 h then cooled to room temperature and filtered.

The filtrate is diluted with water and extracted with EtOAc (3×). The combined organic layer is washed with water followed by brine, then dried over anhydrous Na$_2$SO$_4$, filtered, and concentrated under reduced pressure. The residue is purified by flash column chromatography to provided 10.4 g of 6-tert-butylsulfanyl-7-methoxy-imidazo [1,2-a] pyridine (I-24-3).

To a stirred solution of I-24-3 (6.0 g, 25 mmol) in a 1:1 mixture of MeOH:water (60 mL), at 0° C., is added Oxone® (47 g, 76 mmol). The resulting mixture is allowed to stir with warming to room temperature over 1 h. The mixture is filtered and the filter pad is washed with EtOAc. The pH of the combined filtrate is adjusted to neutral by addition of a saturated solution of NaHCO$_3$ then extracted with EtOAc. The combined organic layer is washed with water, dried over anhydrous Na$_2$SO$_4$, filtered, and concentrated under reduced pressure. The residue is purified by flash silica gel column chromatography to provide 6.0 g of 7-methoxy-6-(2-methyl-propane-2 sulfonyl) imidazole [1,2-a] pyridine (I-24-4).

To a stirred solution of I-24-4 (6.0 g, 18.6 mmol) in DMF (30 mL) is added NBS (3.3 g, 18.6 mmol). The resulting mixture is stirred at room temperature for 30 min, then diluted with water and extracted with EtOAc. The organic layer is washed with water (4×) followed by brine then dried over anhydrous Na$_2$SO$_4$, filtered, and concentrated under reduced pressure. The residue is purified by flash silica gel column chromatography to provide 5.5 g of 3-bromo-7-methoxy-6-(2-methyl-propane-2-sulfonyl)-imidazo[1,2-a] pyridine (I-24).

Synthesis of 3-bromo-imidazo[1,2-a]pyridine-6-carboxylic Acid Methylamide (I-25)

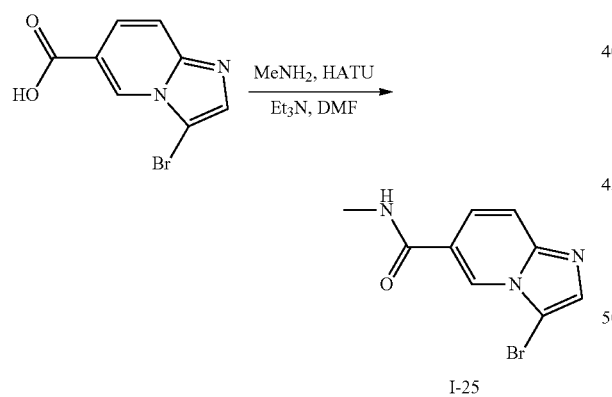

I-25

To a stirred solution of 3-bromo-imidazo[1,2-a]pyridine-6-carboxylic acid (130 mg, 0.540 mmol) in DMF (2.1 mL), at room temperature, is added Et$_3$N (376 μL, 2.7 mmol) followed by a solution of methylamine in EtOH (33 wt %, 101 mg, 1.1 mmol), and HATU (308 mg, 0.81 mmol). The reaction is stirred at room temperature for 18 h then diluted with water and extracted with EtOAc (3×). The organic layer is washed with water followed by brine then dried over Na$_2$SO$_4$, filtered, and concentrated under reduced pressure. The resulting residue is purified by flash silica gel chromatography to provide 83 mg of 3-bromo-imidazo[1,2-a]pyridine-6-carboxylic acid methylamide.

The following intermediate is synthesized in a similar fashion as described above using a commercially available amine:
3-Bromo-imidazo[1,2-a]pyridine-6-carboxylic acid dimethylamide (I-26)

Synthesis of 5-bromo-thiazole-2-carboxylic Acid Amide (I-27)

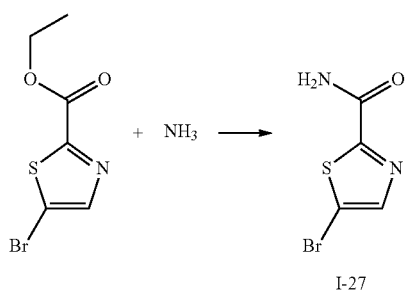

I-27

To a stirred solution of 5-bromo-thiazole-2-carboxylic acid ethyl ester (100 mg, 0.42 mmol) is added to a 7M solution of ammonia in MeOH (3.0 ml, 21 mmol). The reaction is stirred at 80° C. for 12 h in a sealed tube then cooled to room temperature and concentrated under reduced pressure to provide 88 mg of 5-bromo-thiazole-2-carboxylic acid amide (I-28).

The following intermediate is synthesized in a similar fashion as described above using a commercially available amine:
5-Bromo-thiazole-2-carboxylic acid methylamide (I-29)

Synthesis of 3-bromo-6-[1-(tert-butyl-dimethyl-silanyloxy)-ethyl]-imidazo[1,2-a]pyridine (I-30)

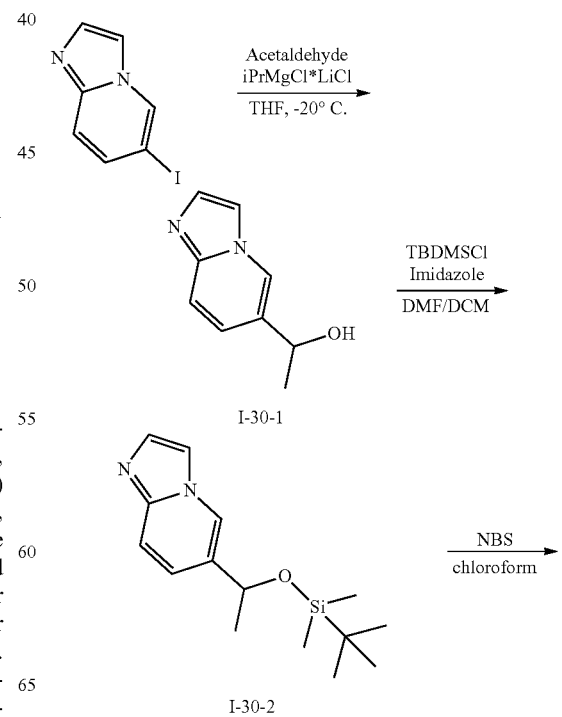

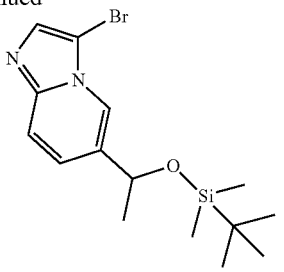

I-30

To a stirred solution of 6-iodo-imidazo[1,2-a]pyridine (3.8 g, 16 mmol) in THF (204 mL) at −20° C. is added iPrMgCl*LiCl as a 1.3 M solution in THF (14.5 mL, 18.8 mmol). After stirring for 20 min, a solution of 5M acetaldehyde in THF (4.1 mL, 20 mmol) is added. The reaction is stirred for 5 min at −20° C. and then the cold bath is removed and the mixture is allowed to warm to room temperature. After 1.5 h, the reaction is diluted with saturated aqueous sodium bicarbonate solution (2 mL) then concentrated under reduced pressure. The resulting residue is purified by flash silica gel column chromatography to provide 2.1 g of 1-imidazo[1,2-a]pyridin-6-yl-ethanol (I-30-1).

A mixture of I-30-1 (3.0 g, 18.5 mmol), TBDMSCl (4.0 g; 27 mmol), and imidazole (2.0 g, 30 mmol) are dissolved in a 9:1 mixture of DMF:DCM (60 mL). The reaction is stirred at room temperature for 3 h then concentrated under reduced pressure. The resulting residue is purified by flash silica gel column chromatography to provide 4.26 g of 6-[1-(tert-butyl-dimethyl-silanyloxy)-ethyl]-imidazo[1,2-a]pyridine (I-30-2).

To a stirred solution of I-30-2 (4.3 g, 15 mmol) in chloroform (55 mL), at room temperature, is added NBS (2.7 g, 15 mmol). After 25 min, the reaction is diluted with saturated NaHCO₃ solution and extracted with EtOAc (3×). The combined organic layers are washed with brine, dried over anhydrous Na₂SO₄, and concentrated under reduced pressure. The residue is purified by flash silica gel chromatography to provide 5.3 g of 3-bromo-6-[1-(tert-butyl-dimethyl-silanyloxy)-ethyl]-imidazo[1,2-a]pyridine (I-30).

The following intermediate is synthesized in a similar fashion as described above using a commercially available aldehyde:
3-Bromo-6-[(tert-butyl-dimethyl-silanyloxy)-(tetrahydropyran-4-yl)-methyl]-imidazo[1,2-a]pyridine (I-31)

Synthesis of 2-Imidazo[1,2-a]pyridin-6-yl-propan-2-ol (I-31)

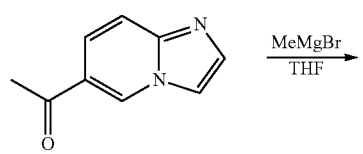

I-31

To a stirred solution of 1-imidazo[1,2-a]pyridin-6-yl-ethanone (710 mg, 4.4 mmol) in THF (35 mL), at −78° C., is added MeMgBr as a solution in THF (3M, 1.6 mL, 4.8 mmol). The mixture is allowed to warm to room temperature overnight. The mixture is then quenched with saturated NH₄Cl solution, extracted with EtOAc (3×), and concentrated under reduced pressure. The residue is purified by flash silica gel column chromatography to provide 576 mg of 2-imidazo[1,2-a]pyridin-6-yl-propan-2-ol (I-31).

Synthesis of 6-[1-(tert-butyl-dimethyl-silanyloxy)-1-methyl-ethyl]-imidazo[1,2-a]pyridine (I-32)

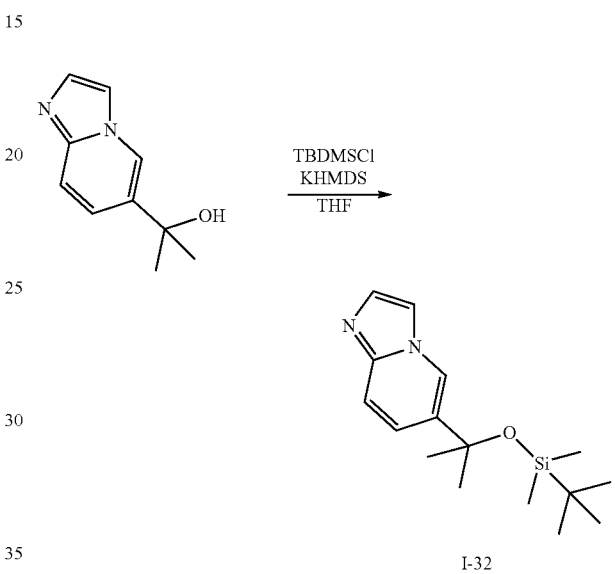

I-32

To a stirred solution of I-31 (467 mg, 2.70 mmol) in THF (6.0 mL), at room temperature, is added, dropwise, KHMDS as a solution in toluene (0.5 M, 5.3 mL, 2.6 mmol). To this mixture is added a solution of TBDMSCl (400 mg, 2.65 mmol) in THF (4 mL). After 1.5 h, the reaction is diluted with water and extracted with EtOAc (3×). The organic layer is washed with brine, dried over Na₂SO₄, filtered, and concentrated. The residue is purified by flash silica gel column chromatography to yield 400 mg of 6-[1-(tert-butyl-dimethyl-silanyloxy)-1-methyl-ethyl]-imidazo[1,2-a]pyridine (I-32).

Synthesis of 3-bromo-5-(2-methyl-propane-2-sulfinyl)-4,5,6,7-tetrahydro-pyrazolo[1,5-a]pyrazine(I-33)

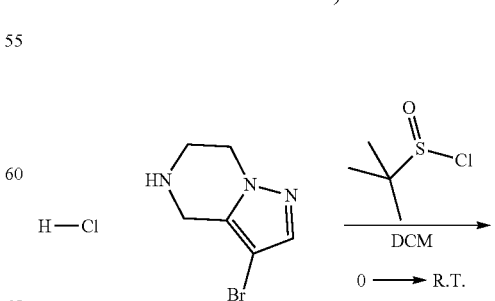

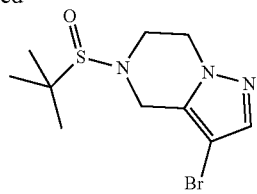

I-33

To a mixture of 3-bromo-4,5,6,7-tetrahydro-pyrazolo[1,5-a]pyrazine hydrochloride (0.90 g, 3.8 mmol) and triethylamine (2.3 g, 22.6 mmol) in anhydrous dichloromethane (20 mL), at 0° C., is added 2-methyl-propane-2-sulfinyl chloride (1.3 g, 9.4 mmol). After stirring for 16 hours, the reaction is diluted with water (5 mL) and extracted with DCM (3×). The combined organic extracts are dried (Na$_2$SO$_4$), filtered and concentrated under reduced pressure. The residue is purified by flash silica gel chromatography to afford 0.9 g of 3-bromo-5-(2-methyl-propane-2-sulfinyl)-4,5,6,7-tetrahydro-pyrazolo[1,5-a]pyrazine (I-33).

Synthesis of 3-bromo-5-(2-methyl-propane-2-sulfonyl)-4,5,6,7-tetrahydro-pyrazolo[1,5-a]pyrazine(I-34)

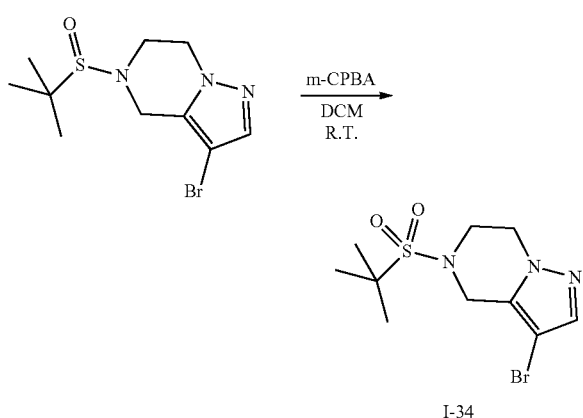

I-34

To a solution of I-33 (0.9 g, 2.9 mmol) in anhydrous DCM (20 mL) is added mCPBA (0.76 g, 4.4 mmol). After stirring for 16 h, saturated aqueous sodium sulfite (2 mL) is added and the reaction is stirred for 30 minutes. The reaction is then extracted with DCM (3×20 mL) and the combined organic extracts are dried (Na$_2$SO$_4$), filtered, and concentrated under reduced pressure. The residue is purified by flash silica gel chromatography to afford 0.7 g of 3-bromo-5-(2-methyl-propane-2-sulfonyl)-4,5,6,7-tetrahydro-pyrazolo[1,5-a]pyrazine (I-34).

Synthesis of 3-bromo-7-(2-methoxyethoxy)imidazo[1,2-a]pyridine (I-35)

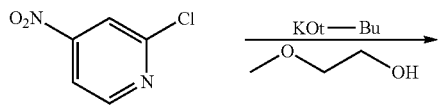

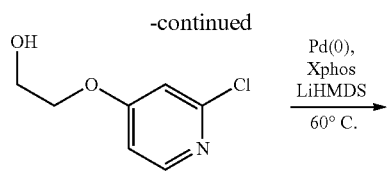

I-35-1

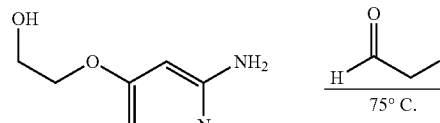

I-35-2

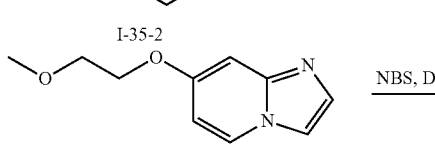

I-35-3

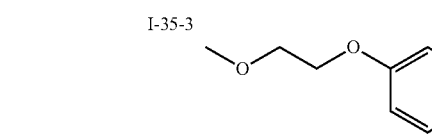

I-35

To a stirred solution of 2-chloro-4-nitro-pyridine (8.0 g, 50 mmol) in 2-methoxyethanol (9.9 mL, 130 mmol), at 0° C., is added KOt-Bu (6.2 g, 55 mmol) in several portions. After addition, the reaction mixture is stirred at ambient temperature for 3 h. The reaction mixture is partitioned between DCM and water, and then the layers are separated. The aqueous layer is extracted with EtOAc (2×) and the combined organic layer is washed with brine, dried over anhydrous MgSO$_4$, and concentrated under reduced pressure to afford 5.2 g of 2-[(2-chloro-4-pyridyl)oxy]ethanol (I-35-1) which is used in subsequent steps without further purification.

A mixture of I-35-1 (2.9 g, 15 mmol), Pd$_2$(dba)$_3$ (0.28 g, 0.31 mmol), and X-Phos (0.29 g, 0.62 mmol) in dry THF (30 mL) is degassed with argon for 10-15 min. To this mixture is added, dropwise, solution of LiHMDS in THF (32.5 mL, 32.6 mmol, 1M). The resulting mixture is then heated to 60° C. After 18 h, the reaction mixture is cooled to rt and 1M HCl (20 mL, 20 mmol) is added. The resulting solution is washed with MTBE (50 mL) and the organic layer is separated. The aqueous layer is made basic to pH~11 by addition of a 6M aqueous NaOH solution, and then extracted with EtOAc (3×). The combined organic layer is washed with water, dried over anhydrous MgSO$_4$, and concentrated under reduced pressure to afford 2.1 g of 2-[(2-amino-4-pyridyl)oxy]ethanol (I-35-2) which is used in subsequent steps without further purification.

To a stirred solution of I-35-2 (4.0 g, 24 mmol) in THF (40 mL) is added an aqueous solution of 2-chloroacetaldehyde (6.8 g, 48 mmol, 55% aqueous solution). The mixture is heated to 75° C. in a sealed tube for 18 h. The mixture is then cooled to ambient temperature and partitioned between EtOAc (3×50 mL) and saturated aqueous NaHCO$_3$ (100 mL). The combined organic layer is washed with brine (100 mL), dried over anhydrous MgSO$_4$, and concentrated under reduced pressure to afford 1.8 g of 7-(2-methoxyethoxy)imidazo[1,2-a]pyridine (I-35-3) which is used in subsequent steps without further purification.

To a stirred solution of I-35-3 (1.3 g, 6.8 mmol) in DMF (15 mL) is added NBS (1.2 g, 6.8 mmol) in one portion. The resulting mixture is stirred at ambient temperature for 5 min then diluted with saturated aqueous sodium thiosulphate (150 mL) and then extracted with EtOAc (3×50 mL).

The combined organic layer is washed with brine, dried over anhydrous MgSO$_4$, concentrated under reduced pressure. The residue is purified by flash silica gel column chromatography to afford 1.1 g of 3-bromo-7-(2-methoxyethoxy)imidazo[1,2-a]pyridine (I-35).

Synthesis of N-Cyclopropyl-4-methyl-3-(1H-pyrazol-4-yl)benzamide (I-36)

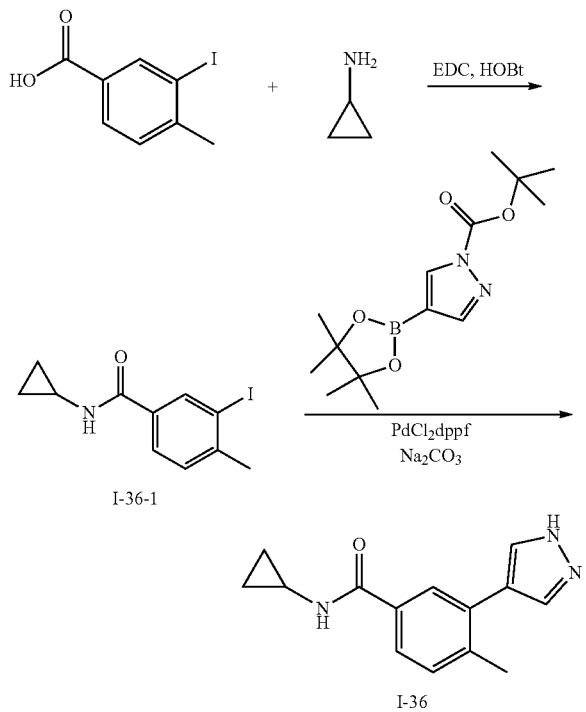

To a stirred solution of 3-iodo-4-methyl-benzoic acid (42 g, 160 mmol) in DMF (400 mL), at room temperature, is added EDC HCl (92 g, 481 mmol) followed by HOBt (32 g, 240 mmol). The reaction mixture is stirred for 30 min followed by the addition of cyclopropylamine (13.3 mL, 192 mmol) and DIPEA (140 mL, 802 mmol). After 16 h, the reaction is quenched with water and extracted with EtOAc. The combined organic layer is washed with brine, dried over anhydrous MgSO$_4$, and evaporated under reduced pressure. The crude material is washed with 20% EtOAc in hexane (200 mL) to afford 45 g of N-cyclopropyl-3-iodo-4-methyl-benzamide (I-36-1).

To a solution of I-36-1 (20 g, 66.4 mmol) in 1,4-dioxane (500 mL), at ambient temperature, is added tert-butyl 4-(4,4,5,5-tetramethyl-1,3,2-dioxaborolan-2-yl)pyrazole-1-carboxylate (23.4 g, 79.7 mmol) followed by Na$_2$CO$_3$ (21.1 g, 199 mmol) and water (150 mL). The reaction mixture is degassed and refilled with nitrogen two times. PdCl$_2$(dppf) (5.4 g, 6.6 mmol) is added and the reaction mixture is heated at 110° C. for 4 h. The reaction mixture is cooled and evaporated under reduced pressure. The crude residue is purified by flash column chromatography on silica gel (eluent with 3% MeOH in EtOAc) to yield 15.2 g of N-cyclopropyl-4-methyl-3-(1H-pyrazol-4-yl)benzamide (I-36).

The following intermediates are synthesized according to the general procedure described above using commercially available benzoic acids:

N-Cyclopropyl-2-fluoro-4-methyl-5-(1H-pyrazol-4-yl)benzamide (I-37)

4-Chloro-N-cyclopropyl-2-fluoro-5-(1H-pyrazol-4-yl)benzamide (I-38)

Starting benzoic acid for the synthesis of intermediate I-37 is made the following way:

Synthesis of 2-fluoro-5-iodo-4-methyl-benzoic Acid (I-1A)

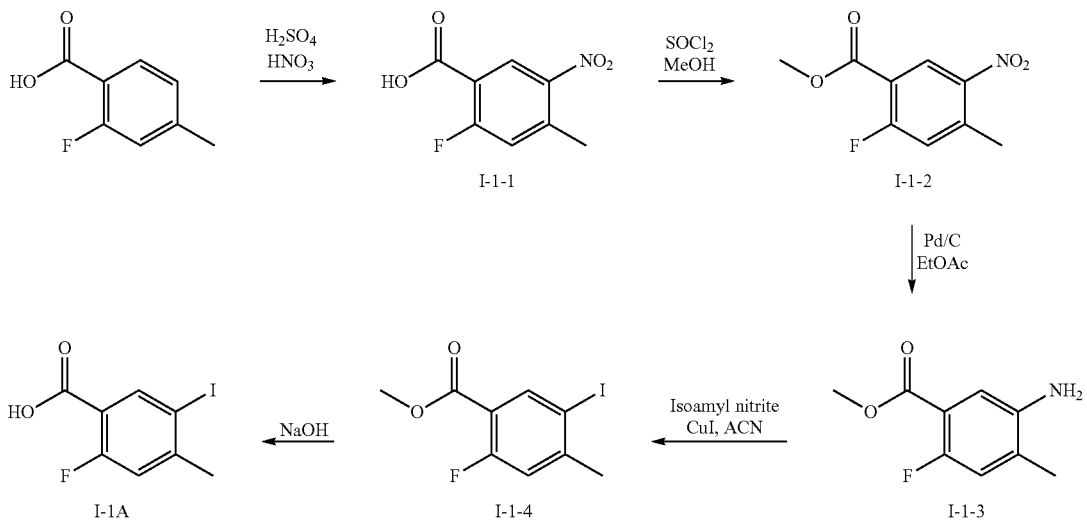

To a stirred solution of 2-fluoro-4-methyl benzoic acid (26 g, 168 mmol) in concentrated H₂SO₄ (260 mL) is dropwise added freshly prepared nitration mixture [concentrated H₂SO₄ (10.7 mL)+70% HNO₃ (11.9 mL)] at 0° C. over 45 min. The resultant solution is stirred for 3 h at 0° C. The reaction mixture is quenched with ice water. The resulting heterogeneous solution is extracted with ethyl acetate. The combined organic layer is washed with water, brine, dried over anhydrous MgSO₄, filtered and concentrated under reduced pressure to afford 30 g of crude 2-fluoro-4-methyl-5-nitro-benzoic acid (I-1-1).

To a stirred solution of I-1-1 (30 g, 150 mmol) in methanol (300 mL) is added thionyl chloride (22.5 mL, 301 mmol) dropwise at 10° C. The resultant solution is warmed to reflux. After 12 h, the solvent is concentrated under reduced pressure and the crude residue is partitioned between ethyl acetate and water. The organic layer is separated and washed with saturated NaHCO₃ solution, water, brine, dried over anhydrous MgSO₄, filtered and concentrated under reduced pressure to afford 30 g of methyl 2-fluoro-4-methyl-5-nitro-benzoate (I-1-2).

The solution of methyl I-1-2 (30 g, 141 mmol) in methanol (600 mL) was charged to a 2 liter Parr pressure vessel. Palladium, 10% on carbon (3 g, 28 mmol), is then added under nitrogen atmosphere. The Parr vessel is put under a hydrogen atmosphere (45 psi). After 12 h, the reaction mass is filtered through celite and the filtrate is concentrated under reduced pressure to afford 26 g of methyl 5-amino-2-fluoro-4-methyl-benzoate (I-1-3).

To a stirred solution of I-1-3 (26 g, 142 mmol) in acetonitrile (540 mL) at −5° C. is dropwise added isoamyl nitrite (21.7 g, 184 mmol). After 5 min, copper (I) iodide (56 g, 369 mmol) is added portion wise to the reaction mixture and the resultant mixture is slowly heated to 65° C. for 2 h. The solution is filtered through celite and the filtrate is concentrated under reduced pressure. Flash column chromatography (silical gel, eluent with 5% ethyl acetate in hexane) yields 20 g of methyl 2-fluoro-5-iodo-4-methyl-benzoate (I-1-4).

To a stirred solution of I-1-4 (20 g, 68 mmol) in THF:MeOH:H₂O (1:1:1, 300 mL) is added solid NaOH (4 g, 102 mmol) at room temperature. The resultant solution is stirred for 3 h at room temperature. The solvent is concentrated under reduced pressure and the residue is diluted with water (500 mL) and washed with ethyl acetate (2×150 mL). The pH of the aqueous layer is adjusted to pH 2 by addition of 10% aqueous HCl and then extracted with DCM (3×150 mL). The combined organic layer is washed with water (2×100 mL), brine (200 mL), dried over anhydrous MgSO₄, filtered and concentrated under reduced pressure to afford 2-fluoro-5-iodo-4-methyl-benzoic acid (I-1A).

Synthesis of Synthesis of N-Cyclopropyl-3-(1H-imidazol-4-yl)-4-methyl-benzamide (I-39)

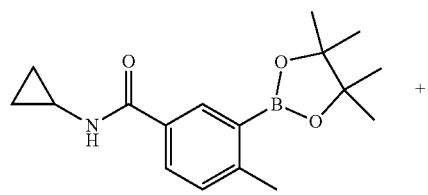

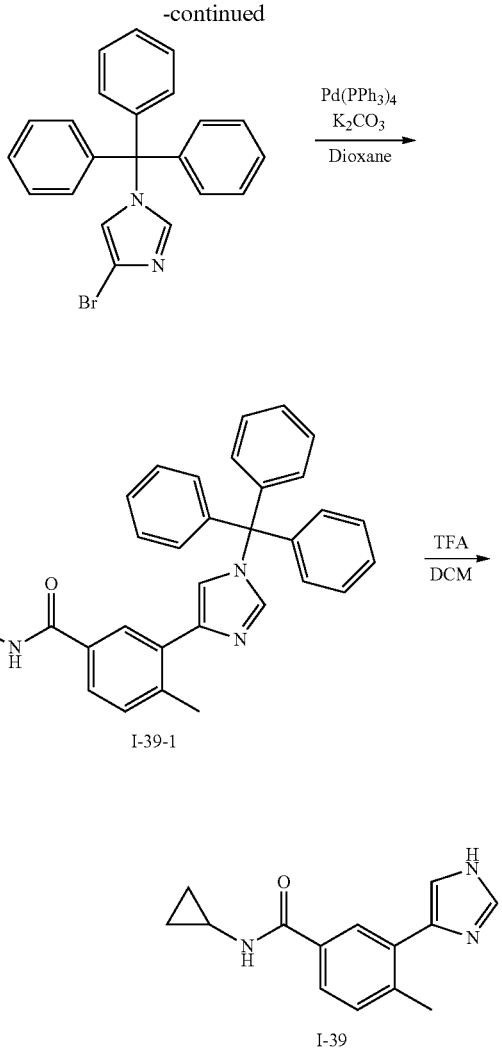

A mixture of N-Cyclopropyl-4-methyl-3-(4,4,5,5-tetramethyl-[1,3,2]dioxaborolan-2-yl)-benzamide (1.0 g; 3.2 mmol), 4-Bromo-1-trityl-1H-imidazole (1.4 g; 3.54 mmol), 2M K2CO3 solution in water (4.0 ml; 8.05 mmol), and tetrakis(triphenylphosphine)palladium(0) (428.0 mg; 0.37 mmol) in Dioxane (13.4 ml) is degassed and refilled with nitrogen in a microwave vial. The reaction is heated in a microwave reactor at 130° C. for 30 min. The mixture is diluted with water and extracted with EtOAc. The organic phase is washed with brine, dried over Na2SO4, filtered, and concentrated under reduced pressure. The resulting residue is purified by flash silica gel chromatography to provide N-Cyclopropyl-4-methyl-3-(1-trityl-1H-imidazol-4-yl)-benzamide I-39-1 (1.0 g).

To a solution of I-39-1 (1 g; 2.1 mmol) in dichloromethane (11.7 ml) is added TFA (2.0 ml). The mixture is stirred at rt for 2 h. An additional 0.5 mL of TFA was added and the reaction is stirred for another 1 h. The pH of the mixture is adjusted to pH 8 by the addition of a sat. solution of NaHCO₃. The mixture washed with brine, dried over Na2SO4, filtered, and concentrated under reduced pressure. The resulting residue is purified by flash silica gel column chromatography to provide the title compound (I-39) (500 mg).

The following intermediates are synthesized according to the general procedure described above using commercially available benzoic acids:
N-Cyclopropyl-2-fluoro-4-methyl-5-(1H-imidazol-4-yl) benzamide (I-39-2)

Synthesis of 3-Bromo-7-methoxy-imidazo[1,2-a] pyridine-6-carboxylic Acid Dimethylamide (I-40)

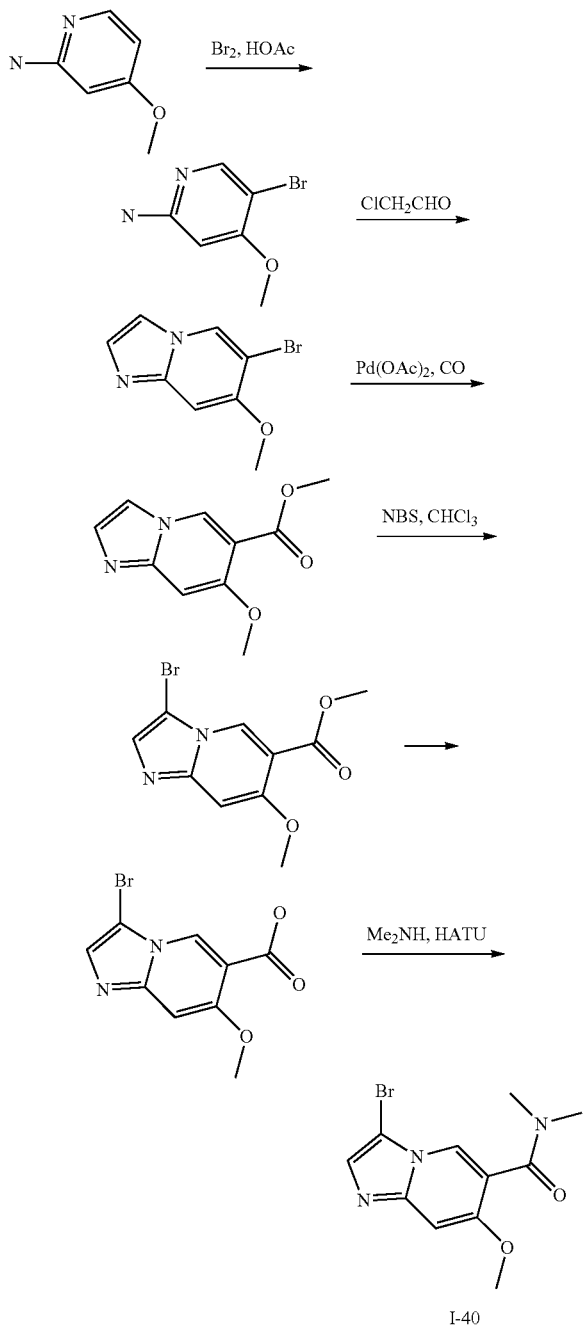

I-40

To a solution of 4-Methoxy-pyridin-2-ylamine (45 g; 0.362 mol; 1.0 eq.) in HOAc (1000 mL) is added a solution of Br$_2$ (57.9 g; 0.362 mol; 1.0 eq.) in HOAc (260 mL) dropwise within 0.5 h. A large amount of white solid is generated. The resultant mixture is stirred at 18° C. for 1.5 h. After filtration, the filter cake is taken up with EtOAc (1500 mL) and washed with sat. NaHCO$_3$ (500 mL×2), water (300 mL) and brine (200 mL), dried over Na$_2$SO$_4$, filtered and concentrated to afford 5-Bromo-4-methoxy-pyridin-2-ylamine (53.0 g; 0.261 mol) as a white solid, which is used in next step without purification.

To a solution of 5-Bromo-4-methoxy-pyridin-2-ylamine (53 g, 0.261 mol, 1.0 eq.) in EtOH:H2O=4:1 (500 mL) is added chloro-acetaldehyde (24.589 g, 0.313 mol, 1.2 eq.), then NaHCO$_3$ (26.3 g, 0.313 mol, 1.2 eq.) is added. The resultant mixture is heated to 90° C. for 4 h. After cooling to r.t., the organic solvent is evaporated. The residue is extracted with DCM (200 mL×3). The organic layer are combined, dried over Na$_2$SO$_4$, filtered and concentrated. The crude product is purified by silica gel chromatography (DCM:MeOH=50:1) to afford compound 6-Bromo-7-methoxy-imidazo[1,2-a]pyridine (39 g, 66%) as a brown solid.

To a solution of 6-Bromo-7-methoxy-imidazo[1,2-a]pyridine (34.9 g, 0.154 mol, 1.0 eq.) in MeOH (350 ml) and Toluene (350 ml) is added TEA (23 g, 0.231 mol, 1.5 eq.), then Pd(dppf)Cl$_2$ (11.2 g, 0.015 mol, 0.1 eq.) is added under N$_2$ atmosphere. The resultant mixture is heated to 80° C. under CO atmosphere (3 MPa) for 16 h. The solvent is removed under vacuum. The residue is purified by column chromatography (DCM) and washed with PE:EA=1:1 (20 mL) to afford 7-Methoxy-imidazo[1,2-a]pyridine-6-carboxylic acid methyl ester (20 g, 63%) as a brown solid.

To a solution of 7-Methoxy-imidazo[1,2-a]pyridine-6-carboxylic acid methyl ester (20 g, 97 mmol, 1.0 eq.) in CHCl$_3$ (400 ml) is added NBS (17 g, 97 mmol, 1.0 eq.) at −10° C. under N$_2$ atmosphere. The resultant solution is allowed to warm to 0° C. and stirred for 20 min. After diluted with DCM (400 mL), the resultant solution is washed with water (200 mL×2) and brine (300 mL). The organic layer is separated, dried over Na$_2$SO$_4$, filtered and concentrated. The residue is washed with a mixture solvent PE:EA=1:1 (500 mL) and DCM (100 mL) to afford compound 3-Bromo-7-methoxy-imidazo[1,2-a]pyridine-6-carboxylic acid methyl ester (15.5 g, 54 mmol) as a pale solid.

3-Bromo-7-methoxy-imidazo[1,2-a]pyridine-6-carboxylic acid methyl ester (2 g, 7 mmol) is dissolved in THF (40 mL), then 3.5 mL of aq. 6N HCl is added. The mixture is heated at 60° C. for 2 days. Additional 3.5 mL of 6N HCl is added. The reaction is heated for another day. After cooling down to rt, solvent is evaporated to afford the crude product 3-Bromo-7-methoxy-imidazo[1,2-a]pyridine-6-carboxylic acid as an HCL salt (2.2 g, 60%).

The above HCl salt of 3-Bromo-7-methoxy-imidazo[1,2-a]pyridine-6-carboxylic acid (2.2 g) is neutralize with Sat. NaHCO$_3$ until pH=7. The solid is filtered and rinsed with water. The solid is dried under high vacuum. It is then dissolved in DMF (20 mL), Et$_3$N (3 mL, 21 mmol) and dimethylamine HCl (700 mg, 8.6 mmol) are added, followed by HATU (2.4 g, 6.4 mmol). Stirring is continued at room temperature overnight. To the reaction is added water, extracted with EtOAc, washed with water, brine, dried over Na$_2$SO$_4$, filtered and concentrated. The residue is purified by silica gel chromatography (0-10% MeOH in DCM) to afford compound 3-Bromo-7-methoxy-imidazo[1,2-a]pyridine-6-carboxylic acid dimethylamide (I-40) (1.24 g, 76%).

Synthesis of N-Cyclopropyl-2-fluoro-4-methyl-5-[1-(6-piperidin-4-yl-imidazo[1,2-a]pyridin-3-yl)-1H-pyrazol-4-yl]-benzamide di-hydrochloride (I-41)

$H_2$ (50 psi) at 20° C. for 10 h. The mixture is filtered through a celite pad and washed with MeOH (1500 mL), the filtrate is concentrated in vacuo to give the crude product, which is purified by silica gel column chromatography (DCM: MeOH=300:1 to 20:1) to 4-Imidazo[1,2-a]pyridine-6-yl-piperidine-1-carboxylic acid tert-butyl ester (50 g, 165.9 mmol) as a brown oil.

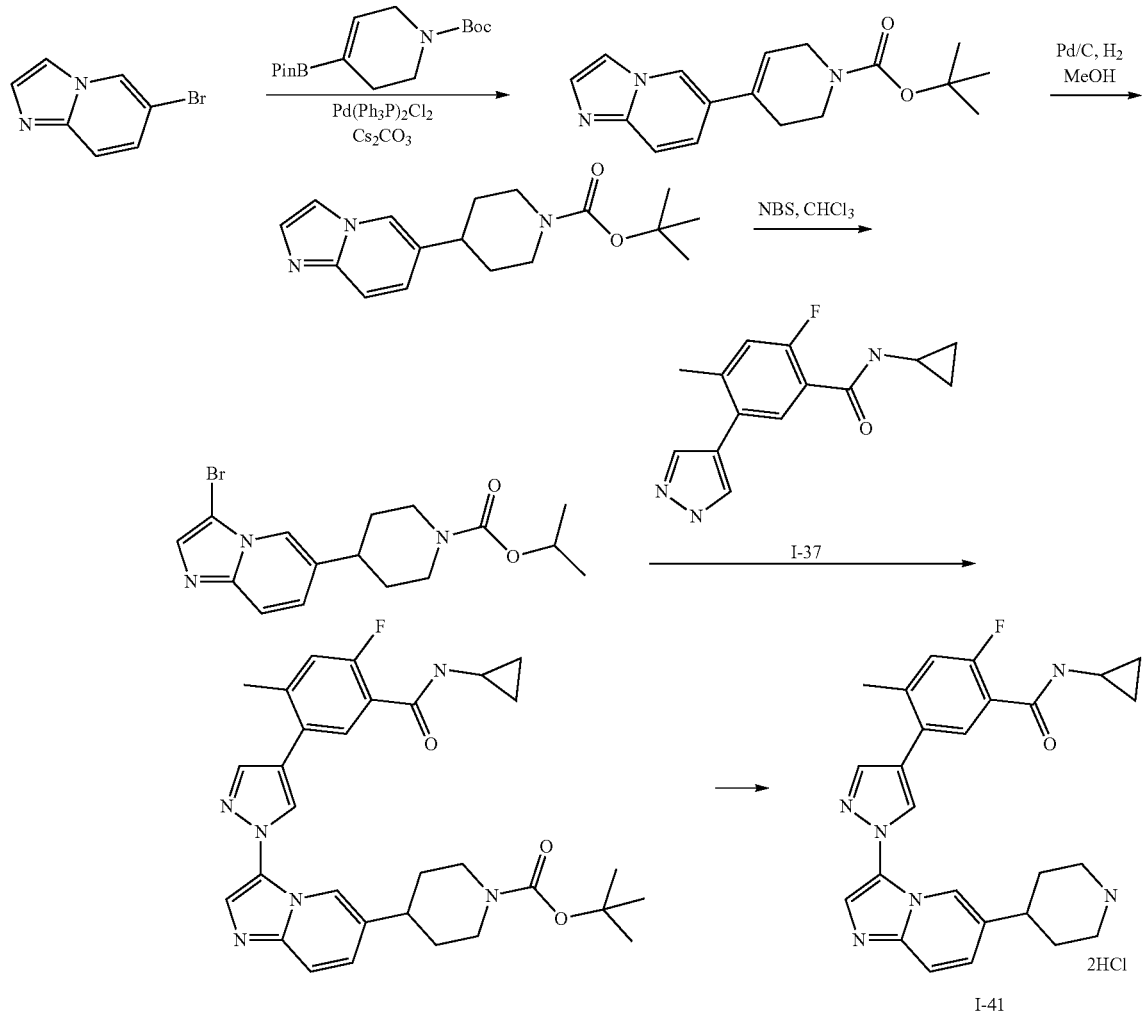

I-41

To a mixture of 6-Bromo-imidazo[1,2-a]pyridine (20 g, 0.102 mol, 1.0 eq), boronic ester (37.66 g, 0.122 mol, 1.2 eq) and $Cs_2CO_3$ (65.98 g, 0.203 mol, 2.0 eq) in Dioxane (300 mL) and $H_2O$ (30 mL) is added $Pd(PPh_3)_2Cl_2$ (7.13 g, 0.01 mol, 0.1 eq) at room temperature under $N_2$. The mixture is heated to 100° C. and stirred for 15 h under $N_2$. TLC and LCMS showed the reaction is completed. The reaction is filtered through a pad of celite and washed with DCM (3×500 mL). The filtrate is concentrated in vacuo to give the crude product, which is purified by silica gel column chromatography (DCM:MeOH=100:1 to 30:1) to afford 4-Imidazo[1,2-a]pyridine-6-yl-3,6-dihydro-2H-pyridine-1-carboxylic acid tert-butyl ester (26 g, 0.087 mol) as a brown oil.

To a solution of 4-Imidazo[1,2-a]pyridine-6-yl-3,6-dihydro-2H-pyridine-1-carboxylic acid tert-butyl ester (52 g, 173.7 mmol, 1.0 eq.) in MeOH (3000 mL) is added 10% Pd/C (20 g) under $Ar_2$. The reaction mixture is stirred under To a stirred solution of 4-Imidazo[1,2-a]pyridine-6-yl-piperidine-1-carboxylic acid tert-butyl ester (1.5 g, 5 mmol) in chloroform (15 mL) is added NBS (890 mg, 5 mmol). The solution is stirred at room temperature for 2 h and then concentrated. The residue is diluted with EtOAc, washed with $NaHCO_3$, $H_2O$, brine and concentrated to give a residue, which is purified by flash chromatography (25 g, 0-80% EtOAc/heptane), followed by reverse phase chromatography (100 g, 10-100% H2O/ACN, both containing 0.5% formic acid) to afford compound 4-(3-Bromo-imidazo[1,2-a]pyridine-6-yl)-piperidine-1-carboxylic acid tert-butyl (1.6 g, 85%).

4-(3-Bromo-imidazo[1,2-a]pyridine-6-yl)-piperidine-1-carboxylic acid tert-butyl (1.55, 4.1 mmol), I-37 (1.3 g, 4.9 mmol), CuI (388 mg, 2.0 mmol), $K_3PO_4$ (1.7 g, 8.2 mmol) and trans-dimethylaminocyclohexane (463 mg, 3.3 mmol) are suspended in DMF (15 mL) and the mixture is flushed with Ar. The mixture is then heated to 65° C. and allowed to stir overnight. The mixture is cooled to room temperature, diluted with EtOAc, washed with H₂O, brine and concentrated to give a residue, which is purified by flash chromatography (50 g, 0-100% EtOAc/heptane) to afford compound 4-{3-[4-(5-Cyclopropylcarbamoyl-4-fluoro-2-methyl-phenyl)-pyrazol-1-yl]-imidazo[1,2-a]pyridine-6-yl}-piperidine-1-carboxylic acid tert-butyl ester (1.4 g, 62%).

To a stirred and cooled (0° C.) solution of 4-{3-[4-(5-Cyclopropylcarbamoyl-4-fluoro-2-methyl-phenyl)-pyrazol-1-yl]-imidazo[1,2-a]pyridine-6-yl}-piperidine-1-carboxylic acid tert-butyl ester (1.4 g, 2.5 mmol) in DCM (15 mL) and MeOH (5 mL) is added 4N HCl in dioxane (10 mL).

The mixture is allowed to warm to room temperature overnight. The solution is concentrated to give a residue, which is dried in vacuum to afford compound 1-41 (1.32 g, 99%)

Final Compounds

Example 1: 3-[4-(5-Cyclopropylcarbamoyl-4-fluoro-2-methyl-phenyl)-pyrazol-1-yl]-7-methoxy-imidazo[1,2-a]pyridine-6-carboxylic Acid Dimethylamide

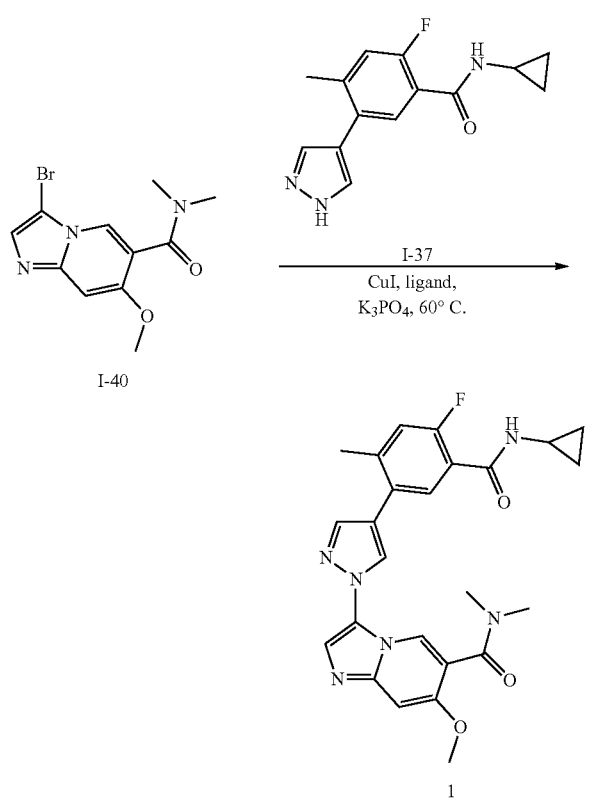

I-40 (217 mg, 0.7 mmol), I-37 (170 mg, 0.7 mmol), CuI (50 mg, 0.3 mmol), K₃PO₄ (278 mg, 1.3 mmol) and trans-dimethylaminocyclohexane (74 mg, 0.5 mmol) are suspended in DMF (10 mL) and the mixture flushed with Ar. The mixture is then heated to 60° C. for 6 h, then at room temperature overnight. The reaction is filtered, rinsed with EtOAc and concentrated. To the residue is added water, extracted with EtOAc, washed with water and concentrated. The residue is purified by reverse phase HPLC (5-50%% ACN in water with formic acid). Pure fractions are combined and concentrated. The residue is dissolved in MeOH and passed through a bicarbonate cartridge to afford 1 as a white solid (75 mg, 24%).

Example 2: 3-[4-(5-Cyclopropylcarbamoyl-4-fluoro-2-methyl-phenyl)-pyrazol-1-yl]-imidazo[1,2-a]pyridine-6-carboxylic Acid Methyl Ester

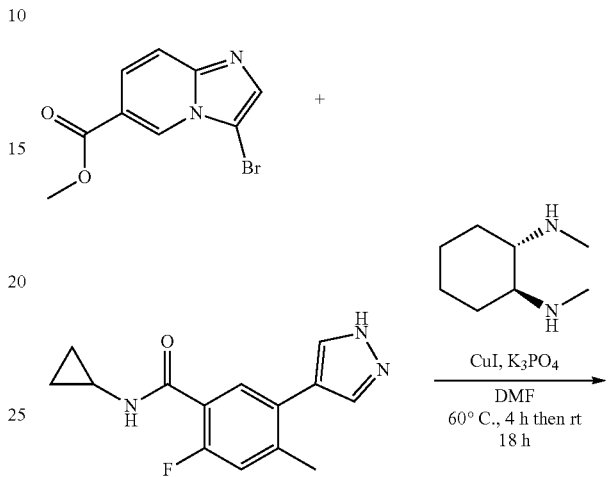

A mixture of 3-bromo-imidazo[1,2-a]pyridine-6-carboxylic acid methyl ester (492 mg, 1.93 mmol), I-37 (500 mg, 1.93 mmol), potassium phosphate (819 mg, 3.86 mmol), trans-N,N'-dimethyl-cyclohexane-1,2-diamine (0.2 ml, 1.54 mmol) in anhydrous DMF (8.0 ml) is degassed with nitrogen. To this mixture is added CuI (147 mg, 0.77 mmol). The reaction is placed under nitrogen and the reaction is heated at 60° C. for 4 h. The mixture is then cooled to room temperature and stirred for 18 h. The reaction is then diluted with water and extracted with EtOAc (3×). The organic layers are combined, washed with water, then brine, and dried over sodium sulfate. The solution is then filtered and concentrated under reduced pressure. The resulting residue is purified by flash silica gel chromatography to provide 374 mg of the title compound (2).

The following compounds are synthesized in a similar fashion to Example 2 using commercially available heteroaryl bromide and/or intermediates described herein:

3-[4-(5-Cyclopropylcarbamoyl-2-methyl-phenyl)-imidazol-1-yl]-imidazo[1,2-a]pyridine-6-carboxylic acid methylamide (3)

4-Chloro-N-cyclopropyl-2-fluoro-5-(1-imidazo[1,2-a]pyridin-3-yl-1H-pyrazol-4-yl)-benzamide (5)

4-Chloro-N-cyclopropyl-2-fluoro-5-(1-imidazo[1,2-a]pyrazin-3-yl-1H-pyrazol-4-yl)-benzamide (6)

5-[1-(2-Acetylamino-thiazol-5-yl)-1H-pyrazol-4-yl]-4-chloro-N-cyclopropyl-2-fluoro-benzamide (7)

5-[1-(8-Amino-imidazo[1,2-a]pyridin-3-yl)-1H-pyrazol-4-yl]-4-chloro-N-cyclopropyl-2-fluoro-benzamide (8)

4-Chloro-N-cyclopropyl-2-fluoro-5-[1-(6-methoxy-imidazo[1,2-a]pyrazin-3-yl)-1H-pyrazol-4-yl]-benzamide (9)

4-Chloro-N-cyclopropyl-2-fluoro-5-{1-[6-(2-methyl-propane-2-sulfonyl)-imidazo[1,2-a]pyridin-3-yl]-1H-pyrazol-4-yl}-benzamide (10)

4-Chloro-N-cyclopropyl-2-fluoro-5-(1-pyrazolo[1,5-a]pyridin-3-yl-1H-pyrazol-4-yl)-benzamide (11)

4-Chloro-N-cyclopropyl-2-fluoro-5-(1-imidazo[1,2-a]pyrazin-6-yl-1H-pyrazol-4-yl)-benzamide (12). Note: Obtained as a side-product starting from 6-bromo-3-iodo-imidazo[1,2-a]pyrazine, and reaction is conducted at 100° C. for 18 h.

N-Cyclopropyl-3-(1-imidazo[1,2-a]pyrazin-3-yl-1H-pyrazol-4-yl)-4-methyl-benzamide (13)

3-[1-(2-Acetylamino-thiazol-5-yl)-1H-pyrazol-4-yl]-N-cyclopropyl-4-methyl-benzamide (14)

N-Cyclopropyl-3-(1-imidazo[1,2-a]pyridin-3-yl-1H-pyrazol-4-yl)-4-methyl-benzamide (15)

3-[1-(2-Acetylamino-thiazol-5-yl)-1H-imidazol-4-yl]-N-cyclopropyl-4-methyl-benzamide (17)

N-Cyclopropyl-4-methyl-3-{1-[6-(2-methyl-propane-2-sulfonyl)-imidazo[1,2-a]pyridin-3-yl]-1H-pyrazol-4-yl}-benzamide (19)

N-Cyclopropyl-4-methyl-3-{1-[6-(2-methyl-propane-2-sulfonyl)-imidazo[1,2-a]pyridin-2-yl]-1H-pyrazol-4-yl}-benzamide (20). Note: Obtained as a side-product from synthesis of 19 when reaction is conducted at 100° C. for 18 h.

4-Chloro-N-cyclopropyl-2-fluoro-5-[1-(6-methanesulfonyl-imidazo[1,2-a]pyridin-3-yl)-1H-pyrazol-4-yl]-benzamide (21)

N-Cyclopropyl-4-methyl-3-{1-[6-(2-methyl-propane-2-sulfonyl)-imidazo[1,2-a]pyridin-3-yl]-1H-imidazol-4-yl}-benzamide (22)

N-Cyclopropyl-4-methyl-3-{1-[6-(oxetan-3-ylsulfanyl)-imidazo[1,2-a]pyridin-3-yl]-1H-pyrazol-4-yl}-benzamide (23)

5-[4-(2-Chloro-5-cyclopropylcarbamoyl-4-fluoro-phenyl)-pyrazol-1-yl]-thiazole-2-carboxylic acid amide (25)

5-[4-(2-Chloro-5-cyclopropylcarbamoyl-4-fluoro-phenyl)-pyrazol-1-yl]-thiazole-2-carboxylic acid methylamide (26)

N-Cyclopropyl-3-[1-(6-ethanesulfonyl-imidazo[1,2-a]pyridin-3-yl)-1H-pyrazol-4-yl]-4-methyl-benzamide (27)

N-Cyclopropyl-3-{1-[7-methoxy-6-(2-methyl-propane-2-sulfonyl)-imidazo[1,2-a]pyridin-2-yl]-1H-pyrazol-4-yl}-4-methyl-benzamide (28). Note: Obtained as a side-product during synthesis of 35 when reaction is conducted at 100° C. for 18 h.

N-Cyclopropyl-4-methyl-3-{1-[5-(2-methyl-propane-2-sulfonyl)-pyrazolo[1,5-a]pyridin-3-yl]-1H-pyrazol-4-yl}-benzamide (29)

N-Cyclopropyl-3-[1-(6-ethanesulfonyl-7-methoxy-imidazo[1,2-a]pyridin-2-yl)-1H-pyrazol-4-yl]-4-methyl-benzamide (30). Note: Obtained as a side-product when reaction is conducted at 100° C. for 18 h.

N-Cyclopropyl-3-[1-(7-ethoxy-imidazo[1,2-a]pyridin-3-yl)-1H-pyrazol-4-yl]-4-methyl-benzamide (31)

N-Cyclopropyl-2-fluoro-5-(1-imidazo[1,2-a]pyridin-3-yl-1H-pyrazol-4-yl)-4-methyl-benzamide (32)

N-Cyclopropyl-2-fluoro-4-methyl-5-{1-[6-(2-methyl-propane-2-sulfonyl)-imidazo[1,2-a]pyridin-3-yl]-1H-pyrazol-4-yl}-benzamide (33)

N-Cyclopropyl-2-fluoro-5-[1-(6-methoxy-imidazo[1,2-a]pyrazin-3-yl)-1H-pyrazol-4-yl]-4-methyl-benzamide (34)

N-Cyclopropyl-3-{-1-[7-methoxy-6-(2-methyl-propane-2-sulfonyl)-imidazo[1,2-a]pyridin-3-yl]-1H-pyrazol-4-yl}-4-methyl-benzamide (35)

N-Cyclopropyl-2-fluoro-4-methyl-5-{1-[6-(morpholine-4-sulfonyl)-imidazo[1,2-a]pyridin-3-yl]-1H-pyrazol-4-yl}-benzamide (36)

N-Cyclopropyl-4-methyl-3-{1-[6-(morpholine-4-sulfonyl)-imidazo[1,2-a]pyridin-3-yl]-1H-pyrazol-4-yl}-benzamide (37)

N-Cyclopropyl-4-methyl-3-{1-[6-(4-methyl-piperazine-1-sulfonyl)-imidazo[1,2-a]pyridin-3-yl]-1H-pyrazol-4-yl}-benzamide (38)

N-Cyclopropyl-2-fluoro-4-methyl-5-{-1-[6-(4-methyl-piperazine-1-sulfonyl)-imidazo[1,2-a]pyridin-3-yl]-1H-pyrazol-4-yl}-benzamide (39)

3-[4-(5-Cyclopropylcarbamoyl-2-methyl-phenyl)-imidazol-1-yl]-imidazo[1,2-a]pyridine-6-carboxylic acid dimethylamide (41)

3-(1'-tert-Butyl-1'H-[1,4']bipyrazolyl-4-yl)-N-cyclopropyl-4-methyl-benzamide (42)

N-Cyclopropyl-4-methyl-3-(1-thiazol-5-yl-1H-pyrazol-4-yl)-benzamide (43)

3-[1-(2-Cyclobutoxy-thiazol-5-yl)-1H-pyrazol-4-yl]-N-cyclopropyl-4-methyl-benzamide (44)

3-{1-[2-(Cyclopropanecarbonyl-amino)-thiazol-5-yl]-1H-pyrazol-4-yl}-N-cyclopropyl-4-methyl-benzamide (45)

N-Cyclopropyl-4-methyl-3-[1-(2-morpholin-4-yl-thiazol-5-yl)-1H-pyrazol-4-yl]-benzamide (46)

N-Cyclopropyl-4-methyl-3-[1-(2-phenyl-thiazol-5-yl)-1H-pyrazol-4-yl]-benzamide (47)

N-Cyclopropyl-4-methyl-3-{1-[2-(2-oxo-2H-pyridin-1-yl)-thiazol-5-yl]-1H-pyrazol-4-yl}-benzamide (48)

N-Cyclopropyl-4-methyl-3-[1-(2-pyrrolidin-1-yl-thiazol-5-yl)-1H-pyrazol-4-yl]-benzamide (49)

N-Cyclopropyl-4-methyl-3-[1-(2-piperidin-1-yl-thiazol-5-yl)-1H-pyrazol-4-yl]-benzamide (50)

N-Cyclopropyl-3-[1-(2-hydroxymethyl-3-methyl-3H-imidazol-4-yl)-1H-pyrazol-4-yl]-4-methyl-benzamide (53)

N-Cyclopropyl-4-methyl-3-[1-(5-methyl-[1,3,4]thiadiazol-2-yl)-1H-pyrazol-4-yl]-benzamide (54)

N-Cyclopropyl-3-[1-(2,3-dimethyl-3H-imidazol-4-yl)-1H-pyrazol-4-yl]-4-methyl-benzamide (55)

Example 16: N-Cyclopropyl-3-(1-imidazo[1,2-a]pyridin-3-yl-1H-imidazol-4-yl)-4-methyl-benzamide

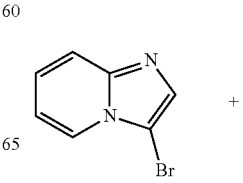

-continued

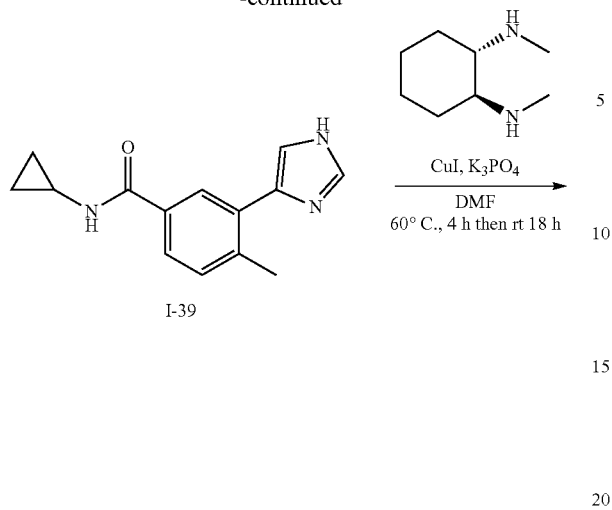

I-39

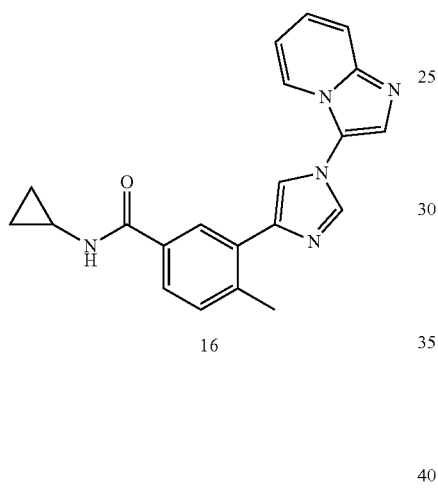

16

Example 56: 3-[4-(5-Cyclopropylcarbamoyl-4-fluoro-2-methyl-phenyl)-pyrazol-1-yl]-imidazo[1,2-a]pyridine-6-carboxylic Acid

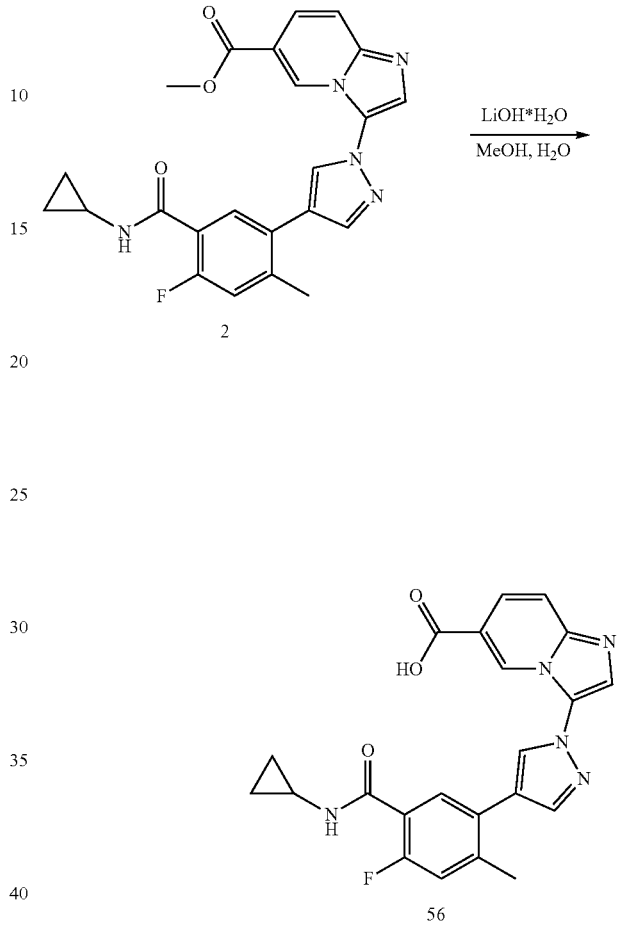

2

56

A mixture of 3-bromo-imidazo[1,2-a]pyridine-6-carboxylic acid methyl ester (43 mg, 0.22 mmol), I-39 (0.63 mg, 0.26 mmol), potassium phosphate (0.93 mg, 0.44 mmol), trans-N,N'-dimethyl-cyclohexane-1,2-diamine (0.03 mL, 0.18 mmol) in anhydrous DMF (1.0 ml) is degassed with nitrogen. To this mixture is added CuI (0.17 mg, 0.09 mmol). The reaction is placed under nitrogen and the reaction is heated at 100° C. for 24 h. The mixture is then cooled to room temperature, diluted with water and extracted with EtOAc (3×50 mL). The organic layers are combined, washed with water, then brine, and dried over sodium sulfate. The solution is then filtered and concentrated under reduced pressure. The resulting residue is purified by flash silica gel chromatography to provide 0.17 mg of the title compound (16).

The following compounds are synthesized in a similar fashion to Example 16 using commercially available heteroaryl bromide and/or intermediates described herein:

3-[4-(5-Cyclopropylcarbamoyl-2-methyl-phenyl)-imidazol-1-yl]-imidazo[1,2-a]pyridine-6-carboxylic acid methyl ester (40)

To a suspension of 2 (354 mg, 0.82 mmol) in methanol (15 ml) and water (5 ml) is added lithium hydroxide monohydrate (274 mg, 6.53 mmol). The reaction gradually turns clear after 2 h and is allowed to stir for 18 h. The reaction is then concentrated under reduced pressure. To the residue is added 2M aq. HCl (3 mL) and the mixture is concentrated to provide 610 mg of the title compound (56). The residue is used in subsequent steps without further purification.

The following compounds are synthesized in a similar fashion to the procedure described in Example 56 using intermediates described herein:

3-[4-(5-Cyclopropylcarbamoyl-2-methyl-phenyl)-pyrazol-1-yl]-imidazo[1,2-a]pyridine-6-carboxylic acid (57)

3-[4-(5-Cyclopropylcarbamoyl-2-methyl-phenyl)-imidazol-1-yl]-imidazo[1,2-a]pyridine-6-carboxylic acid (58)

Example 59: 3-[4-(5-Cyclopropylcarbamoyl-4-fluoro-2-methyl-phenyl)-pyrazol-1-yl]-imidazo[1,2-a]pyridine-6-carboxylic Acid (2-hydroxy-ethyl)-amide

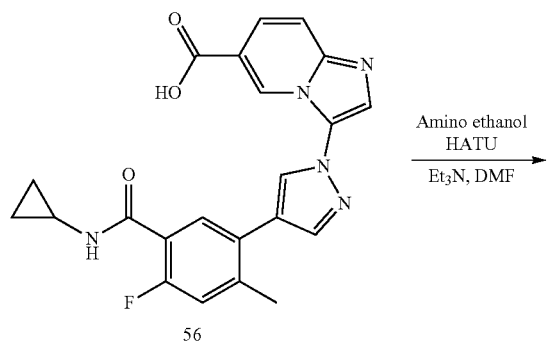

To a stirred solution of 56 (178 mg, 56% purity, 0.24 mmol) in DMF (3.7 ml) is added Et₃N (0.10 mL, 0.72 mmol), aminoethanol (29 mg, 0.48 mmol), and HATU (136 mg, 0.36 mmol). After 18 h, the reaction is purified by reversed phase HPLC followed by flash silica gel column chromatography to provide 82 mg of the titled compound (59).

The following compounds are synthesized in a similar fashion to Example 59 using commercially available amines:

3-[4-(5-Cyclopropylcarbamoyl-4-fluoro-2-methyl-phenyl)-pyrazol-1-yl]-imidazo[1,2-a]pyridine-6-carboxylic acid (2-methylamino-ethyl)-amide (60)

3-[4-(5-Cyclopropylcarbamoyl-2-methyl-phenyl)-pyrazol-1-yl]-imidazo[1,2-a]pyridine-7-carboxylic acid (2-hydroxy-ethyl)-amide (61)

3-[4-(5-Cyclopropylcarbamoyl-2-methyl-phenyl)-pyrazol-1-yl]-imidazo[1,2-a]pyridine-7-carboxylic acid amide (62)

3-[4-(5-Cyclopropylcarbamoyl-2-methyl-phenyl)-pyrazol-1-yl]-imidazo[1,2-a]pyridine-7-carboxylic acid (2-methylamino-ethyl)-amide (63)

N-Cyclopropyl-4-methyl-3-{1-[6-(morpholine-4-carbonyl)-imidazo[1,2-a]pyridin-3-yl]-1H-pyrazol-4-yl}-benzamide (64)

N-Cyclopropyl-4-methyl-3-{1-[6-(4-methyl-piperazine-1-carbonyl)-imidazo[1,2-a]pyridin-3-yl]-1H-pyrazol-4-yl}-benzamide (65)

3-[4-(5-Cyclopropylcarbamoyl-2-methyl-phenyl)-pyrazol-1-yl]-imidazo[1,2-a]pyridine-6-carboxylic acid dimethylamide (66)

3-[4-(5-Cyclopropylcarbamoyl-2-methyl-phenyl)-pyrazol-1-yl]-imidazo[1,2-a]pyridine-6-carboxylic acid methylamide (67)

3-[4-(5-Cyclopropylcarbamoyl-2-methyl-phenyl)-pyrazol-1-yl]-imidazo[1,2-a]pyridine-7-carboxylic acid methylamide (68)

3-[4-(5-Cyclopropylcarbamoyl-4-fluoro-2-methyl-phenyl)-pyrazol-1-yl]-imidazo[1,2-a]pyridine-6-carboxylic acid dimethylamide (69)

N-Cyclopropyl-2-fluoro-4-methyl-5-{1-[6-(4-methyl-piperazine-1-carbonyl)-imidazo[1,2-a]pyridin-3-yl]-1H-pyrazol-4-yl}-benzamide (70)

Example 71: N-Cyclopropyl-2-fluoro-5-{1-[6-(1-hydroxy-ethyl)-imidazo[1,2-a]pyridin-3-yl]-1H-pyrazol-4-yl}-4-methyl-benzamide

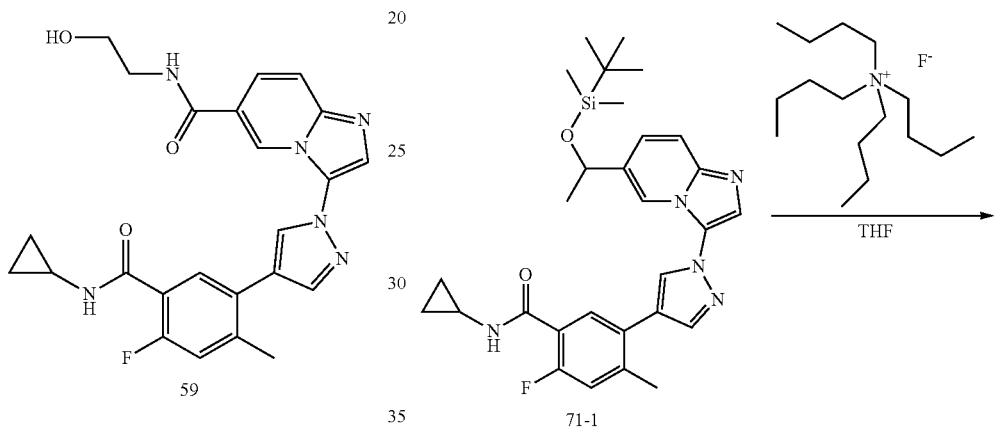

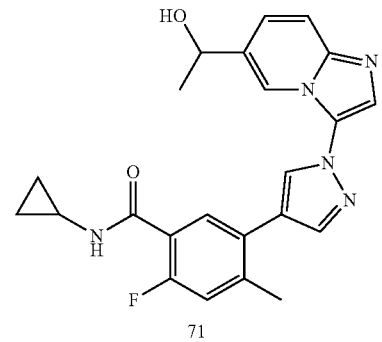

5-(1-{6-[1-(tert-Butyl-dimethyl-silanyloxy)-ethyl]-imidazo[1,2-a]pyridin-3-yl}-1H-pyrazol-4-yl)-N-cyclopropyl-2-fluoro-4-methyl-benzamide (71-1) is synthesized according to the Example 2 using intermediate I-30.

To a stirred solution of 71-1 (100 mg, 0.16 mmol) in THF (4 mL) is added tetrabutylammonium fluoride as a solution in THF (1M, 160 µL, 0.16 mmol). The resulting solution is stirred at room temperature for 2.5 h, and then concentrated under reduced pressure. The resulting residue is purified by flash silica gel chromatography. The isolated material was further purified by preparative reverse phase chromatography to provide 66 mg of the title compound (71).

The following compounds are synthesized in a similar fashion as the procedure described in Example 71 using intermediates described herein.

N-Cyclopropyl-3-{1-[6-(1-hydroxy-ethyl)-imidazo[1,2-a]pyridin-3-yl]-1H-pyrazol-4-yl}-4-methyl-benzamide (72)

N-Cyclopropyl-3-(1-{6-[hydroxy-(tetrahydro-pyran-4-yl)-methyl]-imidazo[1,2-a]pyridin-3-yl}-1H-pyrazol-4-yl)-4-methyl-benzamide (73)

N-Cyclopropyl-3-{1-[6-(1-hydroxy-ethyl)-imidazo[1,2-a]pyridin-3-yl]-1H-imidazol-4-yl}-4-methyl-benzamide (74)

N-Cyclopropyl-2-fluoro-5-{1-[6-(1-hydroxy-1-methyl-ethyl)-imidazo[1,2-a]pyridin-3-yl]-1H-pyrazol-4-yl}-4-methyl-benzamide (75)

Example 76: 3-[1-(6-Acetyl-imidazo[1,2-a]pyridin-3-yl)-1H-pyrazol-4-yl]-N-cyclopropyl-4-methyl-benzamide

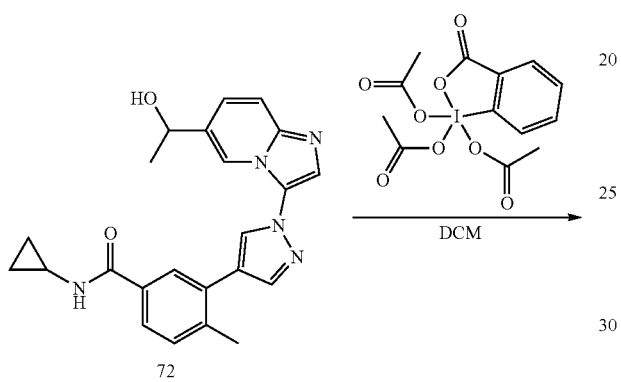

Example 77: N-Cyclopropyl-4-methyl-3-{1-[6-(oxetane-3-sulfonyl)-imidazo[1,2-a]pyridin-3-yl]-1H-pyrazol-4-yl}-benzamide

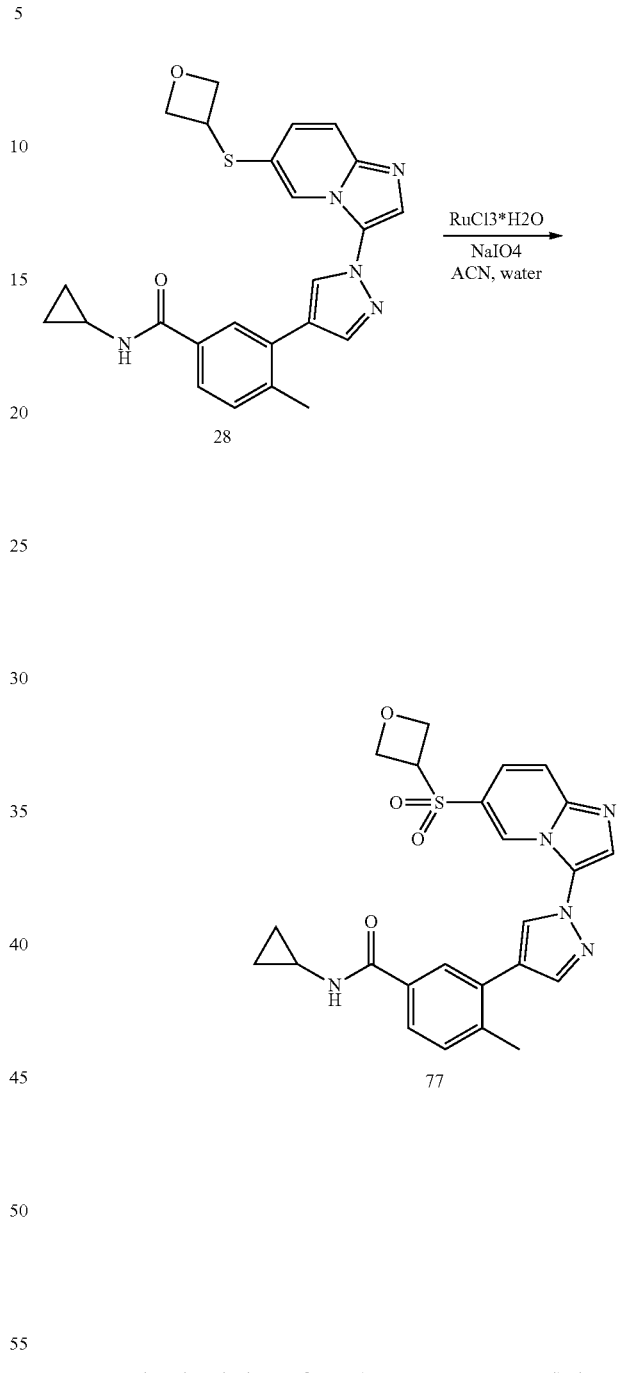

To a solution of 72 (660 mg, 1.6 mmol) in anhydrous DCM (30 mL) is added Dess-Martin reagent (725 mg, 1.70 mmol). After 30 min, the reaction is diluted with a saturated aqueous NaHCO₃ solution (5 mL), and stirred for 20 min. The mixture is filtered through celite, and the phases are separated. The organic layer is washed with brine (50 mL), dried over MgSO₄, filtered, and concentrated under reduced pressure. The residue is purified by flash silica gel column chromatography to provide 618 mg of the title compound (76).

To a stirred solution of 28 (70 mg, 0.16 mmol) in a mixture of acetonitrile (2.0 mL) and water (1.0 mL) is added ruthenium(III)chloride hydrate (2 mg, 0.01 mmol) and sodium metaperiodate (202 mg, 0.94 mmol). After 1 h, the reaction is diluted with EtOAc (10 mL) and water (5 mL). The layers are separated and the organic layer is extracted with EtOAc (3×), washed with brine (5 mL), dried over Na₂SO₄, filtered, and concentrated under reduced pressure. The resulting residue is purified by reversed phase HPLC (29-49% ACN in water with NH₄HCO₃) to provide 11 mg of the title compound (77).

111

Example 78: N-Cyclopropyl-3-{1-[7-hydroxy-6-(2-methyl-propane-2-sulfonyl)-imidazo[1,2-a]pyridin-2-yl]-1H-pyrazol-4-yl}-4-methyl-benzamide

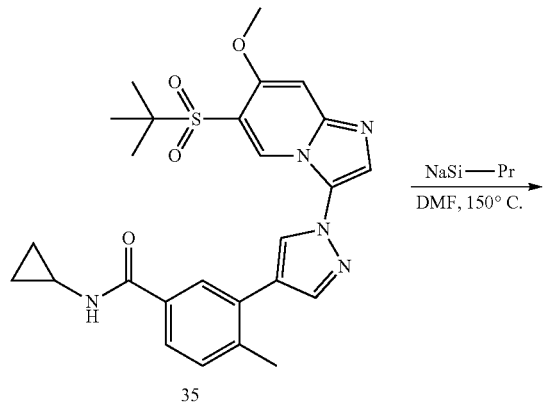

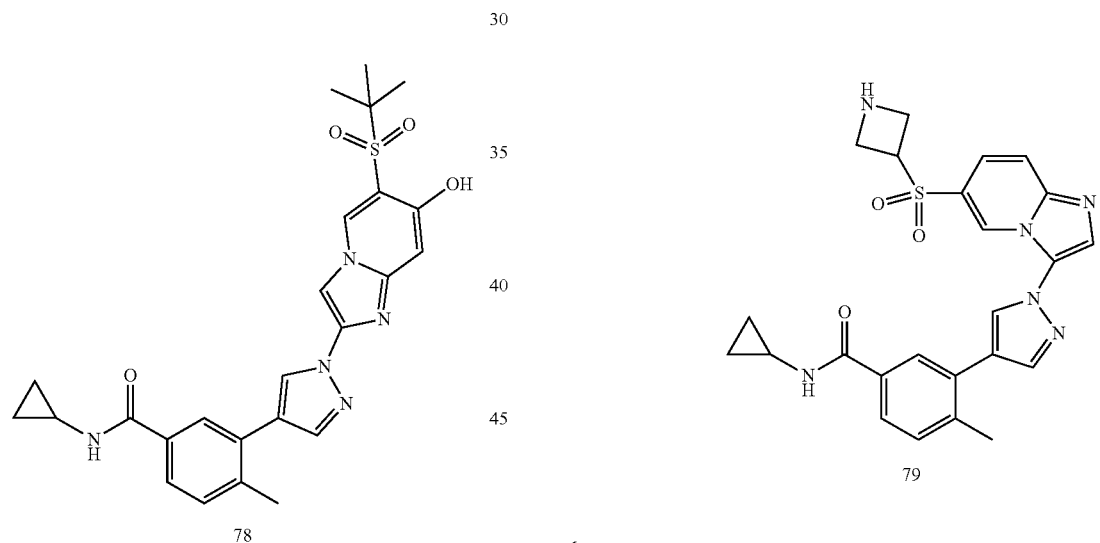

To a stirred solution of 35 (200 mg, 0.39 mmol) in DMF (5.0 mL) is added NaSi—Pr (387 mg, 3.94 mmol). The reaction is stirred at 150° C. for 1 h. The reaction is cooled to room temperature and concentrated under reduced pressure. The resulting residue is purified by reversed phase chromatography to provide 35 mg of the title compound (78).

112

Example 79: 3-{1-[6-(Azetidine-3-sulfonyl)-imidazo[12-a]pyridin-3-yl]-1H-pyrazol-4-yl}-N-cyclopropyl-4-methyl-benzamide

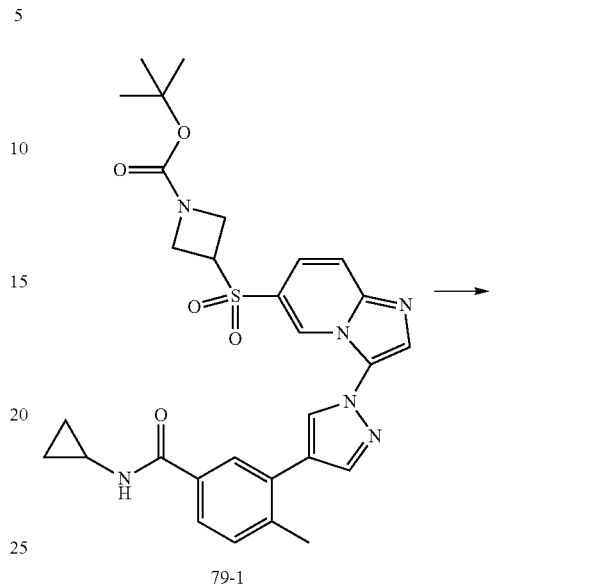

3-{3-[4-(5-Cyclopropylcarbamoyl-2-methyl-phenyl)-pyrazol-1-yl]-imidazo[1,2-a]pyridine-6-sulfonyl}-azetidine-1-carboxylic acid tert-butyl ester (79-1) is synthesized according to the Example 2 using intermediates described herein.

To a stirred solution of 79-1 (15 mg, 0.03 mmol) in MeOH (1.0 mL) is added a solution of 4M HCl in dioxane (130 μL, 0.52 mmol). The reaction is stirred at room temperature for 18 h, and then concentrated under reduced pressure. The resulting residue is purified by preparative reversed phase HPLC to provide 10 mg of the title compound (79).

The following compound is synthesized in a similar fashion as described in Example 79 using intermediates described herein.

N-Cyclopropyl-4-methyl-3-{1-[6-(piperidine-4-sulfonyl)-imidazo[1,2-a]pyridin-3-yl]-1H-pyrazol-4-yl}-benzamide (80)

Example 81: N-Cyclopropyl-2-fluoro-5-{1-[6-(1-hydroxy-ethyl)-imidazo[1,2-a]pyridin-3-yl]-1H-pyrazol-4-yl}-4-methyl-benzamide Example 82: N-Cyclopropyl-3-{1-[6-(1-hydroxy-ethyl)-imidazo[1,2-a]pyridin-3-yl]-1H-pyrazol-4-yl}-4-methyl-benzamide

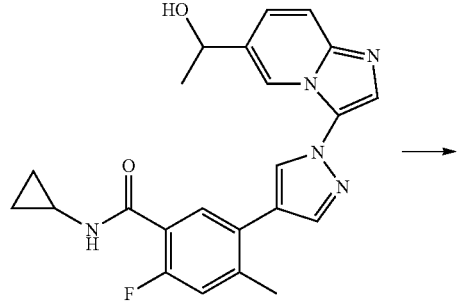

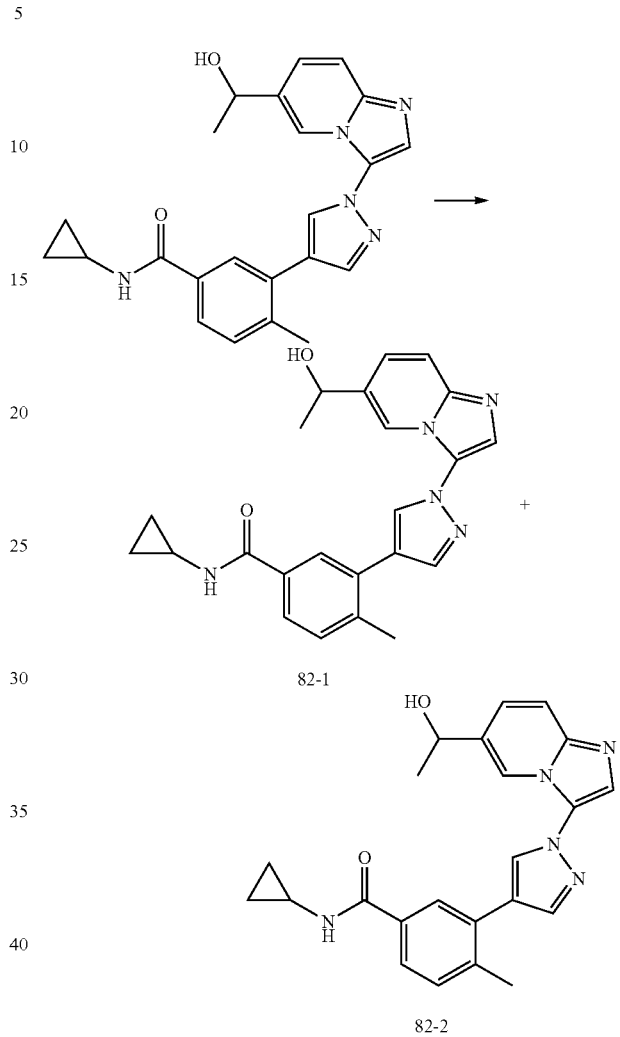

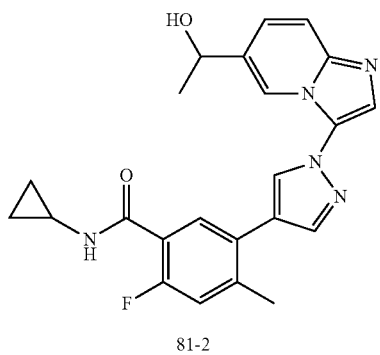

81-2

A sample of 50 (250 mg, 0.6 mmol) is separated by chiral hplc (ChiralCel OJ-H 20×250 mm, 22% EtOH:Heptane, 10 ml/min, 38 C). The first peak to elute is assigned as 81-1 (52 mg) and the second peak as 81-2 (56 mg).

A sample of N-Cyclopropyl-3-{1-[6-(1-hydroxy-ethyl)-imidazo[1,2-a]pyridin-3-yl]-1H-pyrazol-4-yl}-4-methyl-benzamide (100 mg, 0.25 mmol) is separated by chiral hplc (ChiralCel OJ-H 20×250 mm, 20% EtOH (0.1% DEA): Heptane @ 10 ml/min, 35 C). The first peak to elute is assigned as 82-1 (39 mg) and the second peak as 82-2 (41 mg).

(82-1 and 82-2)

Example 84: N-Cyclopropyl-4-methyl-3-(1'-methyl-1'H-[1,4']bipyrazolyl-4-yl)-benzamide

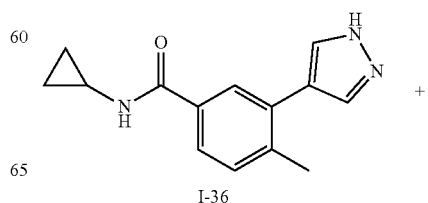

I-36

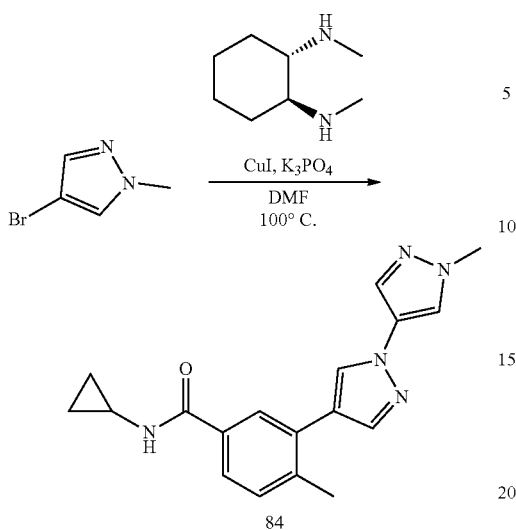

A sample of I-36 (75 mg, 0.31 mmol), 4-bromo-1-methyl-1H-pyrazole (48 mg, 0.47 mmol), CuI (24 mg, 0.12 mmol) and potassium phosphate (132 mg, 0.62 mmol) are combined in degassed DMF (1.5 mL). To this mixture is added trans-1,2-Bis(methylamino)cyclohexane (0.04 mL, 0.25 mmol) and the suspension is heated at 100° C. After 18 h, water (0.15 mL) is added followed by 3 mL of a mixture of 10% water in DMF. The reaction is filtered and the eluent is purified by reversed phase HPLC to afford 38 mg of (84).

The following compounds are synthesized in a similar fashion as described in Example 84 using aryl bromides from commercial sources or as described herein:

N-Cyclopropyl-3-{-1-[7-(2-methoxy-ethoxy)-imidazo[1,2-a]pyridin-3-yl]-1H-pyrazol-4-yl}-4-methyl-benzamide (85)

N-Cyclopropyl-3-[1-(7-methoxy-imidazo[1,2-a]pyridin-3-yl)-1H-pyrazol-4-yl]-4-methyl-benzamide (86)

N-Cyclopropyl-4-methyl-3-[1-(5,6,7,8-tetrahydro-imidazo[1,2-a]pyridin-3-yl)-1H-pyrazol-4-yl]-benzamide (87)

N-Cyclopropyl-4-methyl-3-[1-(2-pyrazol-1-yl-thiazol-5-yl)-1H-pyrazol-4-yl]-benzamide (88)

N-Cyclopropyl-3-[1-(2-hydroxymethyl-thiazol-4-yl)-1H-pyrazol-4-yl]-4-methyl-benzamide (89)

Example 90: N-Cyclopropyl-4-methyl-3-{1-[5-(2-methyl-propane-2-sulfonyl)-4,5,6,7-tetrahydro-pyrazolo[1,5-a]pyrazin-3-yl]-1H-pyrazol-4-yl}-benzamide

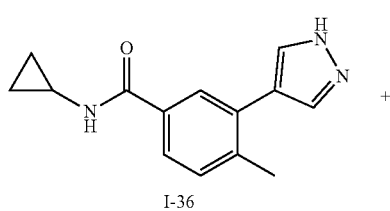

A sample of I-36, I-34 (134 mg, 0.41 mmol), CuI (2 mg, 0.012 mmol) and potassium phosphate (176 mg, 0.83 mmol) are combined in degassed dioxane (1.4 mL) and DMSO (0.5 mL). Ethylene diamine (0.83 □L, 0.012 mmol) is added and the suspension is heated at 60° C. After 16 h, additional 1-34 (134 mg, 0.41 mmol), copper iodide (20 mg, 0.10 mmol) and trans-1,2-bis(methylamino)cyclohexane (0.05 mL, 0.33 mmol) are added and the reaction is heated at 120° C. After heating for an additional 16 hours, the reaction is diluted with EtOAc (4 mL) and the suspension is filtered through a short plug of silica gel (12 mm wide×15 mm high) and the silica plug is eluted with EtOAc (2×2 mL). The combined eluents are concentrated under reduced pressure and the residue is dissolved in a mixture of 10% water in DMSO (2 mL) and purified by reversed phase HPLC to yield 20 mg of the title compound (90).

Example 91: N-Cyclopropyl-3-[1-(6-methoxy-imidazo[1,2-a]pyridin-3-yl)-1H-pyrazol-4-yl]-4-methyl-benzamide

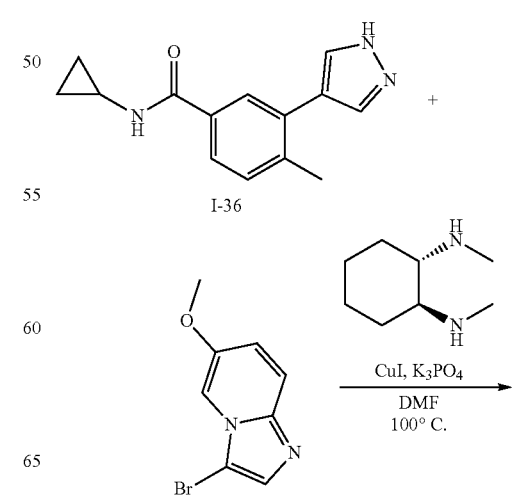

117

-continued

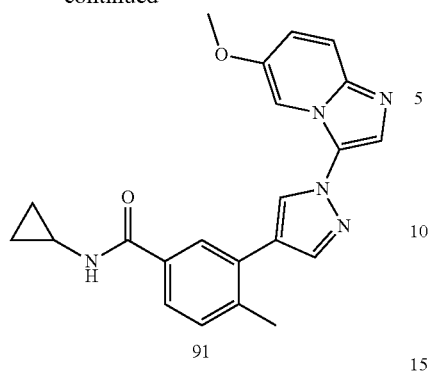

91

A sample of I-36, 3-bromo-6-methoxy-imidazo[1,2-a]pyridine (134 mg, 0.41 mmol), copper iodide (24 mg, 0.12 mmol) and potassium phosphate (132 mg, 0.62 mmol) are combined in degassed DMF (1.5 mL). To this mixture is added trans-1,2-Bis(methylamino)cyclohexane (0.04 mL, 0.25 mmol) and the suspension is heated to 100° C. After 18 h, additional CuI (24 mg, 0.12 mmol) and potassium phosphate (66 mg, 0.31 mmol) are added and the heating is continued. After heating an additional 16 hours, the reaction is diluted with EtOAc (1 mL) and the suspension is filtered through a short plug of silica and the silica plug is eluted with EtOAc (2×2 mL). The combined eluents are concentrated under reduced pressure and the residue is dissolved in a mixture of 10% water in DMSO (2 mL) and purified by reversed phase HPLC to yield 26 mg of (91).

Example 92: N-Cyclopropyl-2-fluoro-4-methyl-5-{1-[6-(1-oxetan-3-yl-piperidin-4-yl)-imidazo[1,2-a]pyridin-3-yl]-1H-pyrazol-4-yl}-benzamide

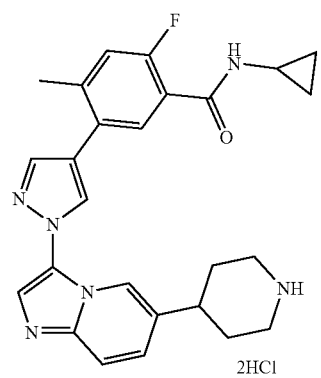

I-41

118

-continued

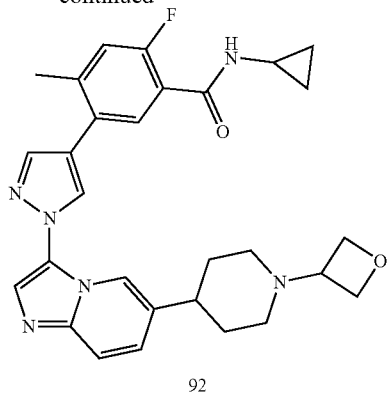

92

The amine salt I-41 (400 mg, 0.8 mmol) is dissolved in MeOH (10 mL), then HOAc (97 mg, 1.6 mmol) and the ketone (0.29 mL, 4 mmol) are added. The solution is stirred for 30 minutes. NaBH₃CN is then added (0.5 g, 8.1 mmol) and the reaction is stirred overnight at 50° C. After cooling down to room temperature, the reaction is quenched by the addition of NaHCO₃, extracted with EtOAc. The combined extracts are concentrated and the residue is purified by flash chromatography (25 g, 0-5% MeOH/DCM) to afford compound 92 (220 mg, 53%).

Example 93: N-Cyclopropyl-5-{1-[6-(1-dimethylcarbamoylmethyl-piperidin-4-yl)-imidazo[1,2-a]pyridin-3-yl]-1H-pyrazol-4-yl}-2-fluoro-4-methylbenzamide

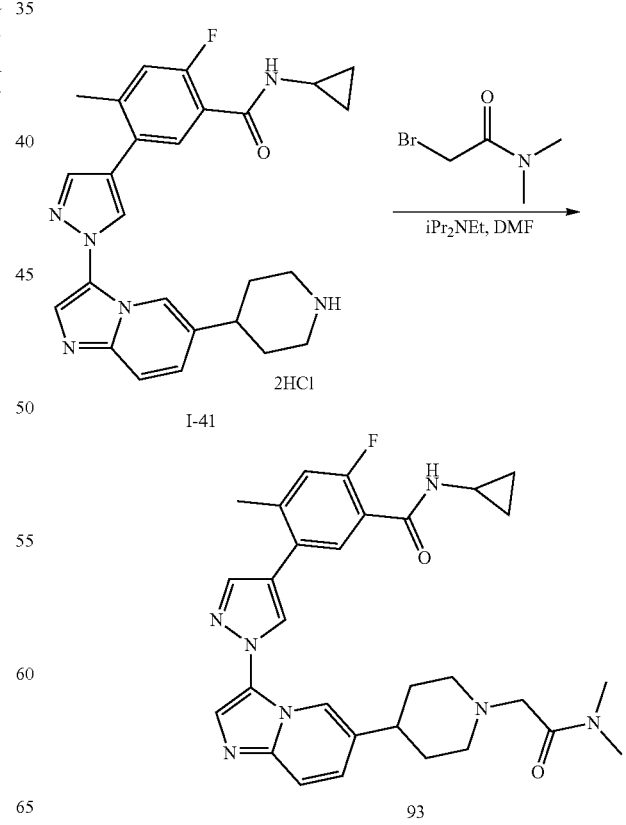

I-41 (1.3 g, 2.6 mmol) is dissolved in DMF (10 mL). iPr₂NEt (4.8 mL, 260 mmol) and the alkyl bromide (520 mg, 3.2 mmol) are added and the solution is stirred at 50° C. for 2 h. The solvent is removed and the residue is diluted with EtOAc, washed with NaHCO₃, brine and concentrated to give a residue, which is purified by flash chromatography (25 g, 0-10% MeOH/DCM), giving crude product contaminated with base. This crude is then purified by reverse phase column (60 g, 0-60% ACN/H2O), giving product as FO salt. This is salt is redissolved in DCM, washed with Na2CO3, concentrated and purified by flash chromatography (25 g, 0-10% MeOH/DCM) to afford 93 as free base (810 mg, 57%).

Example 94: N-Cyclopropyl-2-fluoro-5-{1-[6-(4-fluoro-1-methylpiperidin-4-yl)-7-methoxyimidazo[1,2-a]pyridin-3-yl]-1H-pyrazol-4-yl}-4-methyl-benzamide

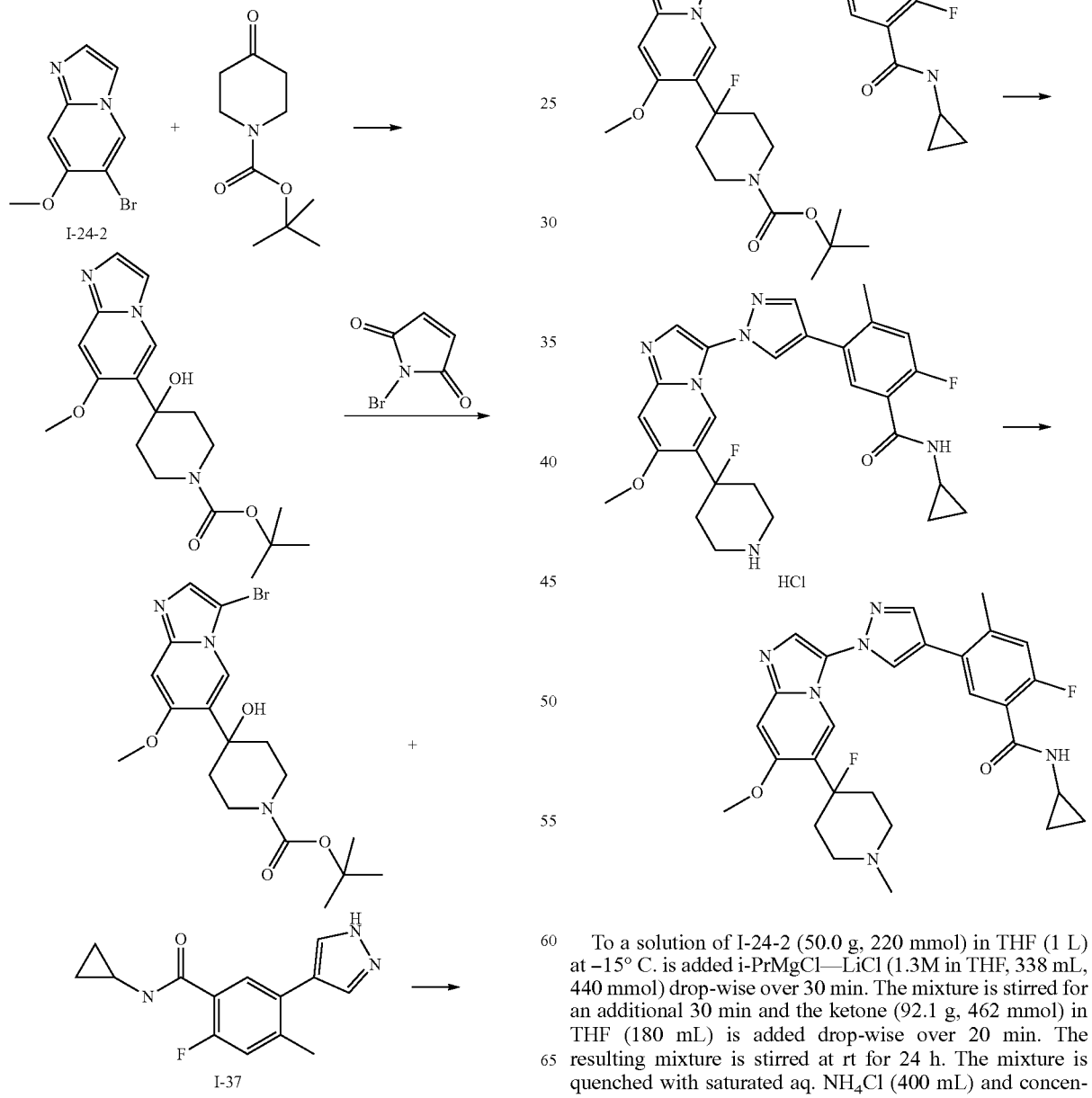

To a solution of I-24-2 (50.0 g, 220 mmol) in THF (1 L) at −15° C. is added i-PrMgCl—LiCl (1.3M in THF, 338 mL, 440 mmol) drop-wise over 30 min. The mixture is stirred for an additional 30 min and the ketone (92.1 g, 462 mmol) in THF (180 mL) is added drop-wise over 20 min. The resulting mixture is stirred at rt for 24 h. The mixture is quenched with saturated aq. NH₄Cl (400 mL) and concentrated. Water is added (400 mL) and extracted with EtOAc (2×600 mL). The combined extracts are washed with brine (400 mL) and concentrated. The crude residue is dissolved in DCM and purified by silica gel chromatography (1-8% MeOH in DCM) to afford the hydroxy piperidine product (30.7 g, 68.1 mmol) as a solid.

the above hydroxy piperidine product (24.6 g, 70.9 mmol) under argon at 0° C. in DCM (470 mL) is added NBS (11.4 g, 63.8 mmol) portion-wise over 10 min. The resulting dark green solution was stirred at 0° C. for 45 min. The 0° C. mixture is quenched with saturated aq NaHCO$_3$ (380 mL). Water is then added (190 mL) and the mixture extracted with DCM (2×250 mL). The combined organic layers are concentrated and the crude product purified by silica gel chromatography (0-5% MeOH in DCM) to give tert-butyl-4-{3-bromo-7-methoxyimidazo[1,2-a]pyridine-6-yl}-4-hydroxypiperidine-1-carboxylate (22.5 g, 52.8 mmoL) as a white solid.

In a pressure-flask with 200 mL of degassed DMF (200 mL) is added tert-butyl-4-{3-bromo-7-methoxyimidazo[1,2-a]pyridine-6-yl}-4-hydroxypiperidine-1-carboxylate (19.9 g, 46.7 mmol) copper iodide (4.4 g, 23.3 mmol), (1S,2S)—N1,N2-dimethyl cyclohexane-1,2-diamine (7.3 mL, 46.7 mmol), 1-37 (14.5 g, 56.0 mmol) and potassium phosphate (19.8 g, 93.4 mmol). The reaction mixture is heated at 90° C. for 24 h. The mixture is cooled to rt in a water bath and diluted with EtOAc (420 mL). The mixture is filtered through celite and evaporated. The resulting residue is portioned between DCM and water. The organic layer is dried with MgSO$_4$ and filtered through celite and evaporated. The resulting thick residue is dissolved in MeOH (400 mL) and water (1.4 L) added drop wise. The resulting solid precipitate was filtered and then purified by silica gel chromatography (100% EtOAc for 10 min, then 0-10% MeOH in EtOAc over 35 min) to give 4-{3-[4-(5-cyclopropylcarbamoyl-4-fluoro-2-methyl-phenyl)-pyrazol-1-yl]-7-methoxy-piperidine-1-carboxylic acid tert-butyl ester (15 g, 20.8 mmol, 84% pure).

To a solution of 4-{3-[4-(5-cyclopropylcarbamoyl-4-fluoro-2-methyl-phenyl)-pyrazol-1-yl]-7-methoxy-piperidine-1-carboxylic acid tert-butyl ester (15 g, 20.8 mmol) in DCM (250 mL) at −78° C. is added [Bis(2-methoxythyl)amino]sulfur trifluoride (50% in THF, 21.3 mL, 49.6 mmol) drop-wise. The mixture is stirred at −78° C. for 10 min. The mixture is allowed to warm to −30° C. over 1 h and then stirred at rt for 1.5 h. The mixture is cooled to 0° C. and quenched with slow addition of saturated aq. NaHCO$_3$ (150 mL). The mixture is stirred for 5 min with bubbling occurring. The organic layer is separated and the aq layer extracted with DCM (2×50 mL). The combined organics are washed with water (100 mL) and dried with sodium sulfate, filtered and concentrated. The resulting crude material is purified by silica gel chromatography (0-10% MeOH in DCM) to give 4-{3-[4-(5-cyclopropylcarbamoyl-4-fluoro-2-methyl-phenyl)-pyrazol-1-yl]-7-methoxy-imidazo[1,2-a]pyridin-6-yl}-4-fluoro-piperidine-1-carboxylic acid tert-butyl ester (10.4 g, 17.2 mmol) as a solid.

To a solution of 4-{3-[4-(5-cyclopropylcarbamoyl-4-fluoro-2-methyl-phenyl)-pyrazol-1-yl]-7-methoxy-imidazo[1,2-a]pyridin-6-yl}-4-fluoro-piperidine-1-carboxylic acid tert-butyl ester (17.8 g, 29.4 mmol) in MeOH (120 mL) is added 4M HCl in dioxane (73.5 mL, 293.9 mmol) and the mixture stirred for 1 h. The mixture is concentrated and the residue dried in a vacuum over at 50° C. for 2 h to give crude N-cyclopropyl-2-fluoro-5-{1-[6-(4-fluoro-piperidin-4-yl)-7-methoxy-imidazo[1,2-a]pyridin-3-yl]-1H-pyrazol-4-yl}-methyl-benzamide hydrochloride (17.6 g, 32.5 mmol) which was used without further purification.

To a solution of N-cyclopropyl-2-fluoro-5-{1-[6-(4-fluoro-piperidin-4-yl)-7-methoxy-imidazo[1,2-a]pyridine-3-yl]-1H-pyrazol-4-yl}-methyl-benzamide hydrochloride (17.6 g, 32.5 mmol) in DCM (335 mL) is added formaldehyde (9.7 mL, 130.2 mmol) and sodium triacetoxyborohydride (27.6 g, 130.2 mmol) and stirred for 45 min. The mixture is quenched with saturated aq NaHCO$_3$ (350 mL) over 30 min. The layers are separated and the aq layer is extracted with DCM (2×200 mL). The combined organics were washed water (2×200 mL), dried over Na$_2$SO$_4$, filtered and concentrated. The crude residue is purified by prep-HPLC to give N-Cyclopropyl-2-fluoro-5-{1-[6-(4-fluoro-1-methylpiperidin-4-yl)-7-methoxyimidazo [1,2-a]pyridin-3-yl]-1H-pyrazol-4-yl}-4-methyl-benzamide (15.0 g, 28.8 mmol) as a white solid.

Example 95: N-Cyclopropyl-5-[1-(6-dimethylaminomethyl-7-methoxy-imidazo[1,2-a]pyridin-3-yl)-1H-pyrazol-4-yl]-2-fluoro-4-methyl-benzamide

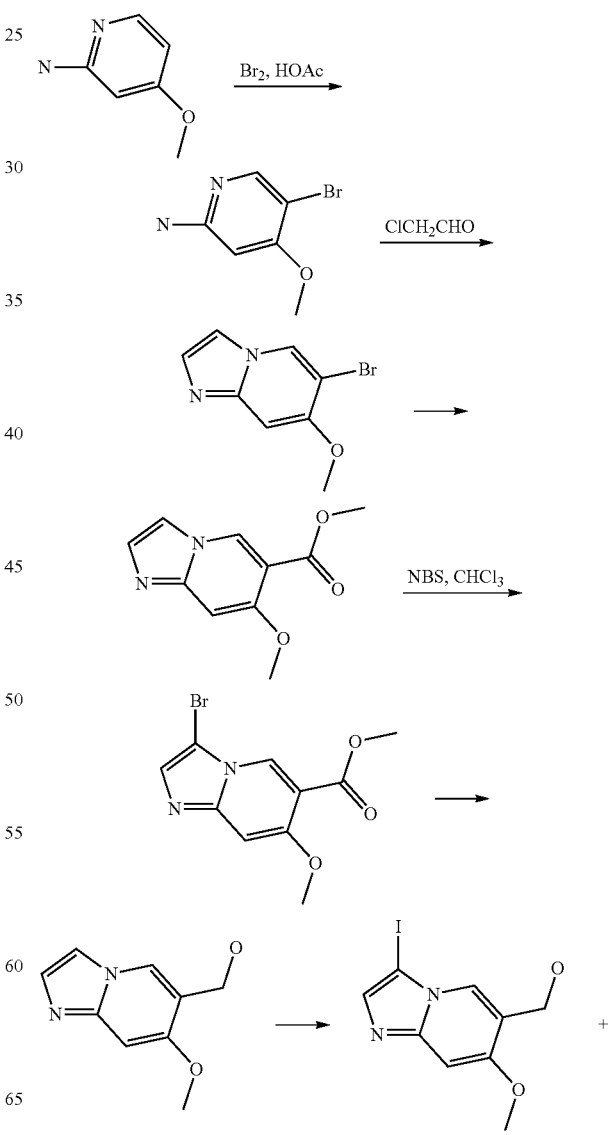

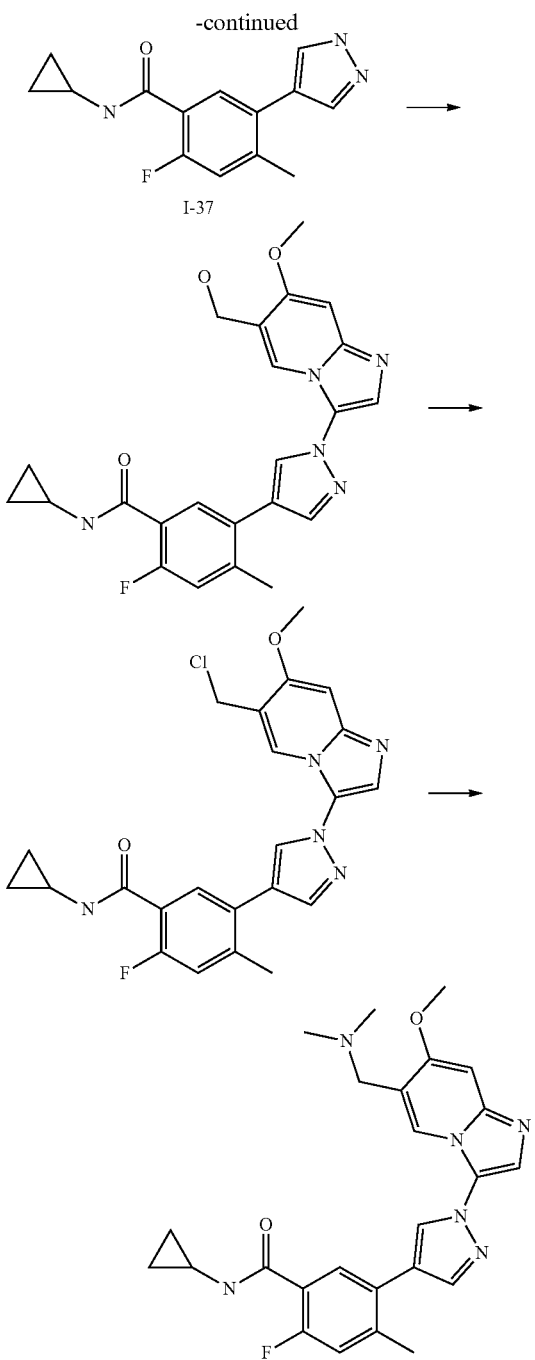

To a solution of 4-Methoxy-pyridin-2-ylamine (45 g; 0.362 mol; 1.0 eq.) in HOAc (1000 mL) is added a solution of Br₂ (57.9 g; 0.362 mol; 1.0 eq.) in HOAc (260 mL) dropwise within 0.5 h. A large amount of white solid is generated. The resultant mixture is stirred at 18° C. for 1.5 h. After filtration, the filter cake is taken up with EtOAc (1500 mL) and washed with sat. NaHCO₃ (500 mL×2), water (300 mL) and brine (200 mL), dried over Na₂SO₄, filtered and concentrated to afford 5-Bromo-4-methoxy-pyridin-2-ylamine (53.0 g; 0.26 mol) as a white solid, which is used in next step without purification.

To a solution of 5-Bromo-4-methoxy-pyridin-2-ylamine (53 g, 0.261 mol, 1.0 eq.) in EtOH:H2O=4:1 (500 mL) is added chloro-acetaldehyde (24.6 g, 0.31 mol), then NaHCO₃ (26.3 g, 0.313 mol) is added. The resultant mixture is heated to 90° C. for 4 h. After cooling to r.t., the organic solvent is evaporated. The residue is extracted with DCM (200 mL×3). The organic layers are combined, dried over Na₂SO₄, filtered and concentrated. The crude product is purified by silica gel chromatography (DCM:MeOH=50:1) to afford compound 6-Bromo-7-methoxy-imidazo[1,2-a]pyridine (39 g, 66%) as a brown solid.

To a solution of 6-Bromo-7-methoxy-imidazo[1,2-a]pyridine (34.9 g, 0.154 mol, 1.0 eq.) in MeOH (350 ml) and Toluene (350 ml) is added TEA (23 g, 0.231 mol, 1.5 eq.), then Pd(dppf)Cl₂ (11.2 g, 0.015 mol, 0.1 eq.) is added under an N₂ atmosphere. The resultant mixture is heated at 80° C. under a CO atmosphere (3 MPa) for 16 h. The solvent is removed under vacuum. The residue is purified by column chromatography (DCM) and washed with PE:EA=1:1 (20 mL) to afford 7-Methoxy-imidazo[1,2-a]pyridine-6-carboxylic acid methyl ester (20 g, 63%) as a brown solid.

To a solution of 7-Methoxy-imidazo[1,2-a]pyridine-6-carboxylic acid methyl ester (20 g, 97 mmol, 1.0 eq.) in CHCl₃ (400 ml) is added NBS (17 g, 97 mmol, 1.0 eq.) at −10° C. under an N₂ atmosphere. The resultant solution is allowed to warm to 0° C. and stirred for 20 min. After dilution with DCM (400 mL), the resultant solution is washed with water (200 mL×2) and brine (300 mL). The organic layer is separated, dried over Na₂SO₄, filtered and concentrated. The residue is washed with a mixture solvent PE:EA=1:1 (500 mL) and DCM (100 mL) to afford compound 3-Bromo-7-methoxy-imidazo[1,2-a]pyridine-6-carboxylic acid methyl ester (15.5 g, 54 mmol) as a pale solid.

3-Bromo-7-methoxy-imidazo[1,2-a]pyridine-6-carboxylic acid methyl ester (10 g, 35 mmol) is suspended in dry THF (200 mL) and to this is added LAH (1M, 105 mL, 105 mmol) dropwise via an addition funnel at RT. The reaction is allowed to stir at RT for 2 h. To the mixture is added water (2 mL), followed by 15% aq NaOH (2 mL) and again water (2 mL). The mixture is stirred for 1 h and the solids removed by filtration. The solids are washed with hot methanol/DCM and the filtrate was concentrated under reduced pressure to give the crude material which was purified by silica gel chromatography (2-10% MeOH in DCM) to give (7-methoxyimidazolo[1,2-a]pyridin-6-yl)-methanol (1.7 g, 9.5 mmol).

(7-methoxyimidazolo[1,2-a]pyridin-6-yl)-methanol (2.7 g, 13.8 mmol) is dissolved in MeCN (150 mL) and MeOH (10 mL) with heat and sonication. NIS is then added (4.3 g, 19.3 mmol) and allowed to stir for 30 min. Satd aq. Na₂CO₃ was added and the mixture extracted with EtOAc (3×100 mL). The combined organic extracts are washed with satd Na₂CO₃, brine and dried with MgSO₄. The mixture is filtered and concentrated to give (3-iodo-7-methoxyimidazo[1,2-a]pyridine-6-yl)methonal which is used without further purification.

3-iodo-7-methoxyimidazo[1,2-a]pyridine-6-yl)methonal (2.6 g, 8.5 mmol) is dissolved in DMF (25 mL) and to this is added I-37 (2.8 g, 11.1 mmol), trans-1,2-bis(methylamino)cyclohexane (1.1 mL, 6.8 mmol), CuI (0.84 g, 4.3 mmol), potassium phosphate tribasic (4.5 g, 21.4 mmol) and the mixture heated at 75° C. overnight. The reaction is cooled to RT and diluted with EtOAc and filtered through celite with EtOAc and water washing. The organic layer is separate, concentrated and the crude residue purified by prep-HPLC to give N-Cyclopropyl-2-fluoro-5-[1-(6-hydroxymethyl-7-methoxy-imidazo[1,2-a]pyridin-3-yl)-1H-pyrazol-4-yl]-4-methyl-benzamide (1.3 g, 3.0 mmol).

(6-hydroxymethyl-7-methoxy-imidazo[1,2-a]pyridine-3-yl)-1H-pyrazol-4-yl]-4-methyl-benzamide (0.69, 1.6 mmol)

was dissolved in DCM (30 mL) and DIPEA (0.414 mL, 2.4 mmol) is added and the reaction cooled to 0° C. in an ice bath. A solution of thionyl chloride (0.14 mL, 1.9 mmol) in DCM (1 mL) is added and the reaction is allowed to stir overnight. An additional equivalent of thionyl chloride in DCM (1 mL) is added and the mixture stirred for 4 h. A subsequent additional equivalent of thionyl chloride in DCM (1 mL) is added and the mixture stirred for 4 h. To the mixture is then added satd. $Na_2CO_3$ and extracted with DCM. The organic layer is separated and concentrated to give the crude product which is purified by silica gel chromatography (1-5% MeOH in DCM) to give 5-[1-(6-Chloromethyl-7-methoxy-imidazo[1,2-a]pyridin-3-yl)-1H-pyrazol-4-yl]-N-cyclopropyl-2-fluoro-4-methyl-benzamide (0.15 g, 0.33 mmol) as a white solid.

5-[1-(6-Chloromethyl-7-methoxy-imidazo[1,2-a]pyridin-3-yl)-1H-pyrazol-4-yl]-N-cyclopropyl-2-fluoro-4-methyl-benzamide (0.1 g, 0.24 mmol) is dissolved in DCM and to this is added dimethyamine (2.0M in DCM, 1.7 mL, 3.3 mmol) and the reaction allowed to stir at RT overnight. The mixture is concentrated and purified directly by column chromatography (25-100% EtOAc in heptanes) to give 95 (0.1 g, 0.24 mmol) as a white solid.

Example 96: N-Cyclopropyl-5-{1-[7-ethoxy-6-(4-fluoro-1-methyl-piperidin-4-yl)-imidazo[1,2-a]pyridin-3-yl]-1H-pyrazol-4-yl}-2-fluoro-4-methyl-benzamide

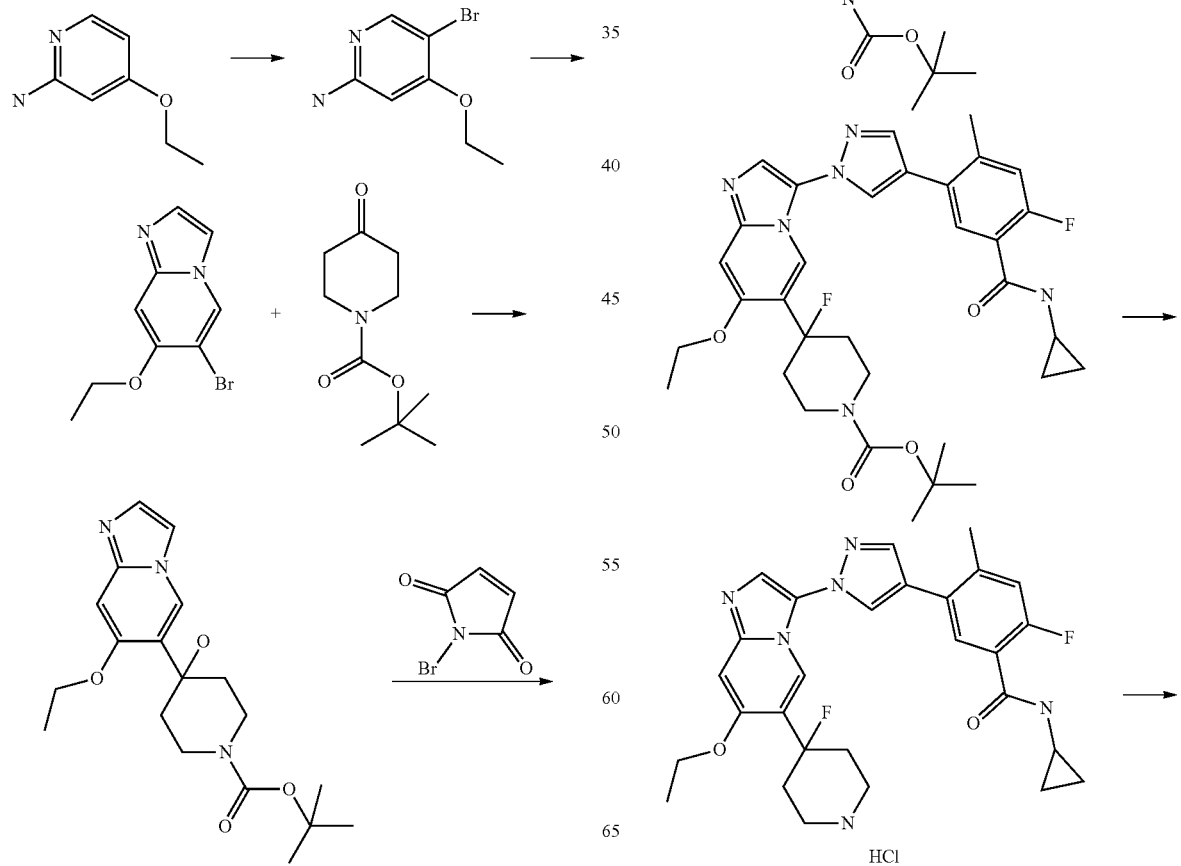

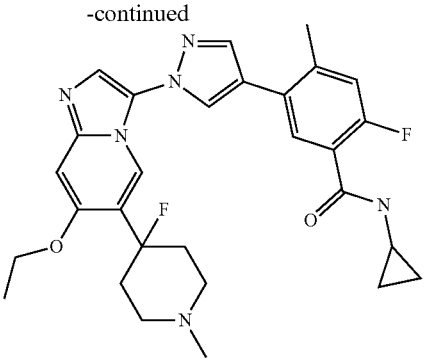

4-Ethoxy-pyridin-2-ylamine (15 g, 109 mmol) is dissolved in HOAc (100 mL) and cooled to 0° C. Bromine is added dropwise with vigorous stirring. The mixture is allowed to stir at RT for 30 minutes at which point a precipitate forms. The mixture is stirred for 30 min and the solids collected by filtration, washed with EtOAc in dried in a vacuum oven to give 5-bromo-4-ethoxy-pyridin-2-ylamine hydrobromide (23.3 g, 78.2 mmol).

5-bromo-4-ethoxy-pyridin-2-ylamine hydrobromide (23.4 g, 78.5 mmol) is dissolved in EtOH (500 mL) and to this is added sodium hydrogen carbonate (26.4 g, 314 mmol). 2-chloroacetaldehyde (14.9 mL, 118 mmol) is then added dropwise. After the addition, the mixture is heated at 115° C. for 1 h and then cooled to RT and allowed to stir overnight. The mixture is filtered and the filtrate concentrated under reduced pressure. The residue is partitioned between EtOAc and water. The organic layer is separated, dried with MgSO₄, filtered and concentrated to give 6-Bromo-7-ethoxy-imidazo[1,2-a]pyridine (6.8 g, 28.2 mmol).

6-Bromo-7-ethoxy-imidazo[1,2-a]pyridine (0.92 g, 3.8 mmol) is dissolved in THF (40 mL). The solution is cooled to −20° C. and then iPrMgCl LiCL complex (1.3M in THF, 5.9 mL, 7.6 mmol) is added dropwise. After 30 min 1-Boc-4-piperidone (1.6 g, 8.0 mmol) is added and the reaction allowed to warm to RT. The mixture is quenched with satd NH₄Cl and extracted with EtOAc. The organics are separated and dried with MgSO₄, filtered and concentrated to give the crude product which was purified by silica gel chromatography (0-10% MeOH in DCM) to give tert-butyl 4-(7-ethoxyimidazo[1,2-a]pyridine-6-yl)-4-hydroxypiperidine-1-carboxylate (0.38 g, 1.0 mmol).

Tert-Butyl 4-(7-ethoxyimidazo[1,2-a]pyridine-6-yl)-4-hydroxypiperidine-1-carboxylate (0.38 g, 1.0 mmol) is dissolved in DCM (8 mL) and cooled to 0° C. To this is added NBS (0.19 g, 1.1 mmol) and the mixture stirred at RT overnight. The mixture is diluted with DCM and washed with satd NaHCO₃. The organic layer is separated, dried with MgSO₄ and concentrated under reduced pressure to give the crude product which is purified by silica gel chromatography (0-10% MeOH in DCM) to give tert-butyl-4-(3-bromo-7-ethoxyimidazo[1,2-a]pyridine-6-yl)-4-hydroxypiperidine-1-carboxylate (0.39 g, 0.87 mmol).

tert-butyl-4-(3-bromo-7-ethoxyimidazo[1,2-a]pyridine-6-yl)-4-hydroxypiperidine-1-carboxylate (0.39 g, 0.87 mmol) is dissolved in DMF (20 mL) and to this is added CuI (0.066 g, 0.35 mmol), 1-37 (0.25 g, 0.95 mmol) potassium phosphate tribasic (0.37 g, 1.7 mmol) and (1S,2S)—N1,N2-dimethylcyclohexane-1,2-diamine (0.11 mL, 0.69 mmol) and degassed with argon. The reaction vessel is sealed at the mixture heated at 85° C. overnight. The mixture is cooled to RT and diluted with EtOAc (150 mL). The mixture is filtered through celite and the filtrate evaporated. The residue is partitioned between EtOAc and water. The organic layer is separated, dried with MgSO₄ and concentrated to give the crude product that was purified by silica gel chromatography (0-5% MeOH in DCM) to give tert-butyl 4-(3-{4-[5-(cyclopropylcabamoyl)-4-fluoro-2-methylphenyl]-1H-pyrazol-1-yl}-7-ethoxyimidazo[1,2-a]pyridine-6-yl)-4-hydroxypiperidine-1-carboxylate (0.36 g, 0.58 mmol).

Tert-Butyl 4-(3-{4-[5-(cyclopropylcabamoyl)-4-fluoro-2-methylphenyl]-1H-pyrazol-1-yl}-7-ethoxyimidazo[1,2-a]pyridine-6-yl)-4-hydroxypiperidine-1-carboxylate (0.36 g, 0.58 mmol) is dissolved in DCM (5 mL) and cooled in a dry ice/acetone bath. To this added Bis(2-methoxyethyl)amino]sulfur trifluoride (50% in THF, 0.32 mL, 0.76 mmol) dropwise. The mixture was stirred in the bath for 30 min and then transferred to a water bath for 1 h. The mixture is quenched at 0° C. with NaHCO₃. The mixture is diluted with DCM and extracted. The organic phase is separated and concentrated under reduced pressure to give the crude product which is purified by prep-HPLC to give 4-{3-[4-(5-Cyclopropylcarbamoyl-4-fluoro-2-methyl phenyl)-pyrazol-1-yl]-7-ethoxy-imidazo[1,2-a]pyridin-6-yl}-4-fluoro-piperidine-1-carboxylic acid tert-butyl ester (0.15 g, 0.25 mmol).

4-{3-[4-(5-Cyclopropylcarbamoyl-4-fluoro-2-methyl phenyl)-pyrazol-1-yl]-7-ethoxy-imidazo[1,2-a]pyridin-6-yl}-4-fluoro-piperidine-1-carboxylic acid tert-butyl ester (0.15 g, 0.25 mmol) is dissolved in DCM (5 mL) and MeOH (1 mL) and to this is added HCl in dioxane (4M, 4 mL). The mixture is stirred at RT for 2 h. The mixture is concentrated under reduced pressure to give N-Cyclopropyl-5-{1-[7-ethoxy-6-(4-fluoro-piperidin-4-yl)-imidazo[1,2-a]pyridin-3-yl]-1Hpyrazol-4-yl}-2-fluoro-4-methyl-benzamide hydrochloride (0.14 g, 0.24 mmol).

N-Cyclopropyl-5-{1-[7-ethoxy-6-(4-fluoro-piperidin-4-yl)-imidazo[1,2-a]pyridin-3-yl]-1Hpyrazol-4-yl}-2-fluoro-4-methyl-benzamide hydrochloride (0.14 g, 0.24 mmol) is dissolved in DCM (5 mL) and MeOH (1 mL). To this is added formaldehyde (0.071 mL, 0.98 mmol) and sodium bis(acetyloxy)boranuidyl acetate (0.21 g, 0.98 mmol). The mixture was stirred at RT for 15 min and then quenched with NaHCO₃ and extracted with DCM. The combined organic extracts were dried with MgSO₄, filtered and concentrated under reduced pressure. The residue was triturated with MeOH and filtered to give 96 as a white solid (0.081 g, 0.15 mmol).

Example 97: N-Cyclopropyl-2-fluoro-4-methyl-5-{1-[6-(1-methyl-azetidin-3-yl)-imidazo[1,2-a]pyridin-3-yl]-]H-pyrazol-4-yl}-benzamide

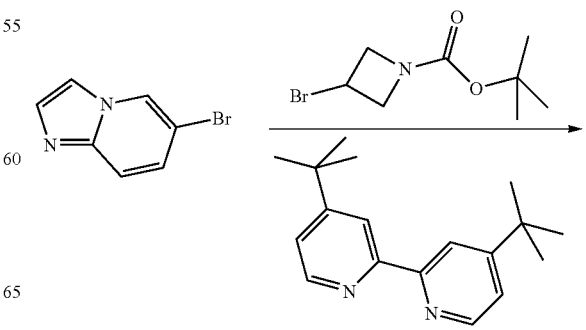

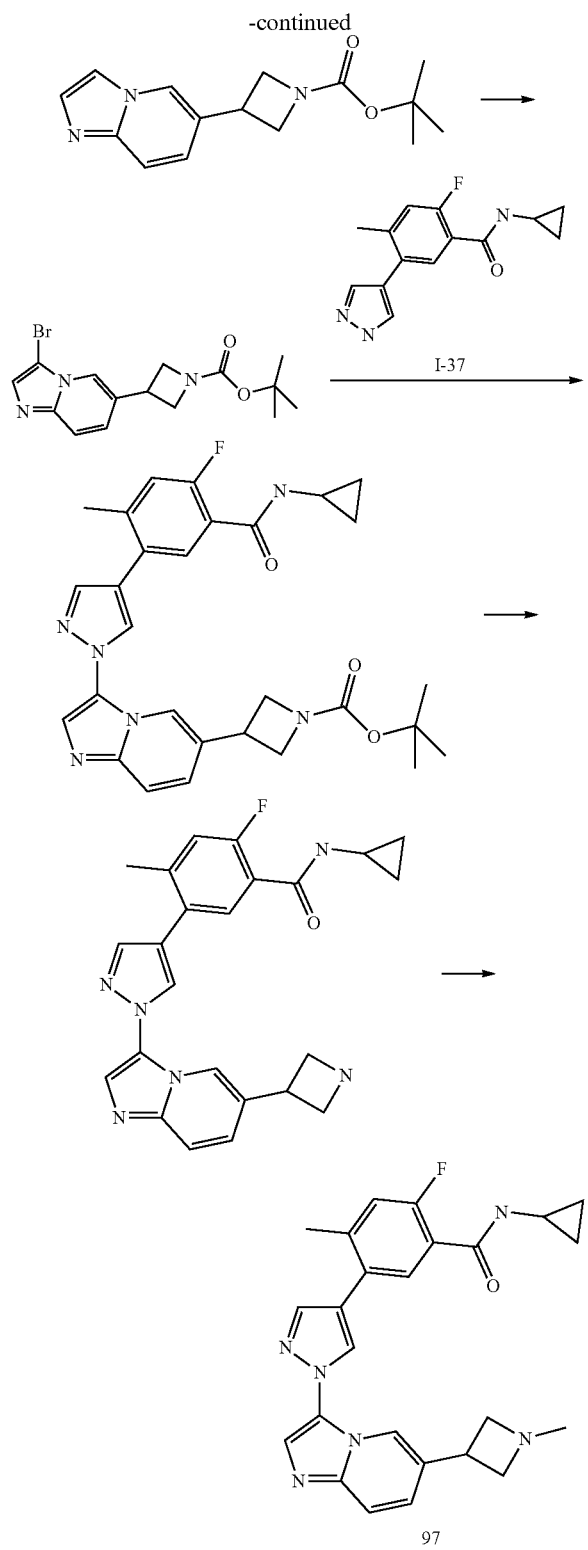

6-Bromo-imidazo[1,2-a]pyridine (1.0 g, 0.005 mol) was charged in a microwave vial and to this is added 4,4'-di-tert-butyl-2,2'-biprydine (0.14 g, 0.001 mol), 3-bromo-azetidine-1-carboxylic acid tert-butyl ester (1.2 g, 0.005 mol), zinc powder (0.66 g, 0.01 mol), NiI$_2$ (0.16 g, 0.001 mol) and MgCl$_2$ (0.48, 0.005 mol). To this is added pyridine (0.4 g, 0.005 mol) and DMA (15 mL). The reaction was closed and heated at 65° C. for 16 h. The mixture is cooled to RT, diluted with EtOAc and washed with satd NaHCO$_3$ and brine. The organic layer is concentrated and the residue purified by silica gel chromatography (0-100% EtOAc in heptanes, followed by 5% MeOH in DCM) to give the crude product which was subsequently purified by prep-HPLC to give 3-imidazo[1,2-a]pyridine-6-yl-azetidine-1-carboxylic acid tert-butyl ester (0.85 g, 3.1 mmol).

3-Imidazo[1,2-a]pyridine-6-yl-azetidine-1-carboxylic acid tert-butyl ester (0.85 g, 3.0 mmol) is dissolved in CHCl$_3$ (15 mL) and to this is added NBS and the mixture allowed to stir at RT for 2 h. The reaction is concentrated under reduced pressure and the residue is diluted with EtOAc and washed with satd NaHCO$_3$, brine and the organic layer concentrated. The resulting crude product is purified by silica gel chromatography (0-100% EtOAc in heptanes) to give 3-(3-bromo-imidazo[1,2-a]pyridine-6-yl)-azetidine-1-carboxylic acid tert-butyl ester (0.84 g, 2.4 mmol).

3-(3-Bromo-imidazo[1,2-a]pyridine-6-yl)-azetidine-1-carboxylic acid tert-butyl ester (0.84 g, 2.4 mmol) is dissolved in DMF (8.0 mL) and to this is added CuI (0.23 g, 1.2 mmol), (1R,2R)-dimethylaminoacyclohexane (0.27 g, 1.9 mmol), I-37, (0.74 g, 2.9 mmol) and potassium phosphate tribasic (1.0 g, 4.8 mmol) and the mixture heated at 65° C. overnight. The mixture was cooled to RT and diluted with EtOAc. The mixture is washed with water, brine and the organic layer concentrated to give the crude product which is purified by silica gel chromatography (0-100% EtOAc in heptanes) followed by reverse phase chromatography (10-100% water/MeCN with 0.5% formic acid) to give 3-{3-[4-(5-cyclopropylcarbamoyl-4-fluoro-2-methyl-phenyl)-pyrazol-1-yl]-imidao[1,2-a]pyridine-6-yl}-azetidine-1-carboxylic acid tert-butyl ester (0.62 g, 1.2 mmol).

3-{3-[4-(5-Cyclopropylcarbamoyl-4-fluoro-2-methyl-phenyl)-pyrazol-1-yl]-imidao[1,2-a]pyridine-6-yl}-azetidine-1-carboxylic acid tert-butyl ester (0.62 g, 1.2 mmol) is dissolved in DCM (5.0 mL) and MeOH (2.0 mL) and to this is added 4M HCl in dioxane (1.8 mL, 7.0 mmol). The mixture was cooled in an ice bath and allowed to stir overnight. The mixture was concentrated, diluted with DCM/MeOH and washed with satd NaHCO$_3$. The organic layer was concentrated and the residue purified by silica gel chromatography (0-10% MeOH in DCM with 1% NH$_4$OH to give 5-[1-(6-azetidin-3-yl-imidazo[1,2-a]pyridine-4-yl)-N-cylcopropyl-2-fluoro-4-methyl-benzamide (0.39 g, 0.91 mmol).

5-[1-(6-Azetidin-3-yl-imidazo[1,2-a]pyridine-4-yl)-N-cylcopropyl-2-fluoro-4-methyl-benzamide (0.07 g) is dissolved in MeOH (2 mL) and to this is added formaldehyde (0.13 mL, 1.6 mmol). The mixture is stirred for 30 min then NaBH$_3$CN (0.10 g, 1.6 mmol) and acetic acid (0.019 g, 0.33 mmol) are added and the reaction heated at 50° C. overnight. The mixture is cooled to RT, neutralized with satd NaHCO$_3$ and the organic layer separated. The organics are concentrated and the crude product purified by silica gel chromatography (0-5% MeOH in DCM with 1% NH$_4$OH to give 97 (0.032 g, 0.072 mmol).

131

Example 98: N-Cyclopropyl-2-fluoro-4-methyl-5-{1-[6-((R)-1-methyl-pyrrolidin-3-yl)-imidazo[1,2-a]pyridin-3-yl]-1H-pyrazol-4-yl}-benzamide(99)

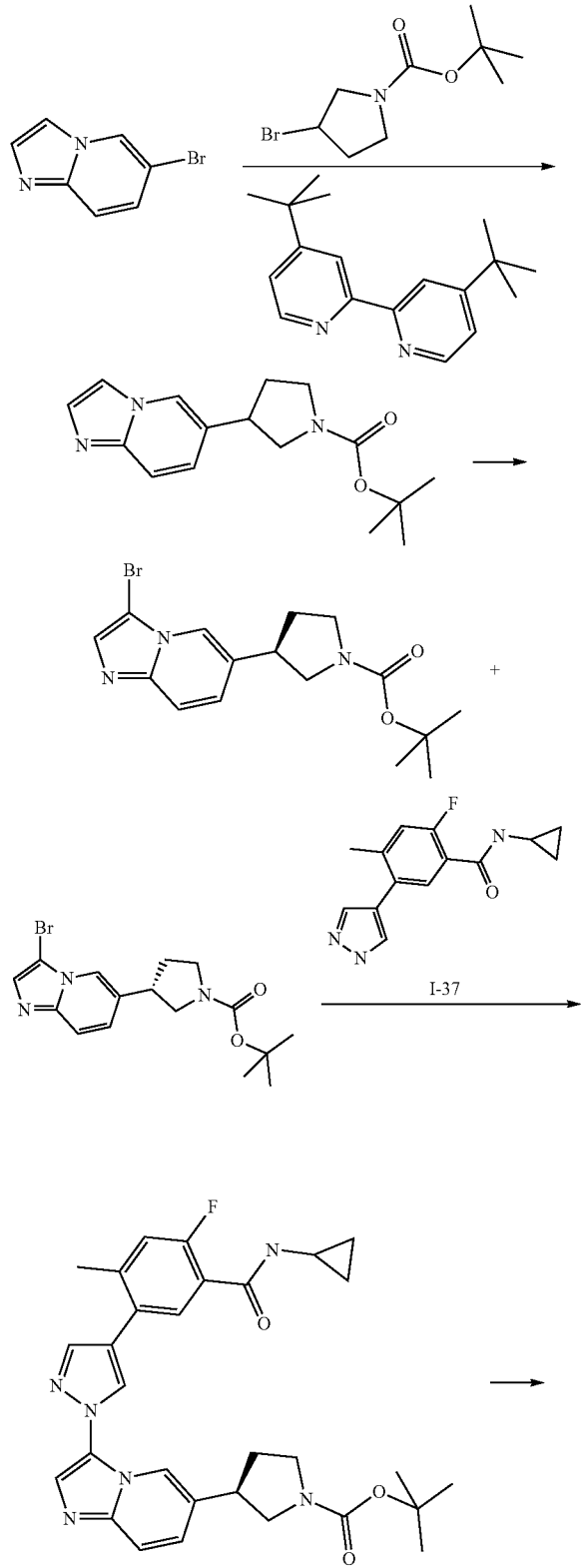

132

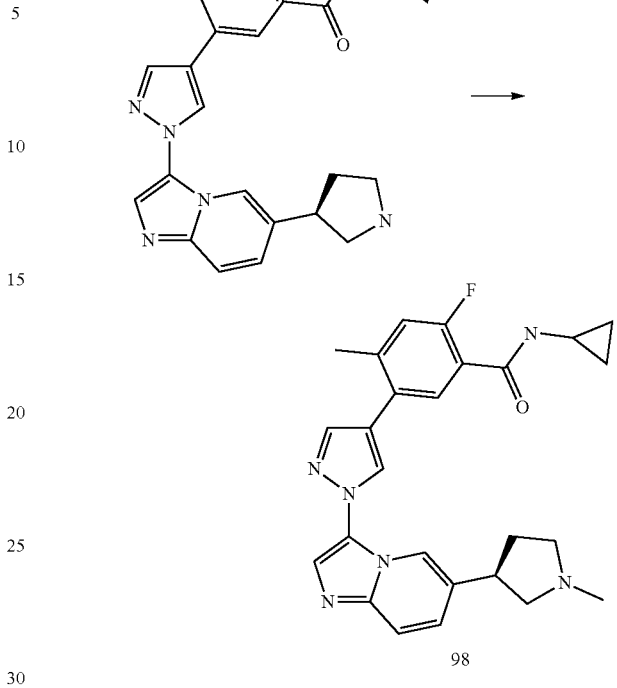

6-Bromoimidazo[1,2-a]pyridine (3.9 g, 20 mmol), 3-bromo-pyrrolidine-1-carboxylic acid tert-butyl ester (5.0 g, 20 mmol), NiI₂ (0.62 g, 2.0 mmol), 4,4'-di-tert-butyl-2,2'-biprydine (0.54 g, 2.0 mmol) and MgCl₂ (0.19 g, 20 mmol) in a pressure flask are dissolved in pyridine and DMA. The mixture is heated at 65° C. for 3 days. The mixture is cooled to RT and diluted with EtOAc. The mixture is washed with satd NaHCO₃, water and brine. The organic layer is concentrated and the crude product purified by silica gel chromatography (0-10% MeOH in DCM) to give 3-imidazol[1,2a]pyridine-6-yl-pyrrolidine-1-carboxylic acid tert-butyl ester (2.7 g, 6.1 mmol).

3-Imidazol[1,2a]pyridine-6-yl-pyrrolidine-1-carboxylic acid tert-butyl ester (2.7 g, 6.1 mmol) is dissolved in CHCl₃ (30 mL) and cooled to 0° C. To this is added NBS (1.1 g, 6.1 mmol) and allowed to stir for 30 min. The mixture is concentrated and purified by silica gel chromatography. The enantiomers are then separated by chiral HPLC to give (R)-3-(3-Bromo-imidazo[1,2-a]pyridin-6-yl)-pyrrolidine-1-carboxylic acid tert-butyl ester (0.65 mmol, 1.6 mmol) and (S)-3-(3-Bromo-imidazo[1,2-a]pyridin-6-yl)-pyrrolidine-1-carboxylic acid tert-butyl ester (0.59 g, 1.6 mmol). The stereochemistry is arbitrarily assigned.

(R)-3-(3-Bromo-imidazo[1,2-a]pyridin-6-yl)-pyrrolidine-1-carboxylic acid tert-butyl ester (0.65 mmol, 1.6 mmol) is dissolved in DMF (5.0 mL) and to this is added Cu (0.15 g, 0.81 mmol), 1R,2R-dimethylaminoacylohexane (0.20 mL, 1.3 mmol), I-37 (0.5 g, 1.9 mmol) and potassium phosphate tribasic (0.69 g, 3.3 mmol) and the mixture heated at 65° C. overnight. The mixture is cooled to RT, diluted with EtOAc and washed with water (2×50 mL) and brine. The organic layer is concentrated and purified by silica gel chromatography first with 0-10. MeOH in DCM, then 10-95% MeCN in water with 0.1% formic acid to give (R)-3-{3-[4-(5-Cyclopropylcarbamoyl-4-fluoro-2-methyl-phenyl)-pyrazol- 1-yl]-imidazo[1,2-a]pyridin-6-yl}-pyrrolidine-1-carboxylic acid tert-butyl ester (0.62 g, 1.1 mmol).

Cyclopropylcarbamoyl-4-fluoro-2-methyl-phenyl)-pyrazol-1-yl]-imidazo[1,2-a]pyridin-6-yl}-pyrrolidine-1-carboxylic acid tert-butyl ester (0.23 g, 0.42 mmol) is dissolved in MeOH (1 mL) and to this is added 4N HCl in dioxane (0.53 mL, 2.1 mmol) and mixture stirred at RT overnight. The reaction is concentrated to give N-cyclopropyl-2-fluoro-4-methyl-5-[1-((R)-6-pyrrolidin-3yl-imidazo[1,2-a]pyridin-3-yl)-1H-pyrazol-4-yl]-benzamide hydrochloride (0.26 g, 0.53 mmol).

N-Cyclopropyl-2-fluoro-4-methyl-5-[1-((R)-6-pyrrolidin-3yl-imidazo[1,2-a]pyridin-3-yl)-1H-pyrazol-4-yl]-benzamide hydrochloride (0.20 g, 0.42 mmol) is dissolved in DCM (4 mL) and to this is added formaldehyde (0.31 mL, 4.2 mmol) and NaBH(OAc)$_3$ (1.3 g, 6.4 mmol) and allowed to stir overnight. The mixture is quenched with satd NaHCO$_3$ and extracted with DCM (3×50 mL). The combined organic layers are washed with water, brine and concentrated under reduced pressure. The crude material is purified by silica gel chromatropgraphy (10% MeOH in DCM) to give 98 (0.096 g, 0.21 mmol).

Example 99: N-Cyclopropyl-2-fluoro-4-methyl-5-{1-[6-((S)-1-methyl-pyrrolidin-3-yl)-imidazo[1,2-a]pyridin-3-yl]-1H-pyrazol-4-yl}-benzamide 99 was prepared in an analogous fashion as 98 but from (S)-3-(3-Bromo-imidazo[1,2-a]pyridin-6-yl)-pyrrolidine-1-carboxylic acid tert-butyl ester.

Example 100: N-Cyclopropyl-2-fluoro-5-{1-[6-(4-fluoro-1-methyl-piperidin-4-yl)-7-methoxy-imidazo[1,2-a]pyridin-3-yl]-1H-imidazol-4-yl}-4-methyl-benzamide The title compound was prepared in an analogous fashion as example 94 using I-39-2.

Example 101: N-Cyclopropyl-5-{1-[6-(1-ethyl-4-fluoro-piperidin-4-yl)-7-methoxy-imidazo[1,2-a]pyridin-3-yl]-1H-pyrazol-4-yl}-2-fluoro-4-methyl-benzamide

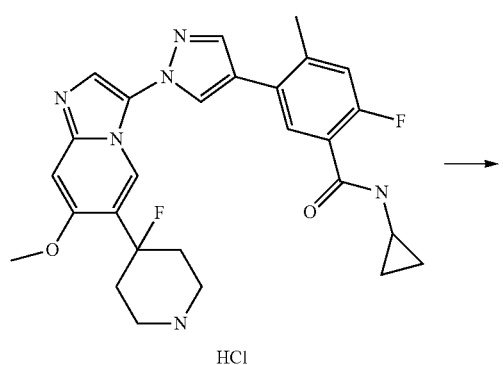

HCl

→

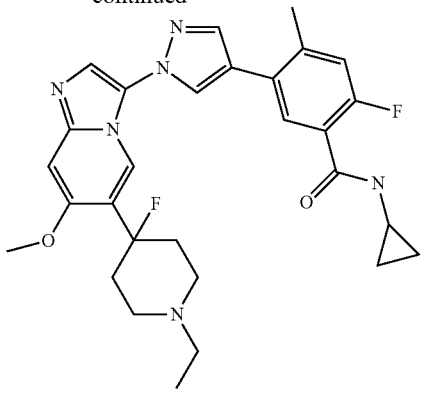

N-cyclopropyl-2-fluoro-5-{1-[6-(4-fluoro-piperidin-4-yl)-7-methoxy-imidazo[1,2-a]pyridine-3-yl]-1H-pyrazol-4-yl}-methyl-benzamide hydrochloride (0.060 g, 0.12 mmol) is dissolved in DCM (2.0 mL) and to this is added acetaldehyde (0.019 mL, 0.36 mmol) and NaBH(OAc)$_3$ (0.10 g, 0.45 mmol) and allowed to stir at RT overnight. The mixture is quenched with satd NaHCO$_3$, and extracted with DCM. The combined organic extracts were washed with brine and concentrated to give the crude product which was purified by prep-HPLC to give 101 (0.008 g, 0.016 mmol).

HPLC and MS Data for compounds in Table 1 are shown in Table 3, which are measured using the methods set forth in the following Table 2.

TABLE 2

| | | | HPLC Method | | | |
|---|---|---|---|---|---|---|
| | | | Gradient | | Flow | |
| Method | Mobile Phase A | Mobile Phase B | Time (min) | % A | % B | (mL/min.) | Column |
| A | 0.1% Formic Acid in Water | 0.1% Formic Acid in ACN | 0 | 95.0 | 5.0 | 0.8 | BEH 2.5 × 50 mm C18, 1.7 μm particle diameter |
| | | | 1.0 | 5.0 | 95.0 | | |
| | | | 1.3 | 5.0 | 95.0 | | |
| | | | 1.4 | 95.0 | 5.0 | | |
| | | | 1.7 | 95.0 | 5.0 | | |

Assessment of Biological Properties

RIPK2 inhibition for compounds in Table 1 are shown in Table 3 and measured using the following method:

Materials: White, 384-well optiplates (cat. no. 6007290) were purchased from PerkinElmer. The V9103X ADP-Glo Kinase Assay Custom (including ultra-pure ATP) was purchased from Promega. 8His-RIPK2 FL was prepared in-house. All other materials were of highest grade commercially available.

Method: In a 384-well plate, test compound diluted in assay buffer (1% DMSO final) is mixed with 8His-RIPK2 FL enzyme (final concentration of 8 nM). After 15 minutes of pre-incubation at RT, ATP dissolved in assay buffer is added (final concentration 5 μM). The mixture is incubated for 60 minutes at 37° C. in a humidified incubator. Then, ADP Glo Reagent is added, followed by a 40 minute incubation at rt. Finally, Kinase Detection Reagent is added and the entire mixture is incubated for 40 min at RT. The luminescence signal is measured with an Envision reader to determine the amount of ADP produced. Assay buffer: 25 mM HEPES (4-(2-hydroxyethyl)-1-piperazinethanesulfonic acid), 0.1% BSA (bovine serum albumin), 10 mM MgCl2, 5 mM MnCl2, 50 mM KCl, 0.01% CHAPS (3-[(3-cholamidopropyl)dimethylammonio]-1-propanesulfonate), 10 µM Na3VO4, 1 mM DTT (dithiothreitol), pH 7.5 All plates contain wells with vehicle controls instead of compound (1% DMSO) as reference for the high signal (100% CTL (100% of control), high signal), and wells without enzyme as reference for low signal (0% CTL, low signal). The luminescent signal generated is proportional to the ADP produced and is correlated with enzyme activity. The analysis of the data is performed by the calculation of the percentage of ADP production in the presence of the test compound and RIPK2 as compared to the ADP production in the presence of RIPK2 plus 50 µM Gefitinib. (RLU (relative luminescence units)(sample)−RLU(low control)) *100/(RLU(high value)−RLU(low control)) [RLU=relative luminescence units].

TABLE 3

| Example | m/z | rt (min) | RIPK2 IC$_{50}$ (nM) |
|---|---|---|---|
| 1 | 476.2 | 0.55 | 2.6 |
| 2 | 434.4 | 0.87 | 4.7 |
| 3 | 415.3 | 0.66 | 66 |
| 5 | 395.1 | 0.61 | 3.5 |
| 6 | 396.1 | 0.69 | 12 |
| 7 | 419.1 | 0.65 | 0.99 |
| 8 | 410.1 | 0.65 | 14 |
| 9 | 427.2 | 0.76 | 3 |
| 10 | 516.3 | 0.82 | 1.3 |
| 11 | 395.1 | 0.85 | 2.9 |
| 12 | 396.1 | 0.75 | 640 |
| 13 | 358.2 | 0.63 | 25 |
| 14 | 381.1 | 0.69 | 3 |
| 15 | 357.7 | 0.55 | 11 |
| 16 | 357.2 | 0.54 | 45 |
| 17 | 381.1 | 0.62 | 7.4 |
| 19 | 477.2 | 0.78 | 2.2 |
| 20 | 477.2 | 0.83 | 970 |
| 21 | 473.1 | 0.76 | 6.7 |
| 22 | 477.2 | 0.71 | 66 |
| 23 | 445.2 | 0.68 | 4.5 |
| 25 | 406.3 | 0.72 | 150 |
| 26 | 419.1 | 0.84 | 55 |
| 27 | 449.2 | 0.7 | 12 |
| 28 | 507.2 | 0.8 | 150 |
| 29 | 477.7 | 0.83 | 1.6 |
| 30 | 479.2 | 0.73 | 170 |
| 31 | 401.2 | 0.59 | 4.2 |
| 32 | 375.1 | 0.58 | 3.5 |
| 33 | 495.2 | 0.8 | 3.8 |
| 34 | 406.2 | 0.73 | 4.4 |
| 35 | 507.2 | 0.72 | 1.2 |
| 36 | 524.2 | 0.76 | 1.6 |
| 37 | 507.3 | 0.74 | 5.2 |
| 38 | 520.3 | 0.58 | 26 |
| 39 | 537.2 | 0.62 | 4 |
| 40 | 416.4 | 0.73 | 120 |
| 41 | 429.3 | 0.66 | 130 |
| 42 | 363.2 | 0.82 | 1700 |
| 43 | 324.1 | 0.71 | 26 |
| 44 | 394.1 | 0.95 | 360 |
| 45 | 407.1 | 0.77 | 1.2 |
| 46 | 409.2 | 0.75 | 110 |
| 47 | 400.1 | 0.96 | 110 |
| 48 | 417.1 | 0.82 | 55 |
| 49 | 393.2 | 0.75 | 390 |
| 50 | 407.2 | 0.89 | 1400 |
| 53 | 352.4 | 0.58 | 710 |
| 54 | 340.3 | 0.74 | 140 |
| 55 | 336.3 | 0.49 | 260 |
| 56 | 419.1 | 0.72 | 16 |
| 57 | 401.1 | 0.64 | 9.5 |
| 58 | 401.1 | 0.61 | 320 |
| 59 | 463.3 | 0.72 | 2.4 |
| 60 | 476.3 | 0.57 | 2.1 |
| 61 | 445.3 | 0.65 | 4.8 |
| 62 | 401.4 | 0.66 | 4.1 |
| 63 | 458.4 | 0.31 | 9.3 |
| 64 | 470.2 | 0.64 | 19 |
| 65 | 483.2 | 0.53 | 10 |
| 66 | 428.2 | 0.63 | 7.6 |
| 67 | 414.7 | 0.64 | 3.1 |
| 68 | 415.3 | 0.69 | 3.1 |
| 69 | 446.2 | 0.71 | 3 |
| 70 | 501.2 | 0.6 | 5.5 |
| 71 | 419.2 | 0.6 | 2.6 |
| 72 | 401.2 | 0.56 | 4.3 |
| 73 | 471.2 | 0.57 | 31 |
| 74 | 402.3 | 0.56 | 55 |
| 75 | 433.2 | 0.67 | 1.4 |
| 76 | 400.2 | 0.68 | 9.7 |
| 77 | 478.4 | 0.71 | 7.2 |
| 78 | 494.2 | 0.77 | 500 |
| 79 | 476.2 | 0.54 | 3.2 |
| 80 | 504.2 | 0.56 | 11 |
| 81-1 | 419.2 | 0.69 | 2.4 |
| 81-2 | 419.2 | 0.69 | 1.9 |
| 82-1 | 401.2 | 0.57 | 6.7 |
| 82-2 | 401.2 | 0.58 | 3.2 |
| 84 | 321.2 | 0.74 | 23 |
| 85 | 431.6 | 0.58 | 3.9 |
| 86 | 387.2 | 0.57 | 4 |
| 87 | 361.2 | 0.52 | 190 |
| 88 | 390.1 | 0.86 | 17 |
| 89 | 354.1 | 0.67 | 2200 |
| 90 | 482.2 | 0.79 | 11 |
| 91 | 387.2 | 0.62 | 6.5 |
| 92 | 515.3 | 0.46 | 1.7 |
| 93 | 544.4 | 0.47 | 1.5 |
| 94 | 521.3 | 0.48 | 1.4 |
| 95 | 462.2 | 0.45 | 2.3 |
| 96 | 535.4 | 0.50 | 1.1 |
| 97 | 445.2 | 0.47 | 3.2 |
| 98 | 459.3 | 0.48 | 1.4 |
| 99 | 459.3 | 0.49 | 1.6 |
| 100 | 521.3 | 0.44 | 2.4 |
| 101 | 534.3 | 0.48 | 1.3 |

Additional assays such as human whole blood TNF inhibition, human hepatocyte stability and CACO-2 permeability were carried out to obtain cellular potency, stability and cell permeability respectively.

Method of Use

The compounds of the invention are effective inhibitors of RIPK2. Therefore, in one embodiment of the invention, there is provided methods of treating RIPK2 mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, pharmacological inhibition of RIPK2 will attenuate pro-inflammatory signaling through the bacterial sensing pathways initiated by NOD1 and NOD2 stimulation. This reduction in inflammatory signaling will provide therapeutic benefit in a variety of autoinflammatory diseases.

These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease (ulcerative colitis and Crohn's disease), Blau syndrome, systemic lupus erythematosus, transplant rejection, multiple sclerosis, inflammatory pain, inflammatory and allergic ocular diseases;

Autoimmune disease or allergic disorder is selected from rheumatoid arthritis, psoriasis, systemic lupus erythromatosis, lupus nephritis, scleroderma, asthma, Chronic Obstructive Pulmonary Disease (COPD), allergic rhinitis, allergic eczema, multiple sclerosis, juvenile rheumatoid arthritis, juvenile idiopathic arthritis, type I diabetes, inflammatory bowel disease, graft versus host disease, psoriatic arthritis, reactive arthritis, ankylosing spondylitis, Crohn's disease, ulcerative colitis, uveitis and non-radiographic spondyloarthropathy.

Cancer including solid tumors, leukemias and lymphomas; and

Renal diseases such as glomerulonephritis or diabetic nephropathy or diabetic kidney disease.

Liver disease such as Non-alcoholic fatty liver disease or non-alcoholic steato-hepatitis (NASH) or cirrhosis of the liver.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

The invention claimed is:

1. A method for modulating receptor interacting serine/threonine-protein kinase 2 activity in a patient, comprising administering to the patient a therapeutically effective amount of a compound selected from the group consisting of:

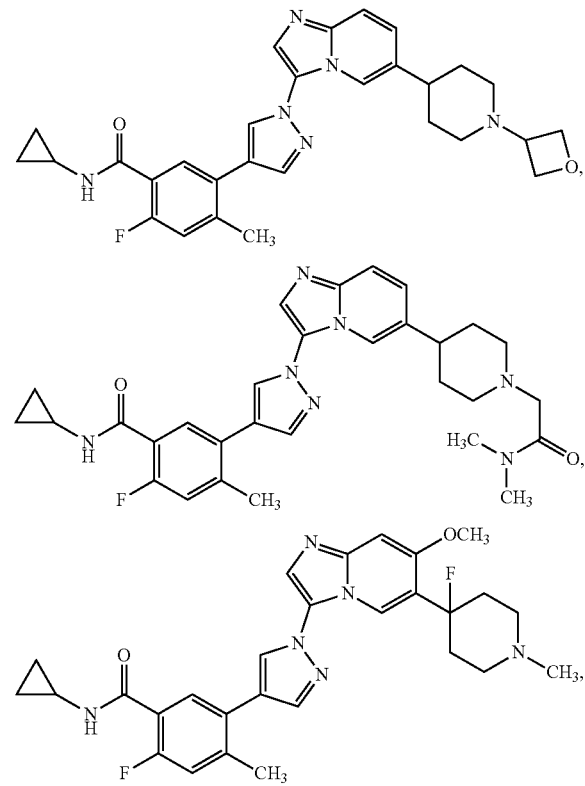

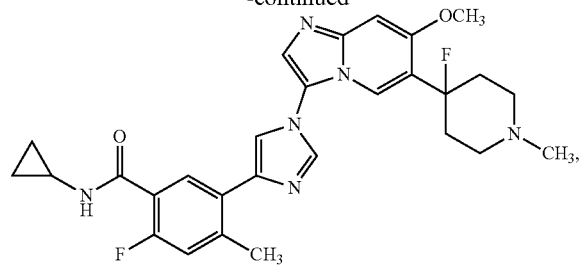

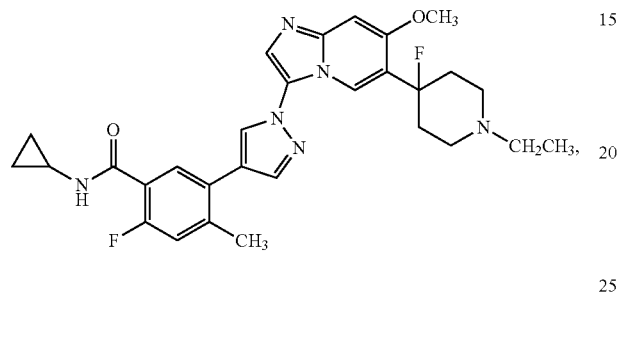

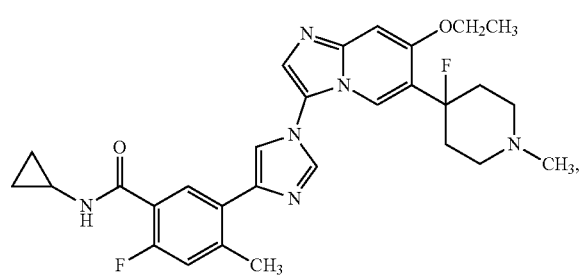

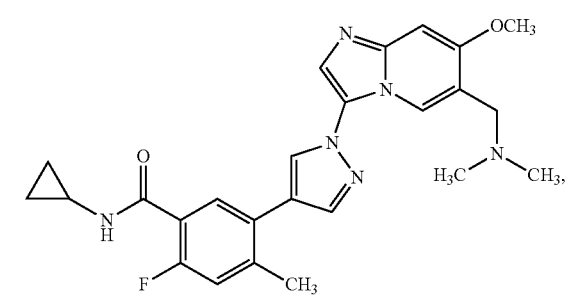

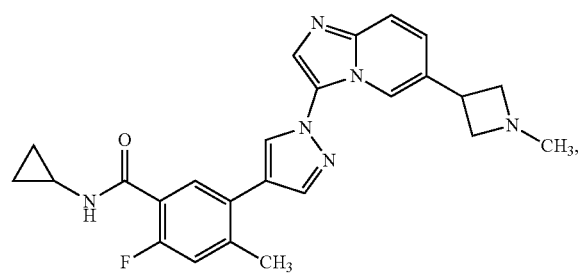

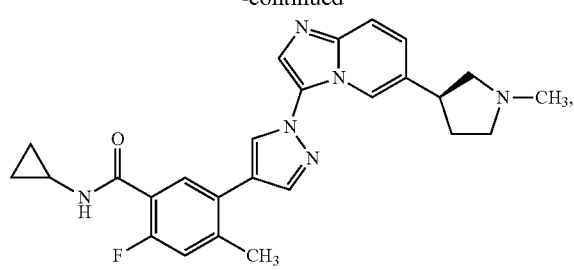

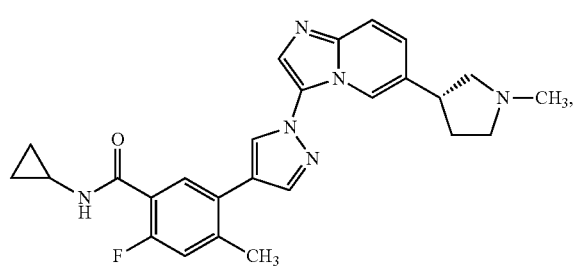

and

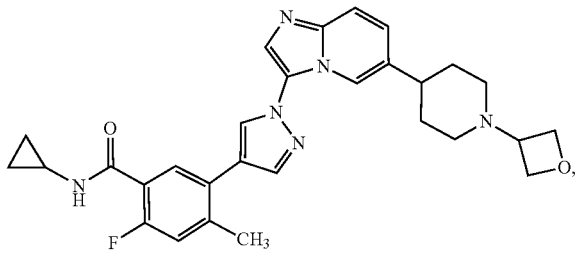 [SMILES: Cc1cc(F)c(C(=O)NC2CC2)cc1-c1cnn(-c2cnc3ccc(C4CCN(C5COC5)CC4)cn23)c1]

or a pharmaceutically acceptable salt thereof.

2. The method of claim 1, wherein the patient has a disease or disorder selected from the group consisting of an autoimmune disease and an allergic disorder.

3. The method of claim 2, wherein the autoimmune disease or allergic disorder is selected from the group consisting of allergic eczema, allergic rhinitis, ankylosing spondylitis, asthma, chronic obstructive pulmonary disease, Crohn's disease, graft versus host disease, inflammatory bowel disease, juvenile idiopathic arthritis, lupus nephritis, multiple sclerosis, non-radiographic spondyloarthropathy, psoriasis, psoriatic arthritis, reactive arthritis, rheumatoid arthritis, scleroderma, systemic lupus erythromatosis, type I diabetes, ulcerative colitis, and uveitis.

4. The method of claim 3, wherein the rheumatoid arthritis is juvenile rheumatoid arthritis.

5. The method of claim 1, wherein the compound is:

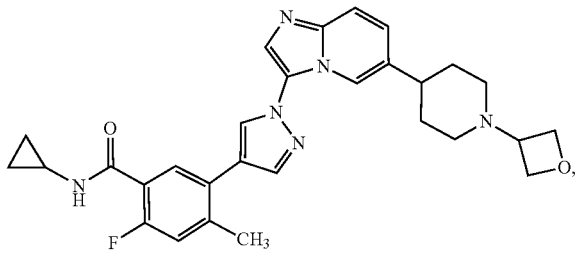 [SMILES: Cc1cc(F)c(C(=O)NC2CC2)cc1-c1cnn(-c2cnc3ccc(C4CCN(C5COC5)CC4)cn23)c1]

or a pharmaceutically acceptable salt thereof.

6. The method of claim 1, wherein the compound is:

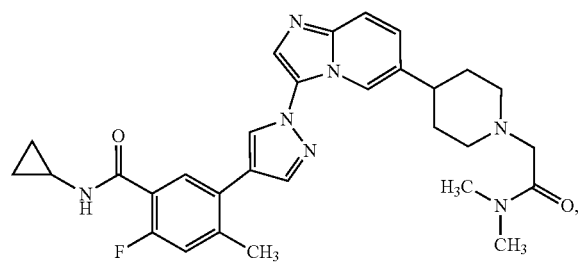 [SMILES: Cc1cc(F)c(C(=O)NC2CC2)cc1-c1cnn(-c2cnc3ccc(C4CCN(CC(=O)N(C)C)CC4)cn23)c1]

or a pharmaceutically acceptable salt thereof.

7. The method of claim 1, wherein the compound is:

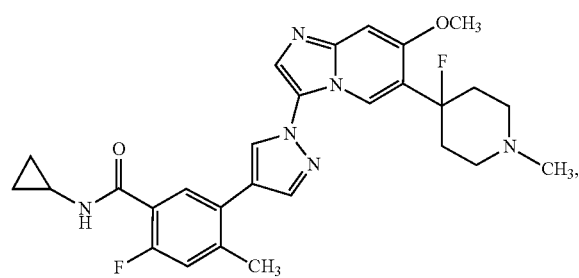 [SMILES: COc1cc2ncc(-n3cc(-c4cc(C(=O)NC5CC5)c(F)cc4C)cn3)n2cc1C1(F)CCN(C)CC1]

or a pharmaceutically acceptable salt thereof.

8. The method of claim 1, wherein the compound is:

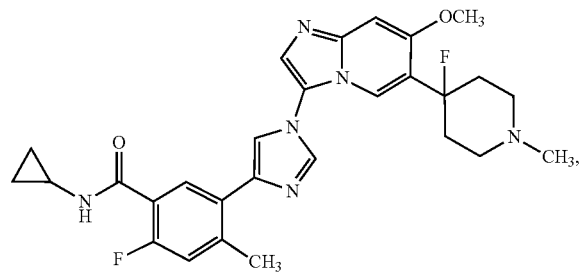 [SMILES: COc1cc2ncc(-n3cnc(-c4cc(C(=O)NC5CC5)c(F)cc4C)c3)n2cc1C1(F)CCN(C)CC1]

or a pharmaceutically acceptable salt thereof.

9. The method of claim 1, wherein the compound is:

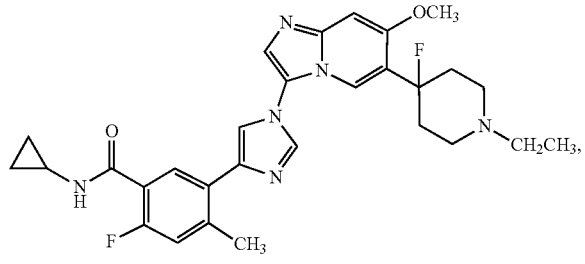 [SMILES: CCN1CCC(F)(c2cn3c(-n4cnc(-c5cc(C(=O)NC6CC6)c(F)cc5C)c4)cnc3cc2OC)CC1]

or a pharmaceutically acceptable salt thereof.

10. The method of claim 1, wherein the compound is:

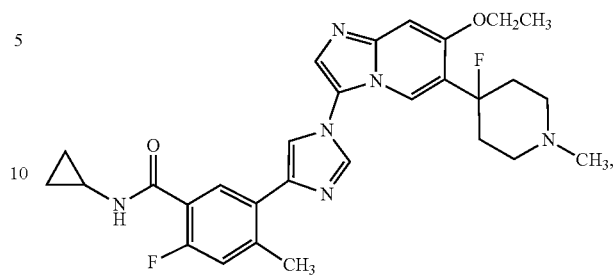

or a pharmaceutically acceptable salt thereof.

11. The method of claim 1, wherein the compound is:

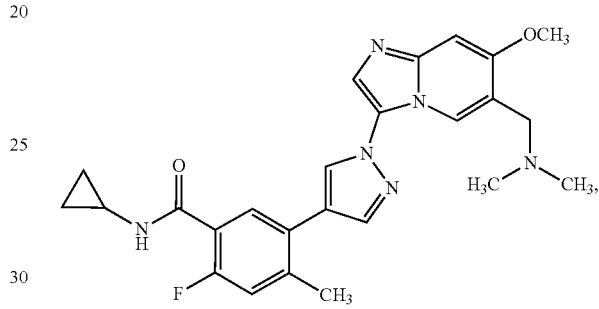

or a pharmaceutically acceptable salt thereof.

12. The method of claim 1, wherein the compound is:

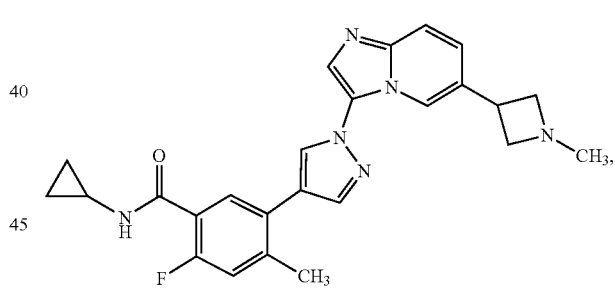

or a pharmaceutically acceptable salt thereof.

13. The method of claim 1, wherein the compound is:

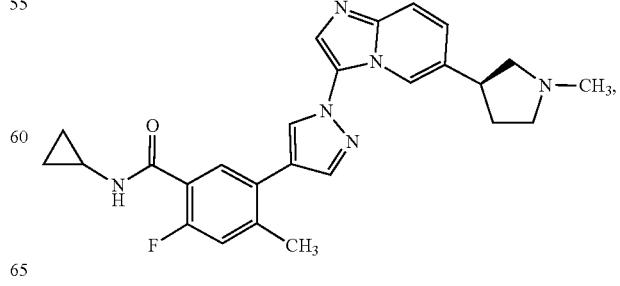

or a pharmaceutically acceptable salt thereof.

14. The method of claim 1, wherein the compound is:
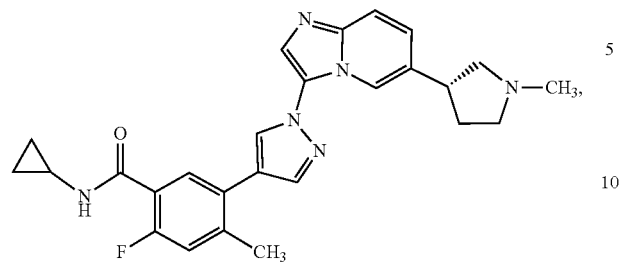
or a pharmaceutically acceptable salt thereof.
* * * * *

UNITED STATES PATENT AND TRADEMARK OFFICE
CERTIFICATE OF CORRECTION

PATENT NO. : 11,130,754 B2
APPLICATION NO. : 16/158407
DATED : September 28, 2021
INVENTOR(S) : Pingrong Liu et al.

It is certified that error appears in the above-identified patent and that said Letters Patent is hereby corrected as shown below:

On the Title Page

Item (72) in the list of inventors, the inventor's name shown as:
ANIL K. PADAYANA
Should be replaced with:
ANIL K. PADYANA Signed and Sealed this
Twenty-first Day of May, 2024

Katherine Kelly Vidal
*Director of the United States Patent and Trademark Office*